US009738698B2

(12) United States Patent
Perricone et al.

(10) Patent No.: US 9,738,698 B2
(45) Date of Patent: *Aug. 22, 2017

(54) PEPTIDE ANALOGS OF ALPHA-MELANOCYTE STIMULATING HORMONE

(71) Applicant: Genzyme Corporation, Cambridge, MA (US)

(72) Inventors: Michael A. Perricone, Sudbury, MA (US); John Lyle Dzuris, Roslindale, MA (US); Timothy E. Weeden, Sturbridge, MA (US); James E. Stefano, Hopkinton, MA (US); Clark Q. Pan, Sudbury, MA (US); Andrea E. Edling, Milford, MA (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/830,572

(22) Filed: Aug. 19, 2015

(65) Prior Publication Data
US 2016/0046688 A1    Feb. 18, 2016

Related U.S. Application Data

(60) Continuation of application No. 13/890,039, filed on May 8, 2013, now Pat. No. 9,115,174, which is a division of application No. 12/408,560, filed on Mar. 20, 2009, now Pat. No. 8,440,793.

(60) Provisional application No. 61/056,373, filed on May 27, 2008.

(51) Int. Cl.
| | | |
|---|---|---|
| *A61K 38/00* | (2006.01) | |
| *A61K 38/34* | (2006.01) | |
| *A61K 47/48* | (2006.01) | |
| *A61K 49/00* | (2006.01) | |
| *C07K 7/08* | (2006.01) | |
| *C07K 14/00* | (2006.01) | |
| *C07K 14/685* | (2006.01) | |
| *C07K 5/113* | (2006.01) | |
| *C07K 5/117* | (2006.01) | |

(52) U.S. Cl.
CPC ............ *C07K 14/685* (2013.01); *A61K 38/34* (2013.01); *A61K 47/48246* (2013.01); *A61K 49/0008* (2013.01); *C07K 5/1021* (2013.01); *C07K 5/1024* (2013.01); *C07K 7/08* (2013.01); *A61K 38/00* (2013.01)

(58) Field of Classification Search
CPC .. A61K 38/00; A61K 38/34; A61K 47/48246; A61K 49/0008; C07K 14/685; C07K 5/1021; C07K 5/1024; C07K 7/08
USPC ......................................... 514/10.7; 530/312
See application file for complete search history.

(56) References Cited

U.S. PATENT DOCUMENTS

| | | |
|---|---|---|
| 4,569,789 A | 2/1986 | Blattler et al. |
| 4,894,443 A | 1/1990 | Greenfield et al. |
| 4,952,394 A | 8/1990 | Senter |
| 5,137,877 A | 8/1992 | Kaneko et al. |
| 5,194,425 A | 3/1993 | Sharma et al. |
| 5,349,066 A | 9/1994 | Kaneko et al. |
| 5,612,474 A | 3/1997 | Patel |
| 5,618,528 A | 4/1997 | Cooper et al. |
| 5,716,928 A | 2/1998 | Benet et al. |
| 5,858,401 A | 1/1999 | Bhalani et al. |
| 6,350,430 B1 | 2/2002 | Dooley et al. |
| 6,969,702 B2 | 11/2005 | Bertilsson et al. |
| 7,166,702 B1 | 1/2007 | McDonald et al. |

FOREIGN PATENT DOCUMENTS

| | | |
|---|---|---|
| CN | 101 302 245 | 11/2008 |
| WO | WO-96/06641 | 3/1996 |
| WO | WO-2005/120588 | 12/2005 |
| WO | WO-2007/008704 | 1/2007 |
| WO | WO-2008/142319 | 11/2008 |

OTHER PUBLICATIONS

Multiple Sclerosis from NINDS, pp. 1-3. Accessed Jul. 23, 2012.*
Sriram S, Steiner I, "Experimental Allergic Encephalomyelitis: A Misleading Model of Multiple Sclerosis," Ann. Neurol, 2005, 58: 939-945.*
Steinman L, Zamvil SS, "How to Successfully Apply Animal Studies in Experimental Allergic Encephalomyelitis to Research on Multiple Sclerosis," Ann Neurol, 2006, 60: 12-21.*
Autoimmune disorders from Merck manual, pp. 1-6. Accessed Aug. 13, 2014.*
Celiac disease from Merck manual, pp. 1-2. Accessed Aug. 13, 2014.*
Hyperthyroidism due to Graves' disease from Merck manual, pp. 1-5. Accessed Aug. 13, 2014.*
Rheumatoid Arthritis from Merck manual, pp. 1-12. Accessed Sep. 16, 2009.*

(Continued)

*Primary Examiner* — Julie Ha
(74) *Attorney, Agent, or Firm* — Morrison & Foerster LLP

(57) ABSTRACT

Provided herein are stable peptide analogs of the native alpha-melanocyte stimulating hormone (α-MSH) having selectivity for the melanocortin 1 receptor (MC1R). Also provided herein are pharmaceutical preparations of the α-MSH peptide analogs, as well as methods of using these analogs in the treatment of medical and veterinary conditions involving MC1R.

14 Claims, 26 Drawing Sheets

(56) References Cited

OTHER PUBLICATIONS

Batra et al., "Insertion of constant region domains of human IgG₁ into CD4-PE40 increases its plasma half-life," Mol. Immunol. (1993) 30:379-386.
Carlsson et al., "Protein thiolation and reversible protein-protein conjugation," Biochem. J. (1978) 173:723-737.
Cumber et al., "Structural features of the antibody-A chain linkage that influence the activity and stability of ricin A chain immunotoxins," Bioconjugate Chem. (1992) 3:397-401.
Definition of Moiety from http://dictionary.reference.com/browse/moiety, pp. 1-3. Accessed Aug. 26, 2010.
Doronina et al., "Development of potent monoclonal antibody auristatin conjugates for cancer therapy," Nature Biotechnol. (2003) 21:778-784, 941.
Eyles et al., "Oral delivery and fate of poly(lactic acid) microsphere-encapsulated Interferon in rats," J. Pharm. Pharmacol. (1997) 49:669-674.
Fattom et al., "Comparative immunogenicity of conjugates composed of the *Staphylococcus aureus* Type 8 capsular polysaccharide bound to carrier proteins by adipic acid dihydrazide or N-succinimidyl-3-(2-pyridyldithio)propionate," Infection & Immun. (1992) 60(2):584-589.
Gao et al., "Controlled release of a contraceptive steroid from biodegradable and injectable gel formulations: in vitro evaluation," Pharm. Res. (1995) 12(6):857-863.
Goldmacher et al., "Photoactivation of toxin conjugates," Bioconj. Chem. (1992) 3:104-107.
Gordon et al., "Topographical localization of the C-terminal region of the voltage-dependent sodium channel from Electrophorus electricus using antibodies raised against a synthetic peptide," Proc. Natl. Acad. Sci. USA (1987) 84:308-312.
Hazum et al., "A photocleavable protecting group for the thiol function of cysteine," in Pept. Proc. Eur. Pept. Symp., 16th (1981), Brunfeldt, (ed.), pp. 105-110.
Huston et al., Protein engineering of antibody binding sites: Recovery of specific activity in an anti-digoxin single-chain Fv analogue produced in *Escherichia coli* PNAS USA (1988) 85:5879-5883.
International Preliminary Report on Patentability for PCT/US2009/037809, issued Nov. 30, 2010.
International Search Report and Written Opinion for PCT/US2009/037809, mailed Oct. 4, 2010, 10 pages.
Johnson, (ed.), Posttranslational Covalent Modification of Proteins, Academic Press, New York (1983) pp. 1-12.
Ladurner et al., "Glutamine, alanine or glycine repeats inserted into the loop of a protein have minimal effects on stability and folding rates," J. Mol. Biol. (1997) 273:330-337.
Mahan et al., "Phase change enzyme immunoassay," Anal. Biochem. (1987) 162:163-170.
Masman et al., "Synthesis and conformational analysis of His-Phe-Arg-Trp-NH2 and analogues with antifungal properties," Bioorg. Med. Chem. (2006) 14(22):7604-7614.
Minto et al., "Pharmacokinetics and pharmacodynamics of nandrolone esters in oil vehicle: effects of ester, injection site and injection volume," J. Pharmacol. Exp. Ther. (1997) 281:93-102.
Murray, (ed.), Gene Transfer and Expression Protocols, The Humana Press Inc., Clifton, NJ, (1991) pp. 109-128.
Newton et al., "Angiogenin single-chain immunofusions: influence of peptide linkers and spacers between fusion protein domains," Biochemistry (1996) 35:545-553.
Ogawa et al., "Synthesis of novel lipopeptide with alpha-melanocyte-stimulation hormone peptide ligand and its effect on liposome stability," Lipids (1999) 34(4):387-394.
Pasut et al. "Polymer-drug conjugation, recent achievements and general strategies," Prog. Polym. Sci. (2007) 32:933-961.
Patent Examination Report No. 1 for AU 2009258054, mailed Mar. 5, 2013.
Proneth et al., "Melanocortin tetrapeptide Ac-His-DPhe-Arg-Trp-NH2 modified at the para position of the benzyl side chain (DPhe):

importance for mouse melanocortin-3 receptor agonist versus antagonist activity," J. Med. Chem. (2008) 51(18):5585-5593.
Rao, "Recent developments of collagen-based materials for medical applications and drug delivery systems," J. Biomater Sci. Polym. Ed. (1995) 7:623-645.
Rohatagi et al., "Pharmacokinetic and pharmacodynamic evaluation of triamcinolone acetonide after intravenous, oral, and inhaled administration," J. Clin. Pharmacol. (1995) 35:1187-1193.
Senter et al., "Novel photocleavable protein crosslinking reagents and their use in the preparation of antibody-toxin conjugates," Photochem. Photobiol. (1985) 42:231-237.
Spatola, "Peptide Backbone Modifications" in Chemistry and Biochemistry of Amino Acids, Peptides and Proteins, vol. 7 (1983), Marcel Dekker, NY, pp. 267-357.
Thorpe et al., "New coupling agents for the synthesis of immunotoxins containing a hindered disulfide bond with improved stability in vivo," Cancer Res. (1987) 47:5924-5931.
TJWA, "Budesonide inhaled via Turbuhaler: a more effective treatment for asthma than beclomethasone dipropionate via Rotahaler," Ann. Allergy Asthma Immunol. (1995) 75:107-111.
Vagner et al., "Novel targeting strategy based on multimeric ligands for drug delivery and molecular imaging: homooligomers of α-MSH," Bioorg. Med. Chem. Lett. (2004) 14(1):211-215.
Veronese, "Peptide and protein PEGylation: a review of problems and solutions," Biomaterials (2001) 22:405-417.
Walden et al., "Major histocompatibility complex-restricted and unrestricted activation of helper T cell lines by liposome-bound antigens," J. Mol. Cell Immunol. (1986) 2:191-197.
Wawryznaczak et al., "Molecular and biological properties of an abrin A chain immunotoxin designed for therapy of human small cell lung cancer," Br. J. Cancer (1992) 66:361-366.
Welhoner et al., "Uptake and concentration of bioactive macromolecules by K562 cells via the transferrin cycle utilizing an acid-labile transferrin conjugate," JBC (1991) 266:4309-4314.
Whitlow et al., "An improved linker for single-chain Fv with reduced aggregation and enhanced proteolytic stability," Protein Engin. (1993) 6:989-995.
Yen et al., "Optically controlled ligand delivery, 1," Makromal. Chem. (1989) 190:69-82.
Yin et al., "Generation of expression constructs that secrete bioactive αMSH and their use in the treatment of experimental autoimmune encephalomyelitis", Gene Therapy (2003) 10:348-355.
Notice of the First Office Action (including English translation) for CN 200980120892.6, mailed Jan. 31, 2013, 17 pages.
Response to First Office Action for CN 200980120892.6, mailed Jun. 17, 2013, 7 pages.
Office Action for MX/a/2010/012990, mailed Jun. 26, 2012, 2 pages.
Response to Office Action for MX/a/2010/012990, mailed Nov. 7, 2012, 8 pages.
Office Action for MX/a/2010/012990, mailed Mar. 6, 2013, 11 pages.
Response to Office Action (translation) for MX/a/2010/012990, mailed Aug. 8, 2013, 10 pages.
Notice of Allowance for MX/a/2010/012990, mailed Aug. 16, 2013, 1 page.
Official Action (translation) for RU 2010153217, mailed Nov. 19, 2011, 4 pages.
Official Action (translation) for RU 2010153217/04(076973), mailed May 17, 2012, 3 pages.
Notification (translation) for RU 2010153217, mailed Nov. 8, 2012, 3 pages.
Decision on Grant (translation) for RU 2010153217/04(076973), dated Oct. 27, 2013, 7 pages.
Office Action (translation) for IL 209369, dated Apr. 14, 2013, 2 pages.
Response to Office Action for IL 209369, dated Aug. 14, 2013, 5 pages.
Restriction Requirement issued in U.S. Appl. No. 12/408,560, dated May 20, 2011, 11 pages.
Response to Restriction Requirement in U.S. Appl. No. 12/408,560, dated Nov. 18, 2011, 8 pages.
Office Action issued in U.S. Appl. No. 12/408,560, dated Jan. 24, 2012, 4 pages.

(56) References Cited

OTHER PUBLICATIONS

Response to Office Action in U.S. Appl. No. 12/408,560, dated Feb. 14, 2012, 9 pages.
Office Action issued in U.S. Appl. No. 12/408,560, dated Apr. 24, 2012, 11 pages.
Response to Office Action in U.S. Appl. No. 12/408,560, dated Aug. 21, 2012, 12 pages.
Office Action issued in U.S. Appl. No. 12/408,560, dated Oct. 11, 2012, 14 pages.
Response to Office Action in U.S. Appl. No. 12/408,560, dated Dec. 10, 2012, 14 pages.
Notice of Allowance issued in U.S. Appl. No. 12/408,560, dated Jan. 11, 2013, 4 pages.
Notice on the Second Office Action for CN 200980120892.6, mailed Nov. 6, 2013, 12 pages.
Notice of Reasons for Rejection (translation) for JP 2011-511661, mailed Nov. 13, 2013, 6 pages.
Notice of Final Rejection (including translation) for JP 2011-511661, mailed Mar. 24, 2014, 8 pages.
Decision on Rejection (including translation) for CN 200980120892.6, mailed Jun. 4, 2014, 12 pages.
Notification of Defects (translation) in IL 209369, mailed Jul. 22, 2014, 2 pages.
Notice of Allowance for JP 2011-511661, mailed Sep. 16, 2014, 3 pages.
Response to Office Action and Request for Reexamination for CN 200980120892.6, filed Sep. 19, 2014, 7 pages.
European Search Report for EP 14178968.5, mailed Nov. 21, 2014, 7 pages.
Office Action for CA 2,726,076, mailed Mar. 18, 2015, 4 pages.
Office Action (with translation) for KR 10-2010-7029335, mailed Jul. 20, 2015, 13.
Office Action for JP 2014-150428, mailed Aug. 12, 2015, 2 pages.
Response to Office Action for CA 2,726,076, filed Sep. 18, 2015, 37 pages.
Restriction Requirement for U.S. Appl. No. 13/890,039 mailed May 12, 2014, 6 pages.
Response to Restriction Requirement for U.S. Appl. No. 13/890,039, filed Jul. 7, 2014, 9 pages.
Office Action for U.S. Appl. No. 13/890,039, mailed Aug. 18, 2014, 20 pages.
Response to Office Action for U.S. Appl. No. 13/890,039, filed Feb. 17, 2015, 20 pages.
Supplemental Amendment in Response to Office Action for U.S. Appl. No. 13/890,039, filed Mar. 26, 2015, 14 pages.
Notice of Allowance for U.S. Appl. No. 13/890,039, mailed Apr. 14, 2105, 8 pages.
Amendment after Allowance for U.S. Appl. No. 13/890,039, filed Jul. 14, 2015, 6 pages.
Response to Amendment for U.S. Appl. No. 13/890,039, mailed Jul. 27, 2015, 2 pages.
Notice on Acceptance of Request for Reexamination (including translation) for CN 200980120892.6, issued Oct. 24, 2014, 2 pages.
Notice on Reexamination (including translation) for CN 200980120892.6, issued May 29, 2015, 13 pages.
Response to Reexamination for CN 200980120892.6, filed Jul. 13, 2015, 8 pages.
Decision on Reexamination (including translation) for CN 200980120892.6, issued Sep. 11, 2015, 12 pages.
Response to Office Action (including translation) for KR 10-2010-7029335, filed Dec. 21, 2015, 86 pages.
Notification of Defects (translation) in IL 209369, issued Jan. 28, 2016, 2 pages.
Notice on the Third Office Action (including translation) for CN 200980120892.6, issued Feb. 3, 2016, 9 pages.
Response to Office Action for JP 2014-150428, filed Feb. 8, 2016, 6 pages.
Response to Office Action (including translated claims) for CN 200980120892.6, filed May 11, 2016, 21 pages.
Decision of Rejection (including translation) for KR 10-2010-7029335, issued May 25, 2016, 10 pages.
Response to Notification of Defects for IL 209369, filed May 29, 2016, 22 pages.
Examination Report for CA 2,726,076, issued Jun. 14, 2016, 3 pages.
Demand for Appellate Trial Against the Decision of Rejection (including translation) for KR 10-2010-7029335, filed Jun. 24, 2016, 26 pages.
Notice of Reasons for Rejection (translation) for JP 2014-150428, issued Jul. 6, 2016, 4 pages.
Notice of Allowance (including translation) for KR 10-2010-7029335, issued Aug. 8, 2016, 3 pages.
Notice of Office Action (translation) for KR 10-2016-7020183, issued Aug. 29, 2016, 4 pages.
Response to Examination Report for CA 2,726,076, filed Dec. 13, 2016, 10 pages.
Notice of Grant of Patent Right for Invention for CN 200980120892.6, dated 10 Oct. 10, 2016, 4 pages. (Including English translation).
Response to Notice of Reasons for Rejection for JP 2014-150428, dated Jan. 5, 2017, 2 pages. (English translation).

* cited by examiner

FIG.10A  FIG.10B
PBS treated  RI α-MSH treated
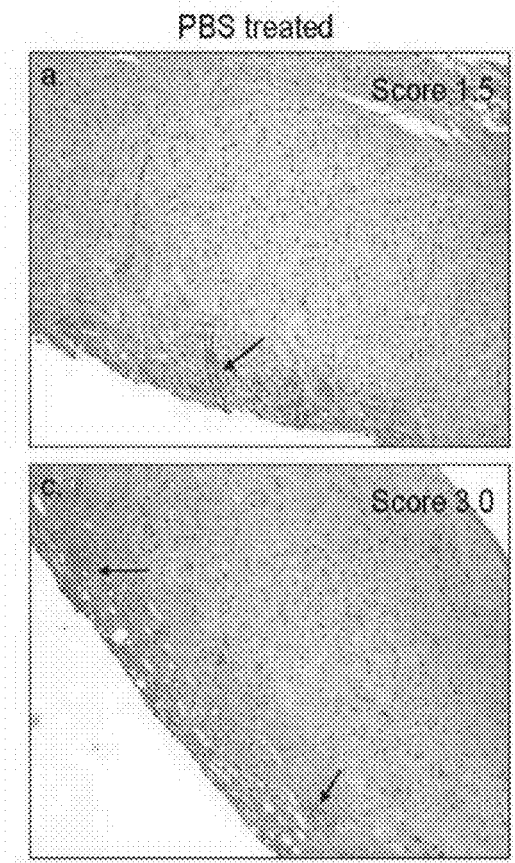
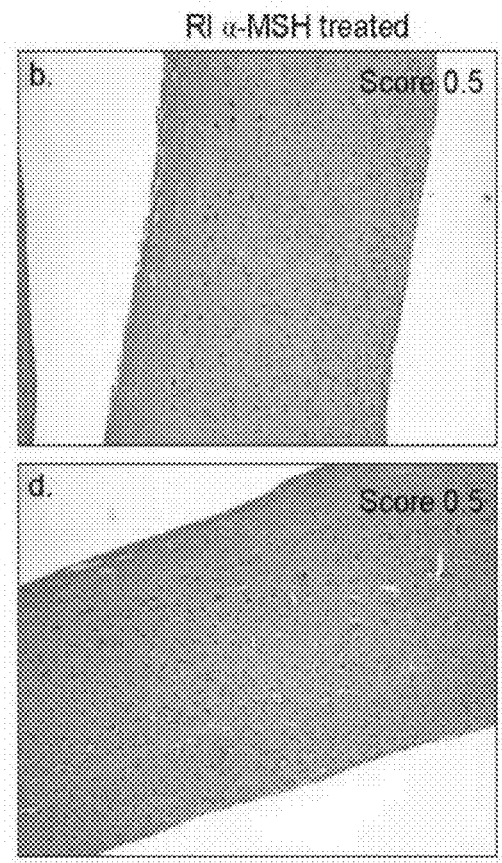
FIG.10C  FIG.10D TNF-α
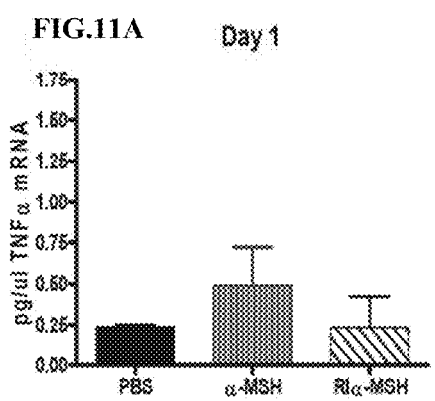
FIG.11A Day 1
IL-10
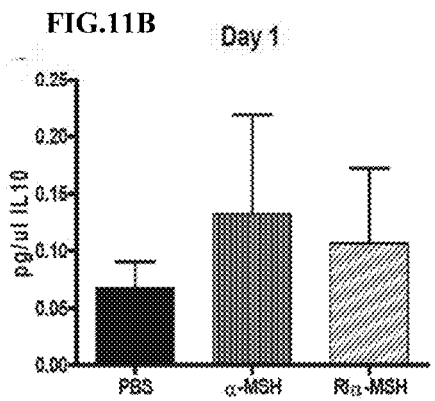
FIG.11B Day 1
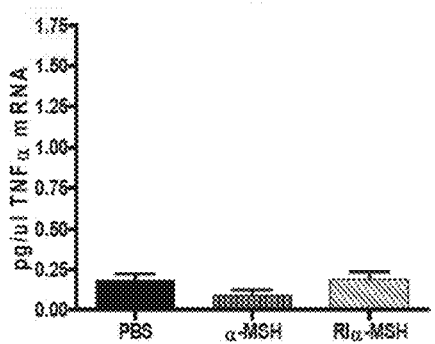
FIG.11C Day 4
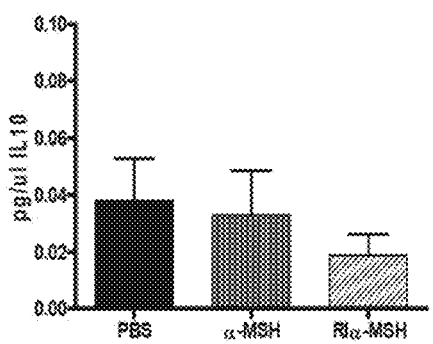
FIG.11D Day 4
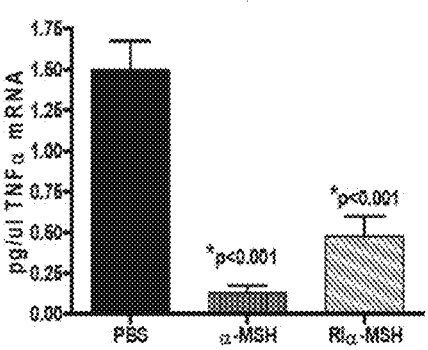
FIG.11E Day 7
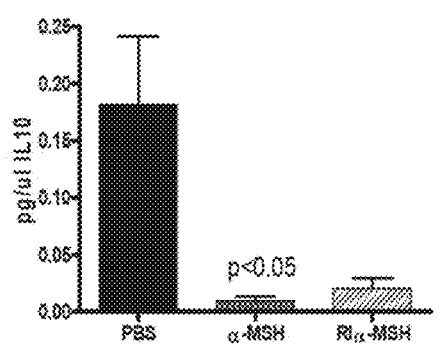
FIG.11F Day 7

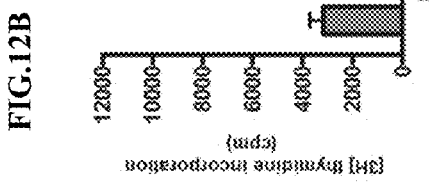
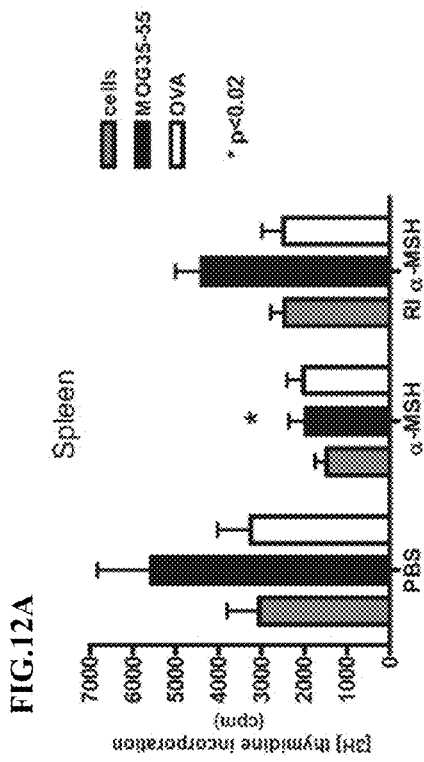
FIG.12B
FIG.12A
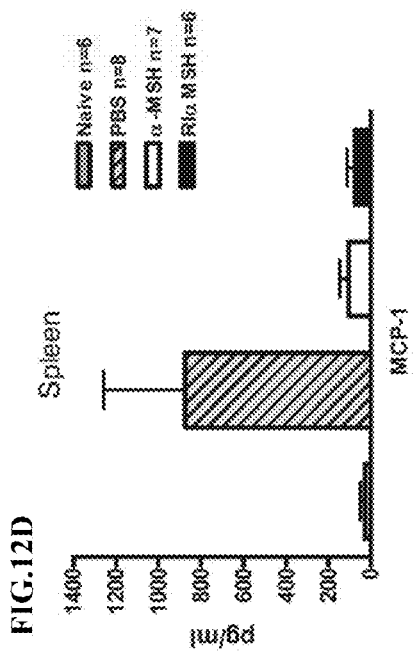
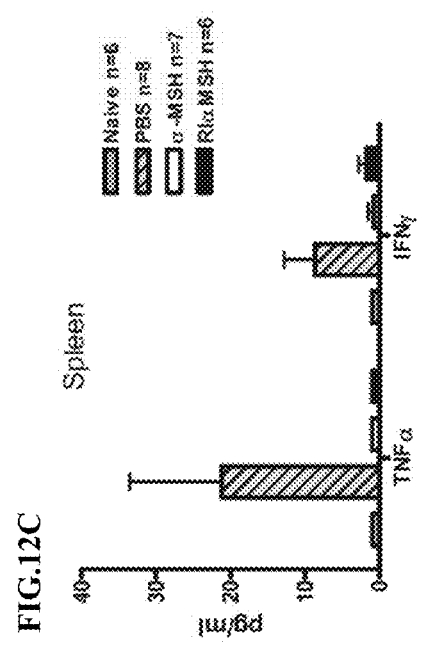
FIG.12D
FIG.12C

SEQUENCE LISTING

```
<160> NUMBER OF SEQ ID NOS: 80

<210> SEQ ID NO 1
<211> LENGTH: 4
<212> TYPE: PRT
<213> ORGANISM: Artificial Sequence
<220> FEATURE:
<223> OTHER INFORMATION: synthetically constructed tetrapeptide
<220> FEATURE:
<221> NAME/KEY: SITE
<222> LOCATION: 2
<223> OTHER INFORMATION: Xaa = D-Cha, D-Phe, or Cha

<400> SEQUENCE: 1

His Xaa Arg Trp
1

<210> SEQ ID NO 2
<211> LENGTH: 4
<212> TYPE: PRT
<213> ORGANISM: Artificial Sequence
<220> FEATURE:
<223> OTHER INFORMATION: synthetically constructed tetrapeptide
<220> FEATURE:
<221> NAME/KEY: SITE
<222> LOCATION: 1, 2, 4
<223> OTHER INFORMATION: D-isomer form
<220> FEATURE:
<221> NAME/KEY: SITE
<222> LOCATION: 3
<223> OTHER INFORMATION: Xaa = D-Cha, D-Phe, or Phe

<400> SEQUENCE: 2

Trp Arg Xaa His
1
```

```
<210> SEQ ID NO 3
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)...(5)
<223> OTHER INFORMATION: D-isomer form

<400> SEQUENCE: 3

Ser Ile Ile Ser Ser
 1               5

<210> SEQ ID NO 4
<211> LENGTH: 13
<212> TYPE: PRT
<213> ORGANISM: Artificial Sequence
<220> FEATURE:
<223> OTHER INFORMATION: synthetically constructed polypeptide
<220> FEATURE:
<221> NAME/KEY: SITE
<222> LOCATION: 1-3, 5-6, 8-13
<223> OTHER INFORMATION: D-isomer form

<400> SEQUENCE: 4

Val Pro Lys Gly Trp Arg Phe His Ser Ile Ile Ser Ser
 1               5                  10

<210> SEQ ID NO 5
<211> LENGTH: 13
<212> TYPE: PRT
<213> ORGANISM: Artificial Sequence
<220> FEATURE:
<223> OTHER INFORMATION: synthetically constructed polypeptide
<220> FEATURE:
<221> NAME/KEY: SITE
<222> LOCATION: 1-3, 5-6, 8-13
<223> OTHER INFORMATION: D-isomer form
<220> FEATURE:
<221> NAME/KEY: SITE
<222> LOCATION: 7
<223> OTHER INFORMATION: Xaa = D-Cha

<400> SEQUENCE: 5

Val Pro Lys Gly Trp Arg Xaa His Ser Ile Ile Ser Ser
 1               5                  10

<210> SEQ ID NO 6
<211> LENGTH: 13
<212> TYPE: PRT
<213> ORGANISM: Artificial Sequence
<220> FEATURE:
<223> OTHER INFORMATION: synthetically constructed polypeptide
<220> FEATURE:
<221> NAME/KEY: SITE
<222> LOCATION: 7
<223> OTHER INFORMATION: Xaa = L-Cha

<400> SEQUENCE: 6

Ser Tyr Ser Met Glu His Xaa Arg Trp Gly Lys Pro Val
 1               5                  10

<210> SEQ ID NO 7
<211> LENGTH: 13
<212> TYPE: PRT
<213> ORGANISM: Artificial Sequence
<220> FEATURE:
<223> OTHER INFORMATION: synthetically constructed polypeptide
<220> FEATURE:
```

```
<221> NAME/KEY: SITE
<222> LOCATION: 1-3, 5-13
<223> OTHER INFORMATION: D-isomer form

<400> SEQUENCE: 7

Val Pro Lys Gly Trp Arg Phe His Glu Met Ser Tyr Ser
1               5                   10

<210> SEQ ID NO 8
<211> LENGTH: 13
<212> TYPE: PRT
<213> ORGANISM: Artificial Sequence
<220> FEATURE:
<223> OTHER INFORMATION: synthetically constructed polypeptide
<220> FEATURE:
<221> NAME/KEY: DOMAIN
<222> LOCATION: (1)...(13)
<223> OTHER INFORMATION: alpha-Melanocyte-stimulating hormone

<400> SEQUENCE: 8

Ser Tyr Ser Met Glu His Phe Arg Trp Gly Lys Pro Val
1               5                   10

<210> SEQ ID NO 9
<211> LENGTH: 13
<212> TYPE: PRT
<213> ORGANISM: Artificial Sequence
<220> FEATURE:
<223> OTHER INFORMATION: synthetically constructed polypeptide
<220> FEATURE:
<221> NAME/KEY: SITE
<222> LOCATION: 1
<223> OTHER INFORMATION: Xaa = D-Val, D-Ala, or D-Lys
<220> FEATURE:
<221> NAME/KEY: SITE
<222> LOCATION: 2
<223> OTHER INFORMATION: Xaa = D-Pro, D-Ala, or D-Lys
<220> FEATURE:
<221> NAME/KEY: SITE
<222> LOCATION: 3
<223> OTHER INFORMATION: Xaa = D-Lys, D-Orn, D-Nle, D-Ala, or D-Lys
<220> FEATURE:
<221> NAME/KEY: SITE
<222> LOCATION: 4
<223> OTHER INFORMATION: Xaa = Gly or D-Ala
<220> FEATURE:
<221> NAME/KEY: SITE
<222> LOCATION: 5
<223> OTHER INFORMATION: Xaa = D-Trp, Trp, D-3-benzothienyl-Ala,
     D-5-hydroxy-Trp, D-5-methoxy-Trp, D-Phe, or D-Ala
<220> FEATURE:
<221> NAME/KEY: SITE
<222> LOCATION: 6
<223> OTHER INFORMATION: Xaa = D-Arg, D-His, or D-Ala
<220> FEATURE:
<221> NAME/KEY: SITE
<222> LOCATION: 7
<223> OTHER INFORMATION: Xaa = D-Cha, D-Phe, Phe, D-4-fluoro-Phg,
     D-3-pyridyl-Ala, D-Thi (2-thienyl-D-alanine), D-Trp,
     D-4-nitro-Phe, or D-Ala
<220> FEATURE:
<221> NAME/KEY: SITE
<222> LOCATION: 8
<223> OTHER INFORMATION: Xaa = D-His, His, D-Arg, Phe, or D-Ala
<220> FEATURE:
<221> NAME/KEY: SITE
<222> LOCATION: 9
<223> OTHER INFORMATION: Xaa = D-Glu, D-Asp, D-citrulline, D-Ser, or
     D-Ala
<220> FEATURE:
<221> NAME/KEY: SITE
<222> LOCATION: 10
<223> OTHER INFORMATION: Xaa = D-Met, D-buthionine, D-Ile, or D-Ala
<220> FEATURE:
<221> NAME/KEY: SITE
```

```
<222> LOCATION: 11
<223> OTHER INFORMATION: Xaa = D-Ser, D-Ile, or D-Ala
<220> FEATURE:
<221> NAME/KEY: SITE
<222> LOCATION: 12
<223> OTHER INFORMATION: Xaa = D-Tyr, D-Ser, or D-Ala
<220> FEATURE:
<221> NAME/KEY: SITE
<222> LOCATION: 13
<223> OTHER INFORMATION: Xaa = D-Ser or D-Ala
<220> FEATURE:
<221> NAME/KEY: SITE
<222> LOCATION: (1)...(13)
<223> OTHER INFORMATION: D-Ala may be present at only 1 position except
      when present concurrently at positions 1-3
<220> FEATURE:
<221> NAME/KEY: SITE
<222> LOCATION: (1)...(13)
<223> OTHER INFORMATION: an L-amino acid may be present at only 1
      position

<400> SEQUENCE: 9

Xaa Xaa Xaa Xaa Xaa Xaa Xaa Xaa Xaa Xaa Xaa Xaa Xaa
1               5                   10

<210> SEQ ID NO 10
<211> LENGTH: 13
<212> TYPE: PRT
<213> ORGANISM: Artificial Sequence
<220> FEATURE:
<223> OTHER INFORMATION: synthetically constructed polypeptide
<220> FEATURE:
<221> NAME/KEY: SITE
<222> LOCATION: 1
<223> OTHER INFORMATION: Xaa = D-Val, D-Ala, or D-Lys
<220> FEATURE:
<221> NAME/KEY: SITE
<222> LOCATION: 2
<223> OTHER INFORMATION: Xaa = D-Pro, D-Ala, or D-Lys
<220> FEATURE:
<221> NAME/KEY: SITE
<222> LOCATION: 3
<223> OTHER INFORMATION: Xaa = D-Lys, D-Orn, D-Nle, D-Ala, or D-Lys
<220> FEATURE:
<221> NAME/KEY: SITE
<222> LOCATION: 4
<223> OTHER INFORMATION: Xaa = Gly or D-Ala
<220> FEATURE:
<221> NAME/KEY: SITE
<222> LOCATION: 5
<223> OTHER INFORMATION: Xaa = D-Trp, Trp, D-3-benzothienyl-Ala,
      D-5-hydroxy-Trp, D-5-methoxy-Trp, D-Phe, or D-Ala
<220> FEATURE:
<221> NAME/KEY: SITE
<222> LOCATION: 6
<223> OTHER INFORMATION: Xaa = D-Arg, D-His, or D-Ala
<220> FEATURE:
<221> NAME/KEY: SITE
<222> LOCATION: 7
<223> OTHER INFORMATION: Xaa = D-Cha, D-Phe, Phe, D-4-fluoro-Phg,
      D-3-pyridyl-Ala, D-Thi (2-thienyl-D-alanine), D-Trp,
      D 4-nitro-Phe, or D Ala
<220> FEATURE:
<221> NAME/KEY: SITE
<222> LOCATION: 8
<223> OTHER INFORMATION: Xaa = D-His, His, D-Arg, Phe, or D-Ala
<220> FEATURE:
<221> NAME/KEY: SITE
<222> LOCATION: 9
<223> OTHER INFORMATION: Xaa = D-Glu, D-Asp, D-citrulline, D-Ser, or
      D-Ala
<220> FEATURE:
<221> NAME/KEY: SITE
<222> LOCATION: 10
<223> OTHER INFORMATION: Xaa = D-Met, D-buthionine, D-Ile, or D-Ala
<220> FEATURE:
<221> NAME/KEY: SITE
```

```
<222> LOCATION: 11
<223> OTHER INFORMATION: Xaa = D-Ser, D-Ile or D-Ala
<220> FEATURE:
<221> NAME/KEY: SITE
<222> LOCATION: 12
<223> OTHER INFORMATION: Xaa = D-Tyr, D-Ser, or D-Ala
<220> FEATURE:
<221> NAME/KEY: SITE
<222> LOCATION: 13
<223> OTHER INFORMATION: Xaa = D-Ser or D-Ala

<400> SEQUENCE: 10

Xaa Xaa Xaa Xaa Xaa Xaa Xaa Xaa Xaa Xaa Xaa Xaa Xaa
1               5                   10

<210> SEQ ID NO 11
<211> LENGTH: 13
<212> TYPE: PRT
<213> ORGANISM: Artificial Sequence
<220> FEATURE:
<223> OTHER INFORMATION: synthetically constructed polypeptide
<220> FEATURE:
<221> NAME/KEY: SITE
<222> LOCATION: 1
<223> OTHER INFORMATION: Xaa = D-Val
<220> FEATURE:
<221> NAME/KEY: SITE
<222> LOCATION: 2
<223> OTHER INFORMATION: Xaa = D-Pro
<220> FEATURE:
<221> NAME/KEY: SITE
<222> LOCATION: 3
<223> OTHER INFORMATION: Xaa = D-Lys, D-Orn, or D-Nle
<220> FEATURE:
<221> NAME/KEY: SITE
<222> LOCATION: 4
<223> OTHER INFORMATION: Xaa = Gly
<220> FEATURE:
<221> NAME/KEY: SITE
<222> LOCATION: 5
<223> OTHER INFORMATION: Xaa = D-Trp, Trp, D-3-benzothienyl-Ala,
      D-5-hydroxy-Trp, D-5-methoxy-Trp, or D-Phe
<220> FEATURE:
<221> NAME/KEY: SITE
<222> LOCATION: 6
<223> OTHER INFORMATION: Xaa = D-Arg or D-His
<220> FEATURE:
<221> NAME/KEY: SITE
<222> LOCATION: 7
<223> OTHER INFORMATION: Xaa = D-Cha, D-Phe, Phe, D-4-fluoro-Phg,
      D-3-pyridyl-Ala, D-Thi (2-thienyl-D-alanine), D-Trp, or
      D 4-nitro-Phe
<220> FEATURE:
<221> NAME/KEY: SITE
<222> LOCATION: 8
<223> OTHER INFORMATION: Xaa = D-His, His, D-Arg, Phe, or D-Ala
<220> FEATURE:
<221> NAME/KEY: SITE
<222> LOCATION: 9
<223> OTHER INFORMATION: Xaa = D-Glu, D-Asp, D-citrulline, or D-Ser
<220> FEATURE:
<221> NAME/KEY: SITE
<222> LOCATION: 10
<223> OTHER INFORMATION: Xaa = D-Met, D-buthionine, or D-Ile
<220> FEATURE:
<221> NAME/KEY: SITE
<222> LOCATION: 11
<223> OTHER INFORMATION: Xaa = D-Ser or D-Ile
<220> FEATURE:
<221> NAME/KEY: SITE
<222> LOCATION: 12
<223> OTHER INFORMATION: Xaa = D-Tyr or D-Ser
<220> FEATURE:
<221> NAME/KEY: SITE
<222> LOCATION: 13
<223> OTHER INFORMATION: Xaa = D-Ser
<220> FEATURE:
```

```
<221> NAME/KEY: SITE
<222> LOCATION: (1)...(13)
<223> OTHER INFORMATION: an L-amino acid may be present at only 1
      position

<400> SEQUENCE: 11

Xaa Xaa Xaa Xaa Xaa Xaa Xaa Xaa Xaa Xaa Xaa Xaa Xaa
1               5                   10

<210> SEQ ID NO 12
<211> LENGTH: 13
<212> TYPE: PRT
<213> ORGANISM: Artificial Sequence
<220> FEATURE:
<223> OTHER INFORMATION: synthetically constructed polypeptide
<220> FEATURE:
<221> NAME/KEY: SITE
<222> LOCATION: 1
<223> OTHER INFORMATION: Xaa = D-Val
<220> FEATURE:
<221> NAME/KEY: SITE
<222> LOCATION: 2
<223> OTHER INFORMATION: Xaa = D-Pro
<220> FEATURE:
<221> NAME/KEY: SITE
<222> LOCATION: 3
<223> OTHER INFORMATION: Xaa = D-Lys, D-Orn, or D-Nle
<220> FEATURE:
<221> NAME/KEY: SITE
<222> LOCATION: 4
<223> OTHER INFORMATION: Xaa = Gly
<220> FEATURE:
<221> NAME/KEY: SITE
<222> LOCATION: 5
<223> OTHER INFORMATION: Xaa = D-Trp or Trp
<220> FEATURE:
<221> NAME/KEY: SITE
<222> LOCATION: 6
<223> OTHER INFORMATION: Xaa = D-Arg
<220> FEATURE:
<221> NAME/KEY: SITE
<222> LOCATION: 7
<223> OTHER INFORMATION: Xaa = D-Cha, D-Phe, Phe or D-Thi
      (2-thienyl-D-alanine)
<220> FEATURE:
<221> NAME/KEY: SITE
<222> LOCATION: 8
<223> OTHER INFORMATION: Xaa = D-His or His
<220> FEATURE:
<221> NAME/KEY: SITE
<222> LOCATION: 9
<223> OTHER INFORMATION: Xaa = D-Glu or D-Ser
<220> FEATURE:
<221> NAME/KEY: SITE
<222> LOCATION: 10
<223> OTHER INFORMATION: Xaa = D-Met, D-buthionine, or D-Ile
<220> FEATURE:
<221> NAME/KEY: SITE
<222> LOCATION: 11
<223> OTHER INFORMATION: Xaa = D-Ser or D-Ile
<220> FEATURE:
<221> NAME/KEY: SITE
<222> LOCATION: 12
<223> OTHER INFORMATION: Xaa = D-Tyr or D-Ser
<220> FEATURE:
<221> NAME/KEY: SITE
<222> LOCATION: 13
<223> OTHER INFORMATION: Xaa = D-Ser
<220> FEATURE:
<221> NAME/KEY: SITE
<222> LOCATION: (1)...(13)
<223> OTHER INFORMATION: an L-amino acid may be present at only 1
      position

<400> SEQUENCE: 12

Xaa Xaa Xaa Xaa Xaa Xaa Xaa Xaa Xaa Xaa Xaa Xaa Xaa
```

```
1               5                   10

<210> SEQ ID NO 13
<211> LENGTH: 5
<212> TYPE: PRT
<213> ORGANISM: Artificial Sequence
<220> FEATURE:
<223> OTHER INFORMATION: synthetically constructed peptide linker

<400> SEQUENCE: 13

Gly Gly Gly Gly Ser
1               5

<210> SEQ ID NO 14
<211> LENGTH: 12
<212> TYPE: PRT
<213> ORGANISM: Artificial Sequence
<220> FEATURE:
<223> OTHER INFORMATION: synthetically constructed peptide linker

<400> SEQUENCE: 14

Gly Lys Ser Ser Gly Ser Gly Ser Glu Ser Lys Ser
1               5                   10

<210> SEQ ID NO 15
<211> LENGTH: 14
<212> TYPE: PRT
<213> ORGANISM: Artificial Sequence
<220> FEATURE:
<223> OTHER INFORMATION: synthetically constructed peptide linker

<400> SEQUENCE: 15

Gly Ser Thr Ser Gly Ser Gly Lys Ser Ser Glu Gly Lys Gly
1               5                   10

<210> SEQ ID NO 16
<211> LENGTH: 18
<212> TYPE: PRT
<213> ORGANISM: Artificial Sequence
<220> FEATURE:
<223> OTHER INFORMATION: synthetically constructed peptide linker

<400> SEQUENCE: 16

Gly Ser Thr Ser Gly Ser Gly Lys Ser Ser Glu Gly Ser Gly Ser Thr
1               5                   10                  15

Lys Gly

<210> SEQ ID NO 17
<211> LENGTH: 14
<212> TYPE: PRT
<213> ORGANISM: Artificial Sequence
<220> FEATURE:
<223> OTHER INFORMATION: synthetically constructed peptide linker

<400> SEQUENCE: 17

Gly Ser Thr Ser Gly Ser Gly Lys Ser Ser Glu Gly Lys Gly
1               5                   10

<210> SEQ ID NO 18
<211> LENGTH: 18
<212> TYPE: PRT
<213> ORGANISM: Artificial Sequence
<220> FEATURE:
<223> OTHER INFORMATION: synthetically constructed peptide linker

<400> SEQUENCE: 18
```

```
Gly Ser Thr Ser Gly Ser Gly Lys Pro Gly Ser Gly Glu Gly Ser Thr
1               5                   10                  15

Lys Gly
```

<210> SEQ ID NO 19
<211> LENGTH: 14
<212> TYPE: PRT
<213> ORGANISM: Artificial Sequence
<220> FEATURE:
<223> OTHER INFORMATION: synthetically constructed peptide linker

<400> SEQUENCE: 19

```
Glu Gly Lys Ser Ser Gly Ser Gly Ser Glu Ser Lys Glu Phe
1               5                   10
```

<210> SEQ ID NO 20
<211> LENGTH: 5
<212> TYPE: PRT
<213> ORGANISM: Artificial Sequence
<220> FEATURE:
<223> OTHER INFORMATION: synthetically constructed peptide linker

<400> SEQUENCE: 20

```
Ser Arg Ser Ser Gly
1               5
```

<210> SEQ ID NO 21
<211> LENGTH: 5
<212> TYPE: PRT
<213> ORGANISM: Artificial Sequence
<220> FEATURE:
<223> OTHER INFORMATION: synthetically constructed peptide linker

<400> SEQUENCE: 21

```
Ser Gly Ser Ser Cys
1               5
```

<210> SEQ ID NO 22
<211> LENGTH: 28
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)...(28)
<223> OTHER INFORMATION: Diphtheria toxin trypsin sensitive linker

<400> SEQUENCE: 22

```
Ala Met Gly Arg Ser Gly Gly Cys Ala Gly Asn Arg Val Gly Ser
1               5                   10                  15

Ser Leu Ser Cys Gly Gly Leu Asn Leu Gln Ala Met
                20                  25
```

<210> SEQ ID NO 23
<211> LENGTH: 13
<212> TYPE: PRT
<213> ORGANISM: Artificial Sequence
<220> FEATURE:
<223> OTHER INFORMATION: synthetic construct
<220> FEATURE:
<221> NAME/KEY: DOMAIN
<222> LOCATION: (1)...(13)
<223> OTHER INFORMATION: alpha-MSH peptide

<400> SEQUENCE: 23

```
Ser Tyr Ser Met Glu His Phe Arg Trp Gly Lys Pro Val
```

```
<210> SEQ ID NO 24
<211> LENGTH: 24
<212> TYPE: DNA
<213> ORGANISM: Artificial Sequence
<220> FEATURE:
<223> OTHER INFORMATION: forward primer

<400> SEQUENCE: 24
ctctgcctcg tcactttctt tcta                                          24

<210> SEQ ID NO 25
<211> LENGTH: 22
<212> TYPE: DNA
<213> ORGANISM: Artificial Sequence
<220> FEATURE:
<223> OTHER INFORMATION: reverse primer

<400> SEQUENCE: 25
aacatgtggg catacagaat cg                                            22

<210> SEQ ID NO 26
<211> LENGTH: 15
<212> TYPE: DNA
<213> ORGANISM: Artificial Sequence
<220> FEATURE:
<223> OTHER INFORMATION: probe

<400> SEQUENCE: 26
ccatgctggc actca                                                    15

<210> SEQ ID NO 27
<211> LENGTH: 25
<212> TYPE: DNA
<213> ORGANISM: Artificial Sequence
<220> FEATURE:
<223> OTHER INFORMATION: mouse TNF alpha forward primer

<400> SEQUENCE: 27
ggcaggtcta ctttggagtc attgc                                         25

<210> SEQ ID NO 28
<211> LENGTH: 25
<212> TYPE: DNA
<213> ORGANISM: Artificial Sequence
<220> FEATURE:
<223> OTHER INFORMATION: mouse TNF alpha reverse primer

<400> SEQUENCE: 28
acattcgagg ctccagtgaa ttcgg                                         25

<210> SEQ ID NO 29
<211> LENGTH: 20
<212> TYPE: DNA
<213> ORGANISM: Artificial Sequence
<220> FEATURE:
<223> OTHER INFORMATION: mouse IL-10 forward primer

<400> SEQUENCE: 29
tgctatgctg cctgctctta                                               20

<210> SEQ ID NO 30
<211> LENGTH: 20
<212> TYPE: DNA
<213> ORGANISM: Artificial Sequence
```

```
<220> FEATURE:
<223> OTHER INFORMATION: mouse IL-10 reverse primer

<400> SEQUENCE: 30
tcatttccga taaggcttgg                                                    20

<210> SEQ ID NO 31
<211> LENGTH: 21
<212> TYPE: DNA
<213> ORGANISM: Artificial Sequence
<220> FEATURE:
<223> OTHER INFORMATION: mouse beta-actin forward primer

<400> SEQUENCE: 31
gtgggccgct ctaggcacca a                                                  21

<210> SEQ ID NO 32
<211> LENGTH: 24
<212> TYPE: DNA
<213> ORGANISM: Artificial Sequence
<220> FEATURE:
<223> OTHER INFORMATION: mouse beta-actin reverse primer

<400> SEQUENCE: 32
ctctttgatg tcacgcacga tttc                                               24

<210> SEQ ID NO 33
<211> LENGTH: 4
<212> TYPE: PRT
<213> ORGANISM: Artificial Sequence
<220> FEATURE:
<223> OTHER INFORMATION: synthetically constructed tetrapeptide

<400> SEQUENCE: 33

His Phe Arg Trp
1

<210> SEQ ID NO 34
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5-13
<223> OTHER INFORMATION: D-isomer form

<400> SEQUENCE: 34

Val Pro Lys Gly Trp Arg Phe His Glu Met Ser Tyr Ala
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5-13
<223> OTHER INFORMATION: D-isomer form

<400> SEQUENCE: 35

Val Pro Lys Gly Trp Arg Phe His Glu Met Ser Ala Ser
1               5                   10
```

```
<210> SEQ ID NO 36
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5-13
<223> OTHER INFORMATION: D-isomer form

<400> SEQUENCE: 36

Val Pro Lys Gly Trp Arg Phe His Glu Met Ala Tyr Ser
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5-13
<223> OTHER INFORMATION: D-isomer form

<400> SEQUENCE: 37

Val Pro Lys Gly Trp Arg Phe His Glu Ala Ser Tyr Ser
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5-13
<223> OTHER INFORMATION: D-isomer form

<400> SEQUENCE: 38

Val Pro Lys Gly Trp Arg Phe His Ala Met Ser Tyr Ser
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5-13
<223> OTHER INFORMATION: D-isomer form

<400> SEQUENCE: 39

Val Pro Lys Gly Trp Arg Phe Ala Glu Met Ser Tyr Ser
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5-13
<223> OTHER INFORMATION: D-isomer form
```

```
<400> SEQUENCE: 40

Val Pro Lys Gly Trp Arg Ala His Glu Met Ser Tyr Ser
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5-13
<223> OTHER INFORMATION: D-isomer form

<400> SEQUENCE: 41

Val Pro Lys Gly Trp Ala Phe His Glu Met Ser Tyr Ser
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5-13
<223> OTHER INFORMATION: D-isomer form

<400> SEQUENCE: 42

Val Pro Lys Gly Ala Arg Phe His Glu Met Ser Tyr Ser
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: ACT_SITE
<222> LOCATION: 1-3, 5-13
<223> OTHER INFORMATION: D-isomer form

<400> SEQUENCE: 43

Val Pro Lys Ala Trp Arg Phe His Glu Met Ser Tyr Ser
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5-13
<223> OTHER INFORMATION: D-isomer form

<400> SEQUENCE: 44

Val Pro Ala Gly Trp Arg Phe His Glu Met Ser Tyr Ser
1               5                   10

<210> SEQ ID NO 45
<211> LENGTH: 13
<212> TYPE: PRT
<213> ORGANISM: Artificial Sequence
<220> FEATURE:
```

```
<223> OTHER INFORMATION: Synthetically Constructed Polypeptide
<220> FEATURE:
<221> NAME/KEY: SITE
<222> LOCATION: 1-3, 5-13
<223> OTHER INFORMATION: D-isomer form

<400> SEQUENCE: 45

Val Ala Lys Gly Trp Arg Phe His Glu Met Ser Tyr Ser
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5-13
<223> OTHER INFORMATION: D-isomer form

<400> SEQUENCE: 46

Ala Pro Lys Gly Trp Arg Phe His Glu Met Ser Tyr Ser
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5-13
<223> OTHER INFORMATION: D-isomer form

<400> SEQUENCE: 47

Ala Ala Ala Gly Trp Arg Phe His Glu Met Ser Tyr Ser
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5-13
<223> OTHER INFORMATION: D-isomer form

<400> SEQUENCE: 48

Lys Lys Lys Gly Trp Arg Phe His Glu Met Ser Tyr Ser
1               5                   10

<210> SEQ ID NO 49
<211> LENGTH: 4
<212> TYPE: PRT
<213> ORGANISM: Artificial Sequence
<220> FEATURE:
<223> OTHER INFORMATION: Synthetically Constructed Tetrapeptide
<220> FEATURE:
<221> NAME/KEY: SITE
<222> LOCATION: 2
<223> OTHER INFORMATION: D-isomer form

<400> SEQUENCE: 49

His Phe Arg Trp
1
```

```
<210> SEQ ID NO 50
<211> LENGTH: 8
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5-8
<223> OTHER INFORMATION: D-isomer form

<400> SEQUENCE: 50

Val Pro Lys Gly Trp Arg Phe His
1               5

<210> SEQ ID NO 51
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: MOD_RES
<222> LOCATION: 3
<223> OTHER INFORMATION: Xaa = D-Orn
<220> FEATURE:
<221> NAME/KEY: SITE
<222> LOCATION: 1-3, 5-13
<223> OTHER INFORMATION: D-isomer form

<400> SEQUENCE: 51

Val Pro Xaa Gly Trp Arg Phe His Glu Met Ser Tyr Ser
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: MOD_RES
<222> LOCATION: 3
<223> OTHER INFORMATION: Xaa = D-Nle
<220> FEATURE:
<221> NAME/KEY: SITE
<222> LOCATION: 1-3, 5-13
<223> OTHER INFORMATION: D-isomer form

<400> SEQUENCE: 52

Val Pro Xaa Gly Trp Arg Phe His Glu Met Ser Tyr Ser
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: VARIANT
<222> LOCATION: 5
<223> OTHER INFORMATION: Xaa = 3-benzothienyl-D-Alanine
<220> FEATURE:
<221> NAME/KEY: SITE
<222> LOCATION: 1-3, 5-13
<223> OTHER INFORMATION: D-isomer form

<400> SEQUENCE: 53

Val Pro Lys Gly Xaa Arg Phe His Glu Met Ser Tyr Ser
1               5                   10
```

```
<210> SEQ ID NO 54
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: VARIANT
<222> LOCATION: 5
<223> OTHER INFORMATION: Xaa = 5-hydroxy-D-Trp
<220> FEATURE:
<221> NAME/KEY: SITE
<222> LOCATION: 1-3, 5-13
<223> OTHER INFORMATION: D-isomer form

<400> SEQUENCE: 54

Val Pro Lys Gly Xaa Arg Phe His Glu Met Ser Tyr Ser
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: VARIANT
<222> LOCATION: 5
<223> OTHER INFORMATION: Xaa = 5-Methoxy-D-Trp
<220> FEATURE:
<221> NAME/KEY: SITE
<222> LOCATION: 1-3, 5-13
<223> OTHER INFORMATION: D-isomer form

<400> SEQUENCE: 55

Val Pro Lys Gly Xaa Arg Phe His Glu Met Ser Tyr Ser
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5-13
<223> OTHER INFORMATION: D-isomer form

<400> SEQUENCE: 56

Val Pro Lys Gly Phe Arg Phe His Glu Met Ser Tyr Ser
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5-13
<223> OTHER INFORMATION: D-isomer form

<400> SEQUENCE: 57

Val Pro Lys Gly Trp Gln Phe His Glu Met Ser Tyr Ser
1               5                   10

<210> SEQ ID NO 58
```

```
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5-13
<223> OTHER INFORMATION: D-isomer form

<400> SEQUENCE: 58

Val Pro Lys Gly Trp Asn Phe His Glu Met Ser Tyr Ser
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5-13
<223> OTHER INFORMATION: D-isomer form

<400> SEQUENCE: 59

Val Pro Lys Gly Trp His Phe His Glu Met Ser Tyr Ser
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: VARIANT
<222> LOCATION: 7
<223> OTHER INFORMATION: Xaa = 4-fluoro-D-phenylglycine
<220> FEATURE:
<221> NAME/KEY: SITE
<222> LOCATION: 1-3, 5-13
<223> OTHER INFORMATION: D-isomer form

<400> SEQUENCE: 60

Val Pro Lys Gly Trp Arg Xaa His Glu Met Ser Tyr Ser
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: VARIANT
<222> LOCATION: 7
<223> OTHER INFORMATION: Xaa = 3-pyridyl-D-Alanine

<400> SEQUENCE: 61

Val Pro Lys Gly Trp Arg Xaa His Glu Met Ser Tyr Ser
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: VARIANT
```

```
<222> LOCATION: 7
<223> OTHER INFORMATION: Xaa = 2-thienyl-D-Alanine
<220> FEATURE:
<221> NAME/KEY: SITE
<222> LOCATION: 1-3, 5-13
<223> OTHER INFORMATION: D-isomer form

<400> SEQUENCE: 62

Val Pro Lys Gly Trp Arg Xaa His Glu Met Ser Tyr Ser
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: VARIANT
<222> LOCATION: 7
<223> OTHER INFORMATION: Xaa = D-Cha
<220> FEATURE:
<221> NAME/KEY: SITE
<222> LOCATION: 1-3, 5-13
<223> OTHER INFORMATION: D-isomer form

<400> SEQUENCE: 63

Val Pro Lys Gly Trp Arg Xaa His Glu Met Ser Tyr Ser
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5-13
<223> OTHER INFORMATION: D-isomer form

<400> SEQUENCE: 64

Val Pro Lys Gly Trp Arg Trp His Glu Met Ser Tyr Ser
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: VARIANT
<222> LOCATION: 7
<223> OTHER INFORMATION: Xaa = 4-Nitro-D-Phe
<220> FEATURE:
<221> NAME/KEY: SITE
<222> LOCATION: 1-3, 5-13
<223> OTHER INFORMATION: D-isomer form

<400> SEQUENCE: 65

Val Pro Lys Gly Trp Arg Xaa His Glu Met Ser Tyr Ser
1               5                   10

<210> SEQ ID NO 66
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
```

```
<221> NAME/KEY: SITE
<222> LOCATION: 1-3, 5-13
<223> OTHER INFORMATION: D-isomer form

<400> SEQUENCE: 66

Val Pro Lys Gly Trp Arg Phe Arg Glu Met Ser Tyr Ser
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5-13
<223> OTHER INFORMATION: D-isomer form

<400> SEQUENCE: 67

Val Pro Lys Gly Trp Arg Phe Trp Glu Met Ser Tyr Ser
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5-13
<223> OTHER INFORMATION: D-isomer form

<400> SEQUENCE: 68

Val Pro Lys Gly Trp Arg Phe Phe Glu Met Ser Tyr Ser
1               5                   10

<210> SEQ ID NO 69
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5-13
<223> OTHER INFORMATION: D-isomer form

<400> SEQUENCE: 69

Val Pro Lys Gly Trp Arg Phe His Asp Met Ser Tyr Ser
1               5                   10

<210> SEQ ID NO 70
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: VARIANT
<222> LOCATION: 9
<223> OTHER INFORMATION: Xaa = D-Citrulline
<220> FEATURE:
<221> NAME/KEY: SITE
<222> LOCATION: 1-3, 5-13
<223> OTHER INFORMATION: D-isomer form

<400> SEQUENCE: 70

Val Pro Lys Gly Trp Arg Phe His Xaa Met Ser Tyr Ser
```

```
<210> SEQ ID NO 71
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: VARIANT
<222> LOCATION: 10
<223> OTHER INFORMATION: Xaa = alpha-methyl-D-Met
<220> FEATURE:
<221> NAME/KEY: SITE
<222> LOCATION: 1-3, 5-13

<400> SEQUENCE: 71

Val Pro Lys Gly Trp Arg Phe His Glu Xaa Ser Tyr Ser
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: VARIANT
<222> LOCATION: 10
<223> OTHER INFORMATION: Xaa = D-buthionine
<220> FEATURE:
<221> NAME/KEY: SITE
<222> LOCATION: 1-3, 5-13
<223> OTHER INFORMATION: D-isomer form

<400> SEQUENCE: 72

Val Pro Lys Gly Trp Arg Phe His Glu Xaa Ser Tyr Ser
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5-13
<223> OTHER INFORMATION: D-isomer form

<400> SEQUENCE: 73

Val Pro Lys Gly Trp Arg Phe His Glu Lys Ser Tyr Ser
1               5                   10

<210> SEQ ID NO 74
<211> LENGTH: 4
<212> TYPE: PRT
<213> ORGANISM: Artificial Sequence
<220> FEATURE:
<223> OTHER INFORMATION: Synthetically Constructed Tetrapeptide
<220> FEATURE:
<221> NAME/KEY: SITE
<222> LOCATION: 1, 2, 4
<223> OTHER INFORMATION: D-isomer form

<400> SEQUENCE: 74

Trp Arg Phe His
1

<210> SEQ ID NO 75
```

```
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5, 6, 8-13
<223> OTHER INFORMATION: D-isomer

<400> SEQUENCE: 75

Val Pro Lys Gly Trp Arg Phe His Glu Met Ser Tyr Ser
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: (1)...(13)
<223> OTHER INFORMATION: D-isomer

<400> SEQUENCE: 76

Val Pro Lys Gly Trp Arg Phe His Ser Ile Ile Ser Ser
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: VARIANT
<222> LOCATION: 7
<223> OTHER INFORMATION: Xaa = D-Cha
<220> FEATURE:
<221> NAME/KEY: VARIANT
<222> LOCATION: 10
<223> OTHER INFORMATION: Xaa = D-Buthionine
<220> FEATURE:
<221> NAME/KEY: SITE
<222> LOCATION: 1-3, 5-13
<223> OTHER INFORMATION: D-isomer form

<400> SEQUENCE: 77

Val Pro Lys Gly Trp Arg Xaa His Glu Xaa Ser Tyr Ser
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 6-13
<223> OTHER INFORMATION: D-isomer form

<400> SEQUENCE: 78

Val Pro Lys Gly Trp Arg Phe His Glu Met Ser Tyr Ser
1               5                   10

<210> SEQ ID NO 79
<211> LENGTH: 13
<212> TYPE: PRT
<213> ORGANISM: Artificial Sequence
```

```
<220> FEATURE:
<223> OTHER INFORMATION: Synthetically Constructed Polypeptide
<220> FEATURE:
<221> NAME/KEY: SITE
<222> LOCATION: 1-3, 5, 7-13
<223> OTHER INFORMATION: D-isomer form

<400> SEQUENCE: 79

Val Pro Lys Gly Trp Arg Phe His Glu Met Ser Tyr Ser
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Synthetically Constructed Polypeptide
<220> FEATURE:
<221> NAME/KEY: SITE
<222> LOCATION: 1-3, 5-7, 9-13
<223> OTHER INFORMATION: D-isomer form

<400> SEQUENCE: 80

Val Pro Lys Gly Trp Arg Phe His Glu Met Ser Tyr Ser
1               5                   10
```

PEPTIDE ANALOGS OF ALPHA-MELANOCYTE STIMULATING HORMONE

CROSS-REFERENCE TO RELATED APPLICATIONS

This application is a continuation of U.S. application Ser. No. 13/890,039, filed May 8, 2013, now U.S. Pat. No. 9,115,174, which is a divisional of U.S. application Ser. No. 12/408,560, filed Mar. 20, 2009, now U.S. Pat. No. 8,440,793, issued May 14, 2013, which claims the priority benefit of U.S. provisional application Ser. No. 61/056,373, filed May 27, 2008. The contents of the above-listed applications are incorporated herein by this reference in their entireties for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 159792008101SeqList.txt, date recorded: Aug. 14, 2015, size: 28,671 bytes.

TECHNICAL FIELD

The invention relates to peptide analogs. In particular, the invention relates to peptide analogs of native alpha-melanocyte stimulating hormone (α-MSH) having selectivity for the melanocortin 1 receptor (MC1R), pharmaceutical preparations thereof, as well as to the use of these analogs in the treatment of medical and veterinary conditions.

BACKGROUND ART

Neuropeptides are small biologically active peptides which are widely distributed throughout the body and have functions from neurotransmitter to growth factor. Much evidence has indicated that neuropeptides have anti-inflammatory capabilities. Among the many neuropeptides are melanocortic peptides (melanocortins), which bind to and stimulate melanocortin (MC) receptors. An example of a melanocortin includes α-melanocyte-stimulating hormone (α-MSH), mainly known for its ability to regulate peripheral pigmentation, but is also known to have anti-inflammatory and immunomodulatory capabilities. α-MSH neuropeptide has been detected in several organs and is produced by neurons, pituitary, gut, skin, and immune cells.

The immunomodulatory capabilities of α-MSH have been demonstrated in models of contact hypersensitivity where hapten-specific tolerance was induced by injection with α-MSH and in suppressing bacterial endotoxin-mediated inflammation. Also, α-MSH has been shown to have therapeutic activity in many animal disease models such as inflammatory bowel disease, arthritis, and experimental heart transplantation. Other animal models of brain inflammation, renal injury and liver inflammation have demonstrated anti-inflammatory effects with this neuropeptide. α-MSH suppresses production of pro-inflammatory cytokines such as TNF-α, IL-6, and IL-1 and inhibits chemokines which reduce macrophage and neutrophil migration to inflammatory sites. Nitric oxide (NO) is a common mediator for various forms of inflammation. NO synthesis by endotoxin-stimulated macrophages and neutrophils has also shown to be inhibited by α-MSH. In addition to its effects on cytokine production, α-MSH downregulates the expression of MHC class I, CD86 and CD40 on monocytes and dendritic cells which effects antigen presentation and co-stimulation. α-MSH is also known to increase the formation of interleukin 10 (IL-10) in monocytes, which is believed to be an important component in immunosuppressive effects.

Although the molecular mechanisms of the immunomodulatory effects of α-MSH are not completely understood, a potential mechanism of action of α-MSH is its ability to inhibit nuclear factor-κB activation in cells. The inhibition of NF-κB results in a suppression of pro-inflammatory cytokine production and nitric oxide synthesis by macrophages. α-MSH functions by binding specific receptors that belong to a group of G-protein-coupled receptors with seven transmembrane domains. These receptors include the melanocortin 1 and melanocortin 3 receptors (MCR-1 and MCR-3) on macrophages by which the binding of α-MSH inhibits NF-κB. Many of the immunomodulatory effects of α-MSH are also mediated through the accumulation of cAMP. The binding of α-MSH to melanocortin receptors increases cAMP levels which may suppress the degradation of IκB and therefore inhibit NF-κB translocation and nitric oxide production.

MC1 receptors, to which α-MSH bind and stimulates has been implicated in various anti-inflammatory and immunomodulatory responses. Five types of melanocortin receptors have been identified, MC1-MC5. MC1-receptors have been found present on melanocytes, melanoma cells, macrophages, neutrophils, glioma cells, astrocytes, monocytes, endothelial cells, in certain areas of the brain, testis and ovary. There remains continued interest in compounds and methods to stimulate MC1-receptors and to produce effective anti-inflammatory and immunomodulatory responses.

SUMMARY OF THE INVENTION

Provided herein is a substantially pure compound that selectively binds melanocortin 1 receptor (MC1R), said compound comprising a core tetrapeptide having the sequence His $Xaa_1$ Arg Trp (SEQ ID NO:1) or D-Trp D-Arg $Xaa_2$ D-His (SEQ ID NO:2); wherein $Xaa_1$ is D-Cha, D-Phe or Cha, and $Xaa_2$ is D-Cha, D-Phe or Phe; or a pharmaceutically acceptable salt thereof. In some embodiments, the C-terminal sequence is D-Ser D-Ile D-Ile D-Ser D-Ser (SEQ ID NO:3).

Further provided herein is a substantially pure compound that selectively binds melanocortin 1 receptor (MC1R), said compound comprising a polypeptide (SEQ ID NO:9) having the sequence:

$Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$, wherein $Xaa_1$ is D-Val, D-Ala or D-Lys;
$Xaa_2$ is D-Pro, D-Ala or D-Lys;
$Xaa_3$ is D-Lys, D-Orn, D-Nle, D-Ala or D-Lys;
$Xaa_4$ is Gly, or D-Ala;
$Xaa_5$ is D-Trp, Trp, D-3-benzothienyl-Ala, D-5-hydroxy-Trp, D-5-methoxy-Trp, D-Phe, or D-Ala;
$Xaa_6$ is D-Arg, D-His, or D-Ala;
$Xaa_7$ is D-Cha, D-Phe, Phe, D-4-fluoro-Phg, D-3-pyridyl-Ala, D-Thi, D-Trp, D-4-nitro-Phe, or D-Ala;
$Xaa_8$ is D-His, His, D-Arg, Phe, or D-Ala;
$Xaa_9$ is D-Glu, D-Asp, D-citrulline, D-Ser, or D-Ala;
$Xaa_{10}$ is D-Met, D-buthionine, D-Ile, or D-Ala;
$Xaa_{11}$ is D-Ser, D-Ile or D-Ala;
$Xaa_{12}$ is D-Tyr, D-Ser, or D-Ala;
$Xaa_{13}$ is D-Ser or D-Ala;

wherein no more than one Xaa$_{1-13}$ is D-Ala except when Xaa$_{1-3}$ are all D-Ala, and no more than one Xaa$_{1-13}$ is an L-amino acid; or a pharmaceutically acceptable salt thereof.

In yet another aspect, provided herein is a substantially pure compound comprising a polypeptide having the sequence:

D-Val D-Pro D-Lys Gly D-Trp D-Arg Phe D-His D-Ser D-Ile D-Ile D-Ser D-Ser (SEQ ID NO:4);

D-Val D-Pro D-Lys Gly D-Trp D-Arg D-Cha D-His D-Ser D-Ile D-Ile D-Ser D-Ser (SEQ ID NO:5);

Ser Tyr Ser Met Glu His Cha Arg Trp Gly Lys Pro Val (SEQ ID NO:6); or

D-Val D-Pro D-Lys Gly D-Trp D-Arg D-Phe D-His D-Glu D-Met D-Ser D-Tyr D-Ser (SEQ ID NO:7); or a pharmaceutically acceptable salt thereof.

In some embodiments, the polypeptides provided herein are PEGylated.

In some embodiments, the compounds provided herein can be conjugated to a biologically active moiety.

In some embodiments, the compounds provided herein selectively bind MC1R. In some embodiments, the compounds exhibit at least one of the following properties: ability to selectively activate MC1R, stability in plasma in vitro, and resistance to protease degradation.

In one aspect, provided herein is a pharmaceutical composition comprising any one of the substantially pure compounds provided herein and a pharmaceutically acceptable excipient.

In another aspect, provided herein is a method of treating an autoimmune disease or condition in a subject in need thereof, comprising administering to said subject a pharmaceutical composition comprising a pharmaceutically acceptable excipient and a therapeutically effective amount of a compound provided herein. In some embodiments, the autoimmune disease or condition is selected from the group consisting of multiple sclerosis, diabetes type I, aplastic anemia, Grave's disease, coeliac disease, Crohn's disease, lupus, arthritis, osteoarthritis, autoimmune uveitis and myasthenia gravis.

In yet another aspect, provided herein is a method of treating inflammation in a subject in need thereof comprising administering to said subject a pharmaceutical composition comprising a pharmaceutically acceptable excipient and a therapeutically effective amount of a compound provided herein. In some embodiments, the inflammation is associated with a disease selected from the group consisting of inflammatory bowel disease, rheumatoid arthritis, allergy, atherosclerosis, psoriasis, gastritis and ischemic heart disease.

In one aspect, provided herein is a method to reduce or inhibit transplant rejection in a subject in need thereof comprising administering to said subject a pharmaceutical composition comprising a pharmaceutically acceptable excipient and a therapeutically effective amount of a compound provided herein.

In another aspect, provided herein is a method to treat melanoma in a subject in need thereof comprising administering to said subject a pharmaceutical comprising a pharmaceutically acceptable excipient and a therapeutically effective amount of a compound provided herein.

In yet another aspect, provided herein is a method to treat melanoma in a subject in need thereof comprising administering to said subject a pharmaceutical comprising a pharmaceutically acceptable excipient and a therapeutically effective amount of a conjugate comprising a compound provided herein that is conjugated to an anti-tumor payload.

The anti-tumor payload can be a radionuclide, a radiosensitizer, a photosensitizer, a chemotherapeutic agent, or a toxin.

In a further aspect, provided herein is a kit comprising the pharmaceutical composition of a compound provided herein and optionally comprising instructions for use.

BRIEF DESCRIPTION OF THE DRAWINGS

FIG. 1A shows data from B10.RIII mice were treated with native α-MSH (100 µg/mouse) IV daily when clinical scores were 2-3. Uveitis was significantly reduced compared with untreated control (p<0.01). FIG. 1B shows data from B10.RIII mice were treated with native α-MSH (100 µg/mouse) IP or dexamethasone IP (0.2 mg/kg or 2.0 mg/kg) daily when clinical scores were 1-2 (n=5). Retinal inflammation was reduced after treatment initiation (p<0.05). Asterisk denotes significant differences from control.

FIG. 2A shows data from mice treated with native α-MSH or retro-RI α-MSH showed reduction in uveitis disease eye scores compared with PBS control mice. FIG. 2B shows individual maximum eye scores of mice in each group on day 16 post-EAU induction (n=8). Asterisk denotes significant differences between groups (p<0.05).

Data is representative of two experiments. Asterisk denotes significant differences between groups (p<0.04).

Figure 6:
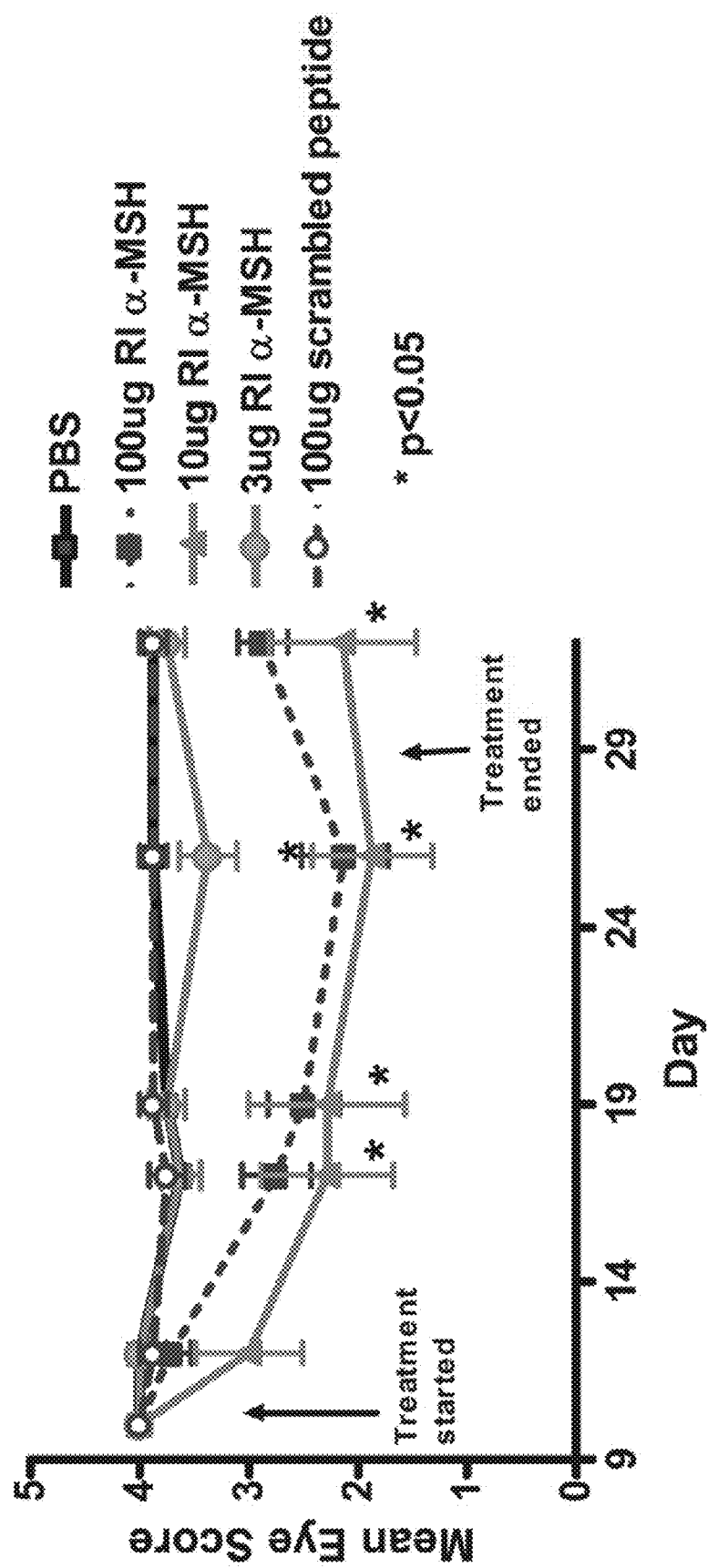

FIG. 6 illustrates efficacy of RI α-MSH in the treatment of retinal inflammation. B10RIII mice were treated with RI α-MSH (3, 10, or 100 μg/mouse) daily by IP injections when clinical scores were 4. Scrambled peptide control was injected at 100 μg/mouse daily. Graph depicts clinical scores over time. Reduced retinal inflammation was observed after treatment initiation with 100 or 10 μg/mouse. Limited beneficial clinical responses were observed in mice treated with a lower dose of RI α-MSH (3 μg/mouse) or with PBS or the control scrambled peptide (n=4). Asterisk denotes significant differences between groups (p<0.05).

Figure 7A:
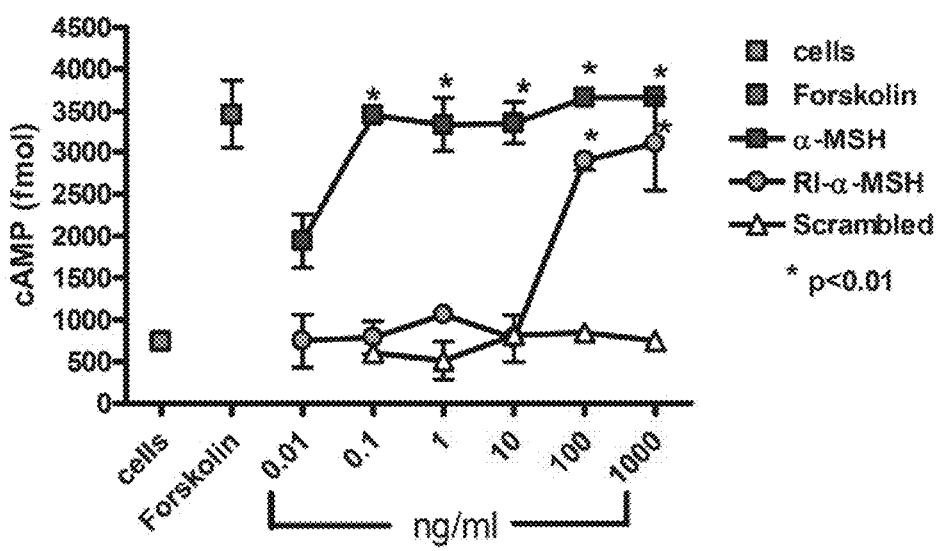
Figure 7B:
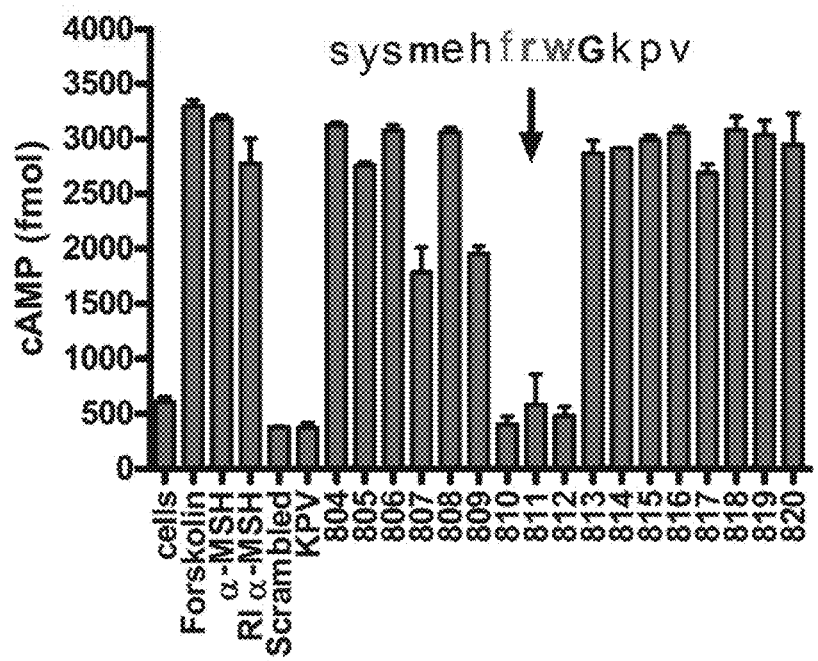

FIGS. 7A-B show the effect of RI α-MSH on cAMP production in murine melanoma cells. cAMP was measured in B16-F1 melanoma cells after treatment of cells with native α-MSH, retro-inverso α-MSH or scrambled control peptide at concentrations 0.01 ng/ml-1000 ng/ml. FIG. 7A shows that both native α-MSH and RI α-MSH significantly increased cAMP levels. Controls used to measure cAMP included forskolin at a 100 μM concentration. FIG. 7B shows alanine scanning data. Alanine substituted peptides of RI α-MSH at 1 μg/ml were tested for increases in cAMP levels in the murine B16-F1 melanoma cell line. Data is representative of two experiments. Sequence list may be found in Table 1. Asterisk denotes significant differences between groups (p<0.01).

Figure 8B:
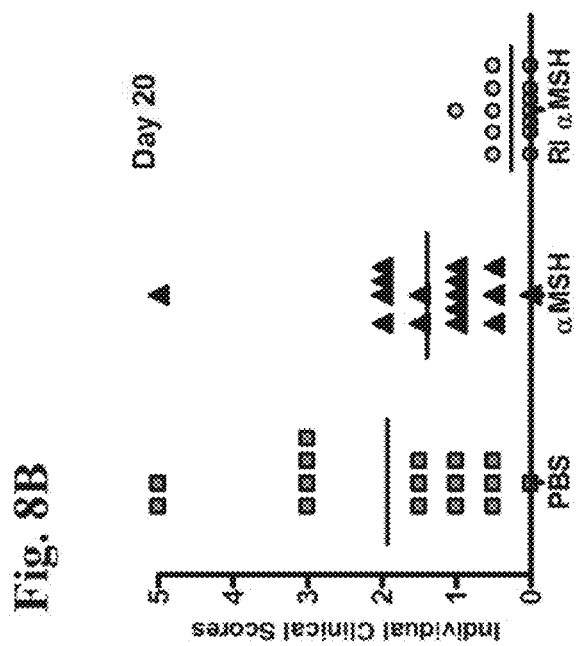
Figure 8A:
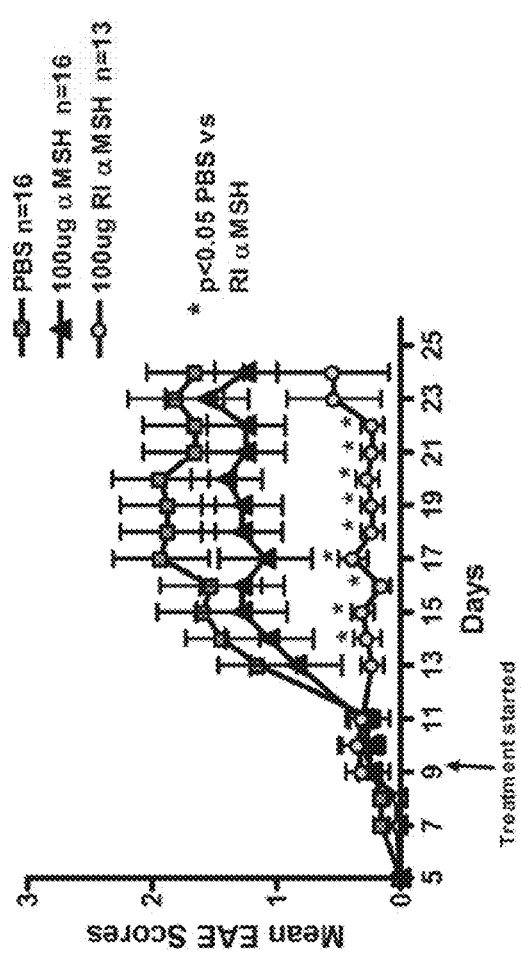

FIGS. 8A-B illustrate the disease course of MOG induced EAE. EAE was induced in C57BL/6 mice by injection of a MOG35-55 peptide (200 μg/mouse) and CFA emulsion. Pertussis toxin was injected on day 0 and day 2. Daily i.p. treatment with 100 μg/mouse of α-MSH, RI α-MSH, or PBS started on Day 10. FIG. 8A shows clinical disease scores recorded daily. FIG. 8B shows individual disease scores in each group on day 20 after disease induction.

Figure 9:
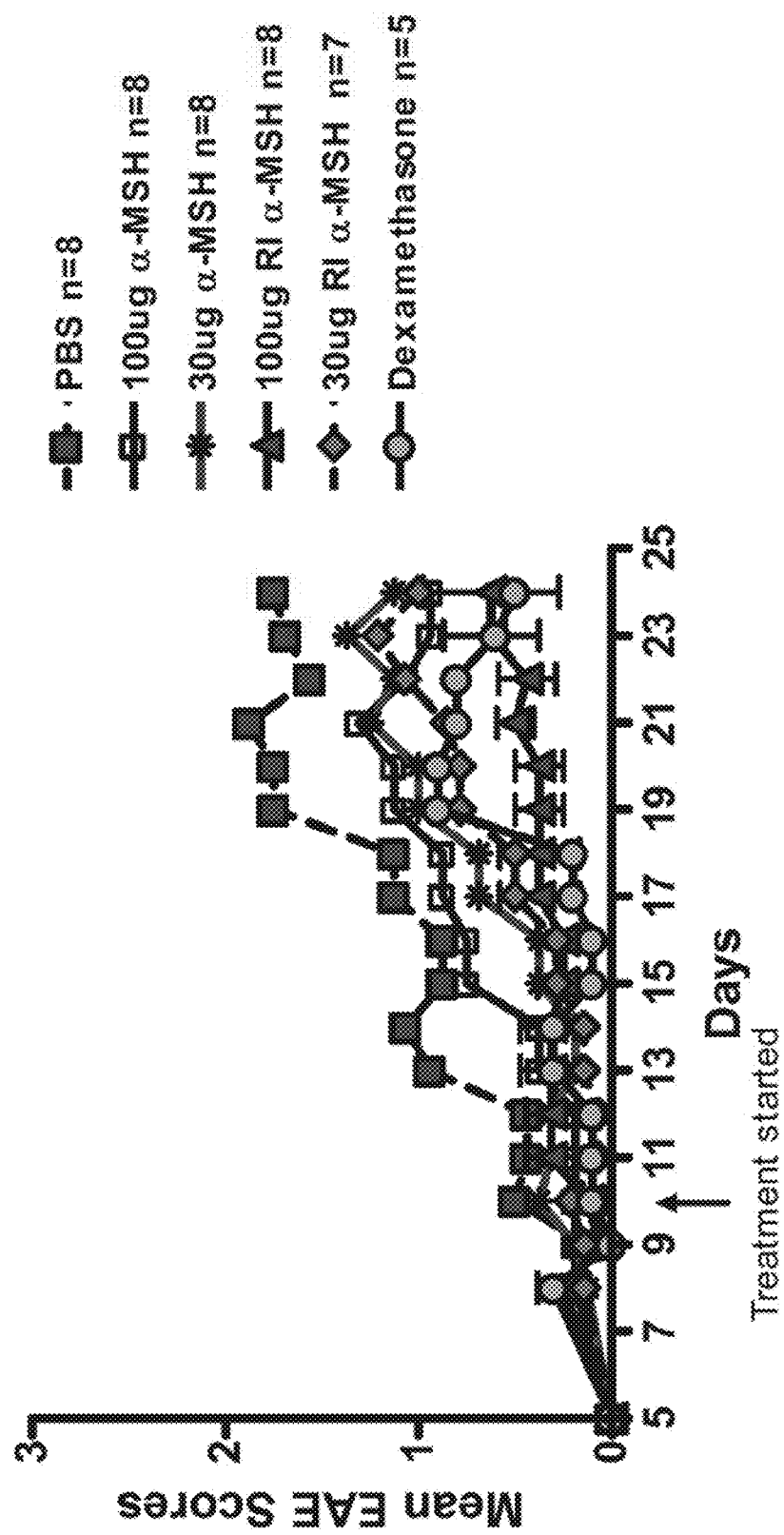

FIG. 9 shows the reduction of mean EAE disease scores by RI α-MSH. EAE was induced in C57BL/6 mice by injections with an emulsion of MOG35-55 peptide (200 μg/mouse) and CFA. Pertussis toxin was injected on day 0 and day 2. Daily i.p. treatment with 100 μg or 30 μg/mouse of α-MSH or RI α-MSH, 2 mg/kg of dexamethasone, or PBS started on Day 10. Clinical disease scores were recorded daily.

FIGS. 10A-D illustrate the spinal cord histology of mice treated with RI α-MSH. EAE was induced in C57BL/6 mice by injection of a MOG35-55 peptide (200 μg/mouse) and CFA emulsion. Pertussis toxin was injected on day 0 and day 2. Daily i.p. treatment with 100 μg/mouse of RI α-MSH began on Day 10. Spinal cord was collected on Day 24 after disease induction. Two representative mice from each group are shown: PBS treated (FIGS. 10A and 10C) and RI α-MSH treated (FIGS. 10B and 10D). Arrows show sites of inflammatory cell infiltration.

FIGS. 11A-F show the amount of TNFα and IL-10 mRNA in the spleen of MOG peptide primed mice during disease phase of EAE. Mice were primed with 200 μg MOG peptide on day 0 and treated with PBS, α-MSH (100 μg) or RI α-MSH (100 μg) daily on days 10-15. Spleens were harvested on Days 1 (FIGS. 11A and 11B), 4 (FIGS. 11C and 11D) and 7 (FIGS. 11E and 11F) after start of treatment and analyzed for TNFα and IL-10 mRNA expression by quantitative PCR. Data show mean of 4 mice in each treatment group. RNA levels are normalized to β-actin.

FIGS. 12A-D illustrate the recall response to MOG 35-55 peptide. Mice were primed with 200 μg MOG35-55 peptide on day 0. On days 2-8 mice were injected i.p. with PBS, 100 μg α-MSH or 100 μg RI α-MSH (n=5). On day 9 spleen (FIG. 12A) and lymph node (FIG. 12B) cells were harvested and stimulated with 25 μg/ml MOG35-55 peptide or OVA peptide in vitro. Cells were pulsed with [3H] thymidine on day 3 in culture. Data show mean±SD. Supernatant was collected from spleen cell cultures stimulated with MOG peptide after 24 hrs and cytokine levels of TNF-α and IFNγ (FIG. 12C) and MCP-1 (FIG. 12D) were analyzed by flow cytometry. Data show mean±SD. Naïve mice were not primed with MOG peptide.

Figure 13A:
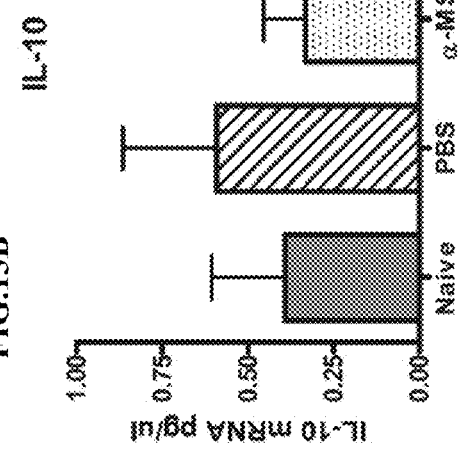
Figure 13B:
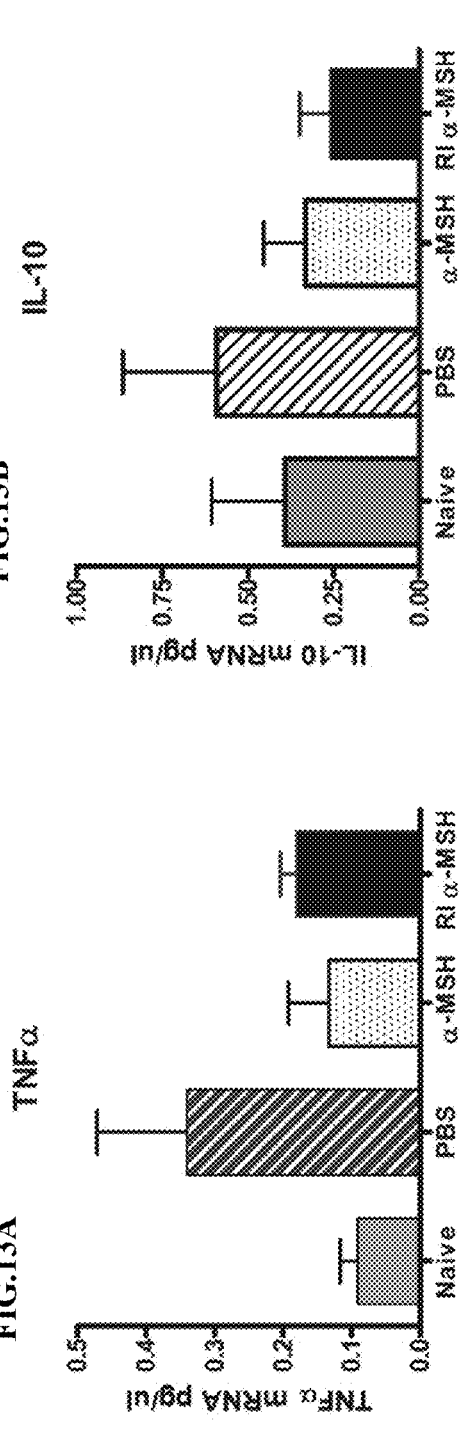
Figure 13C:
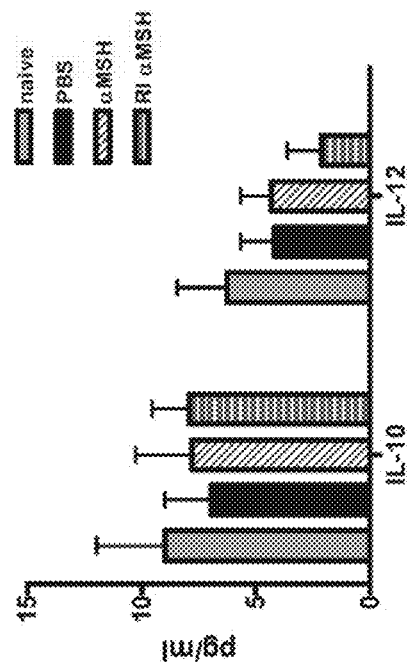
Figure 13D:
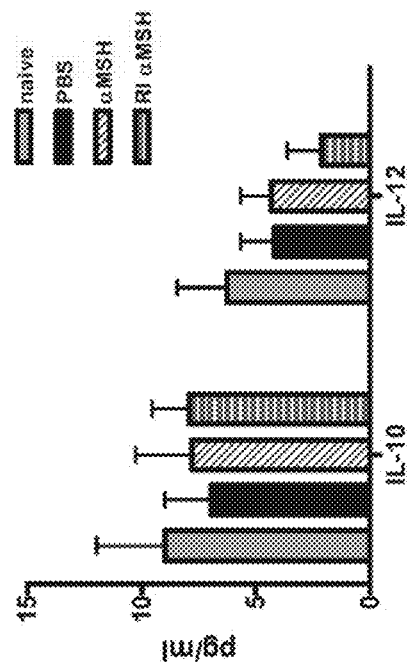

FIGS. 13A-D illustrate cytokine profiles in serum and spleen after RI α-MSH treatment in MOG primed mice. Mice were primed with 200 μg MOG35-55 peptide on day 0. On days 2-8 mice were injected i.p. with PBS, 100 μg α-MSH or 100 μg RI α-MSH (n=5). On day 9 spleen and serum was collected. FIGS. 13A and 13B show TNF-α and IL-10 mRNA levels in the spleen, respectively, quantitated by real time PCR. Data show the mean of 4 mice in each treatment group. RNA levels are normalized to β-actin. Serum was also analyzed for cytokine levels by flow cytometry. FIG. 13C shows TNF-α, MCP-1, IL-6 serum levels, and FIG. 13D shows IL-10 and IL-12 serum levels. Naïve mice were not primed with MOG peptide. Data show mean±SD.

Figure 14B:
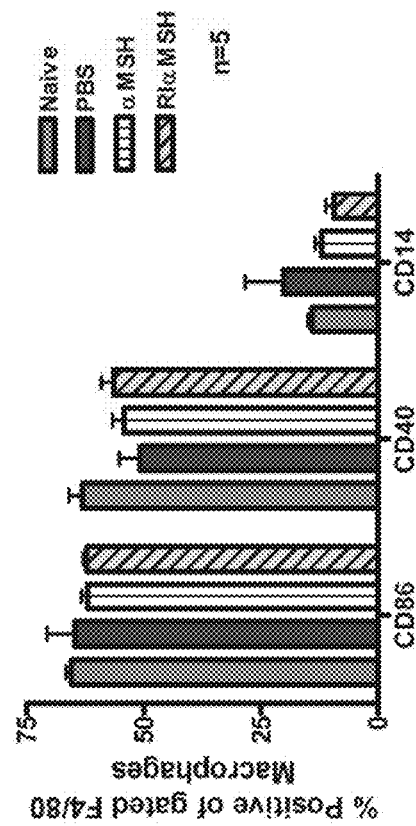
Figure 14A:
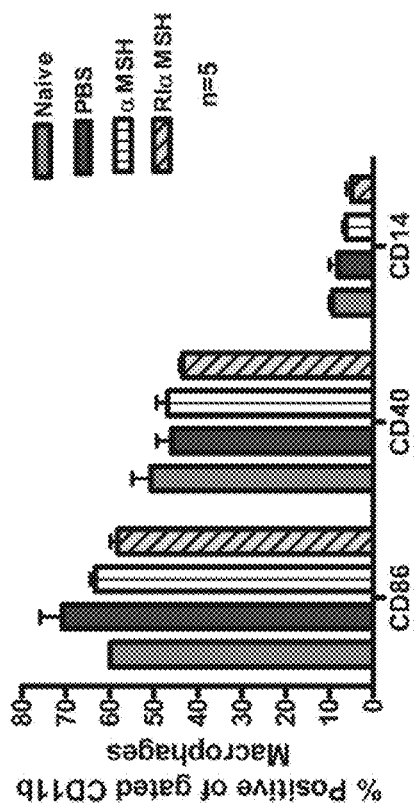

FIGS. 14A-B show the effect of α-MSH and RI α-MSH on macrophage markers. Mice were primed with MOG peptide in vivo and treated daily with α-MSH or RI α-MSH (100 μg/mouse) on days 1-7. Splenic macrophages were analyzed by flow cytometry for expression levels of CD14, CD40 and CD86. Cells were gated on either the CD11b$^+$ (FIG. 14A) or F4/80$^+$ (FIG. 14B) macrophage cell population. Data show both the mean percent positive of the gated macrophage population (n=5).

Figure 15A:
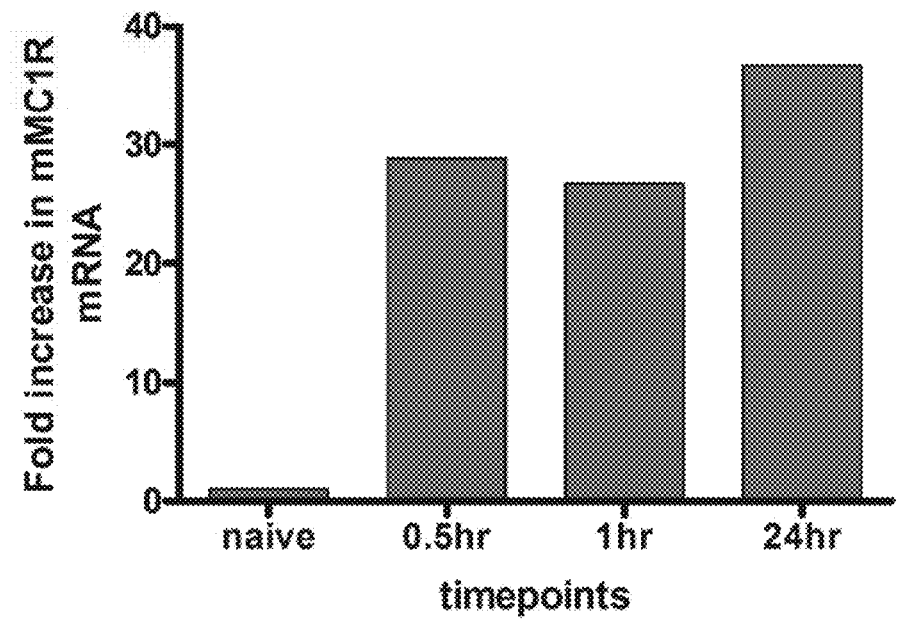
Figure 15B:
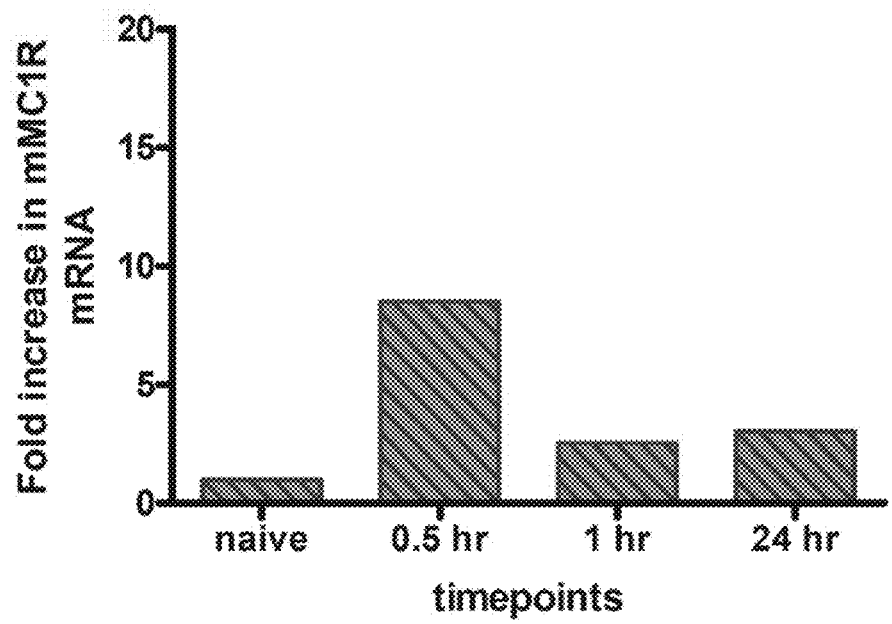

FIGS. 15A-B illustrate an LPS-induced increase of mMC1R mRNA levels in both the peritoneal macrophages (FIG. 15A) and spleen (FIG. 15B). C57BL/6 mice (n=4) were injected i.p. with LPS (1 μg/mouse). Peritoneal macrophages and spleen were harvested at 0.5 hr, 1 hr, and 24 hr. mMC1R mRNA levels were quantitated by real time PCR. RNA levels were normalized to 18s.

FIGS. 16A-F show the effect of MSH is an in vivo LPS inflammation model. C57BL/6 mice were injected with 1 μg of LPS, i.p. After 30 min, mice were treated with Dexamethasone (2 mg/kg) and α-MSH (FIGS. 16A-16C) or RI α-MSH analog 891 (FIGS. 16D-16F), i.p. Serum was collected 2 hours after LPS challenge. The levels of TNF-α (FIGS. 16A and 16D), MCP-1 (FIGS. 16B and 16E), and IL-10 (FIGS. 16C and 16F) were analyzed by cytometric bead assay by flow cytometry. Data show individual cytokine measurements and mean of each group (n=6).

Figure 17A:
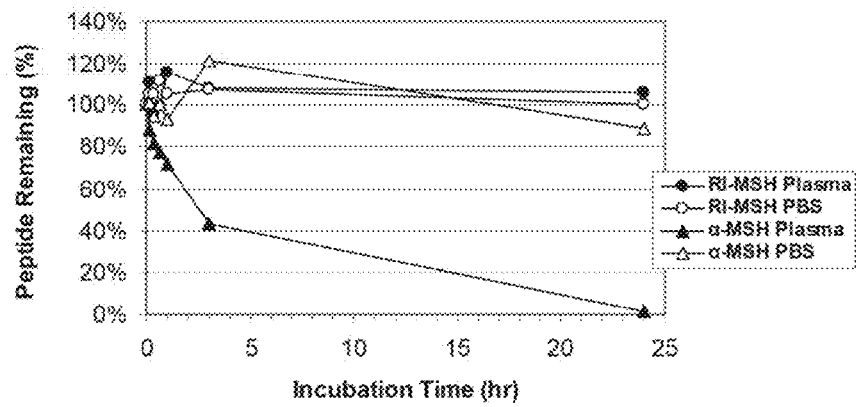
Figure 17B:
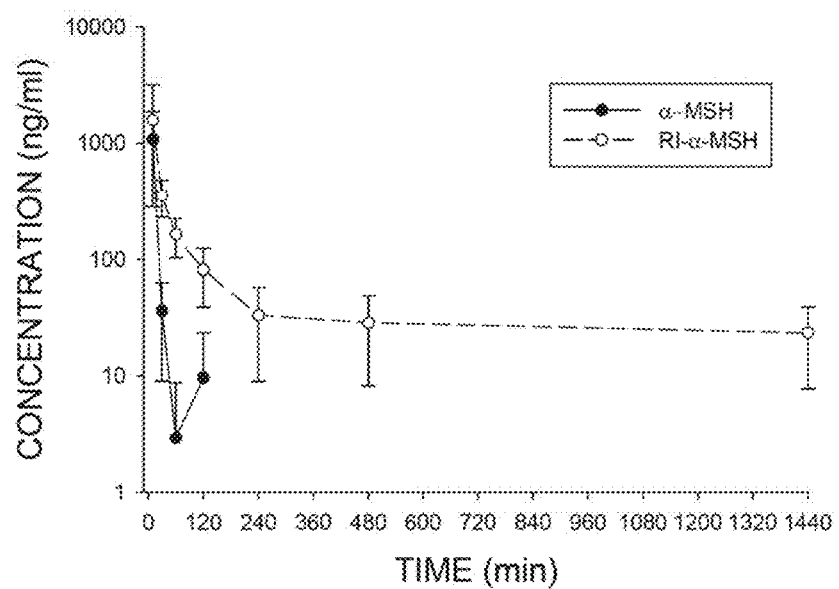

FIGS. 17A-B illustrate stability of RI-α-MSH and α-MSH in plasma and serum. FIG. 17A shows RI-α-MSH and α-MSH peptide stability in plasma and PBS at 37° C. FIG. 17B shows serum half-life of RI-α-MSH and α-MSH peptide after a single intravenous injection.

Figure 18A:
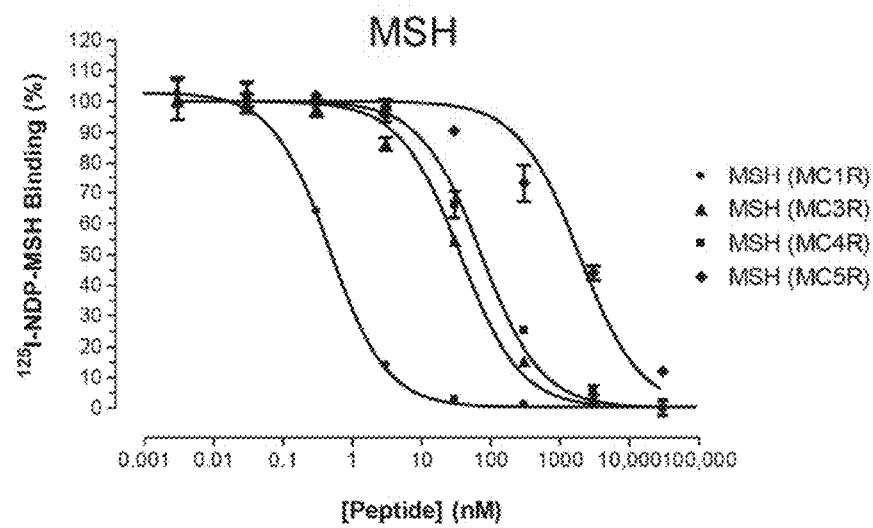
Figure 18B:
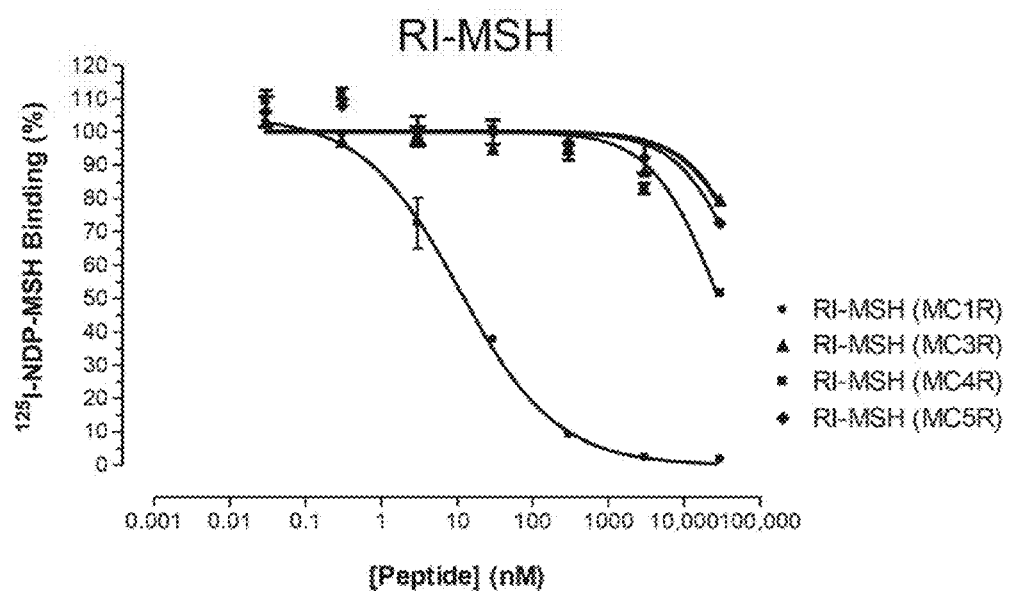

FIGS. 18A-B show the results of binding studies of MSH (FIG. 18A) and RI-MSH (FIG. 18B) to melanocortin receptors 1, 3, 4 and 5.

Figure 19:
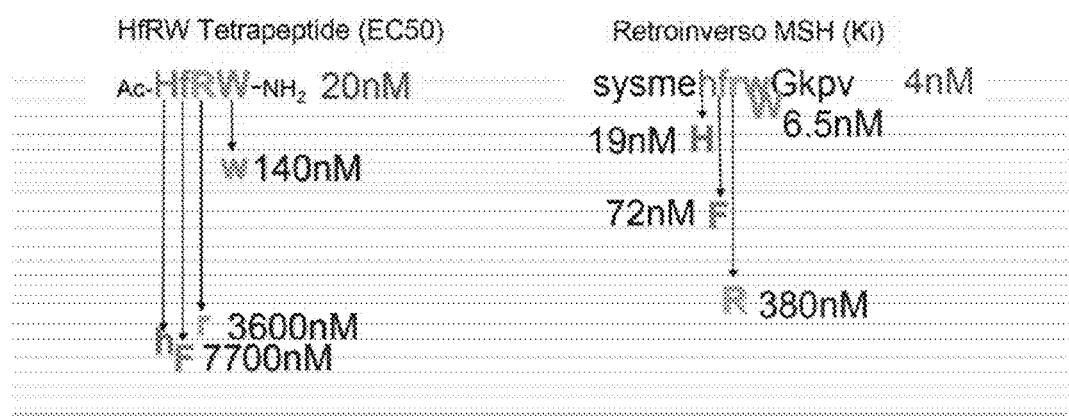

FIG. 19 shows inversion of the core tetrapeptide HfRW (variant disclosed in SEQ ID NO:1) and retroinverso MSH.

Figure 20A:
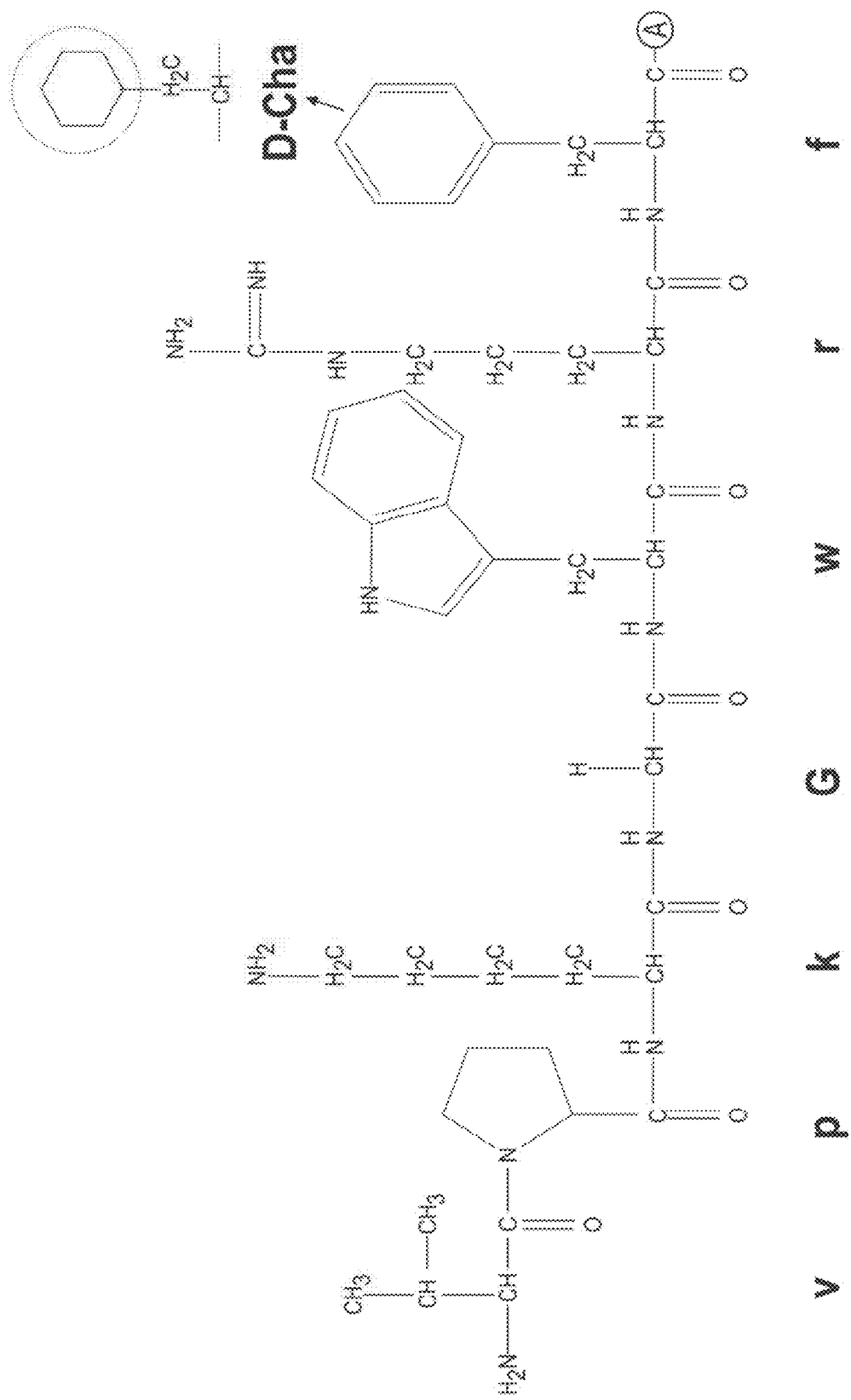
Figure 20B:
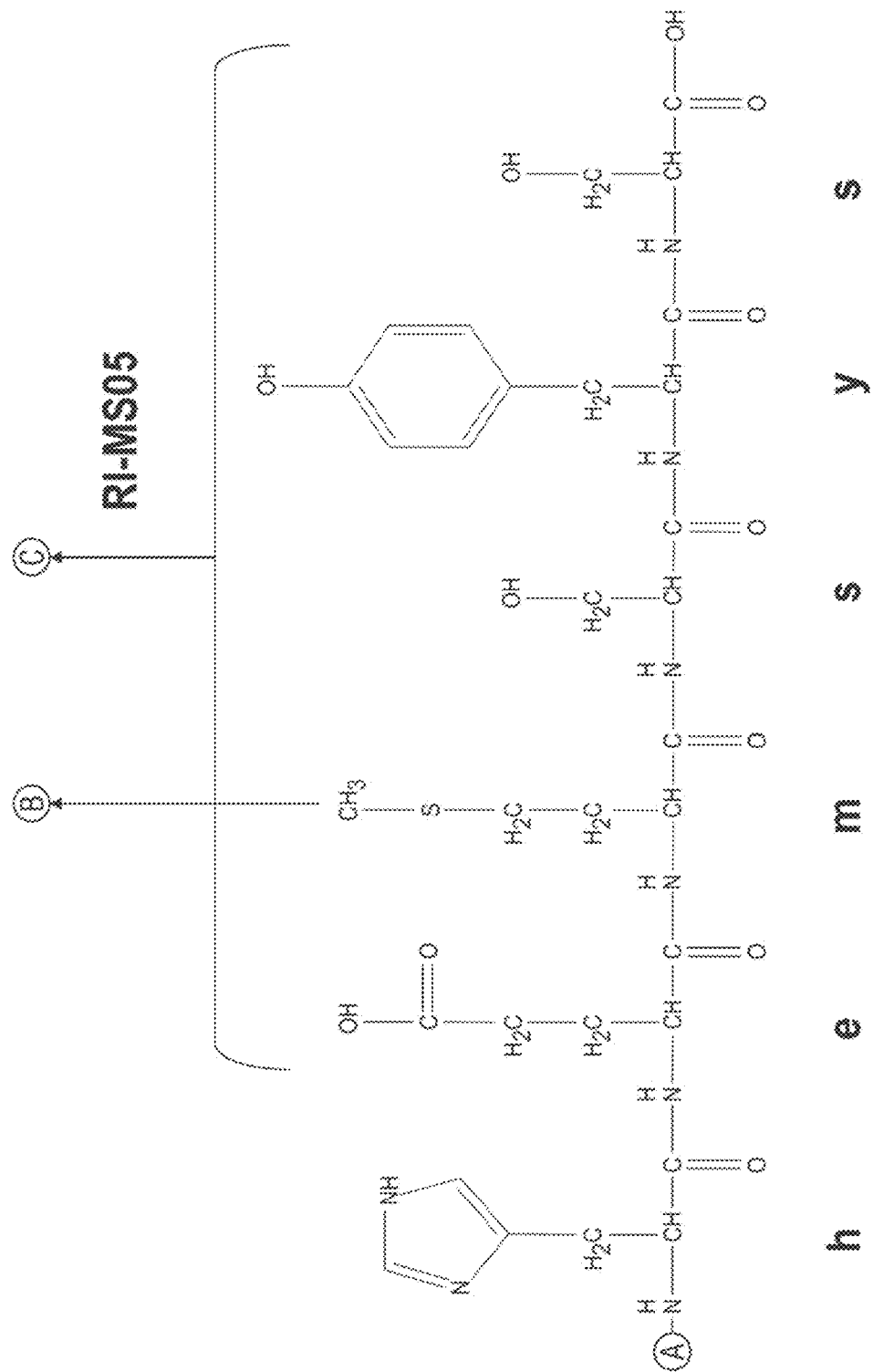
Figure 20C:
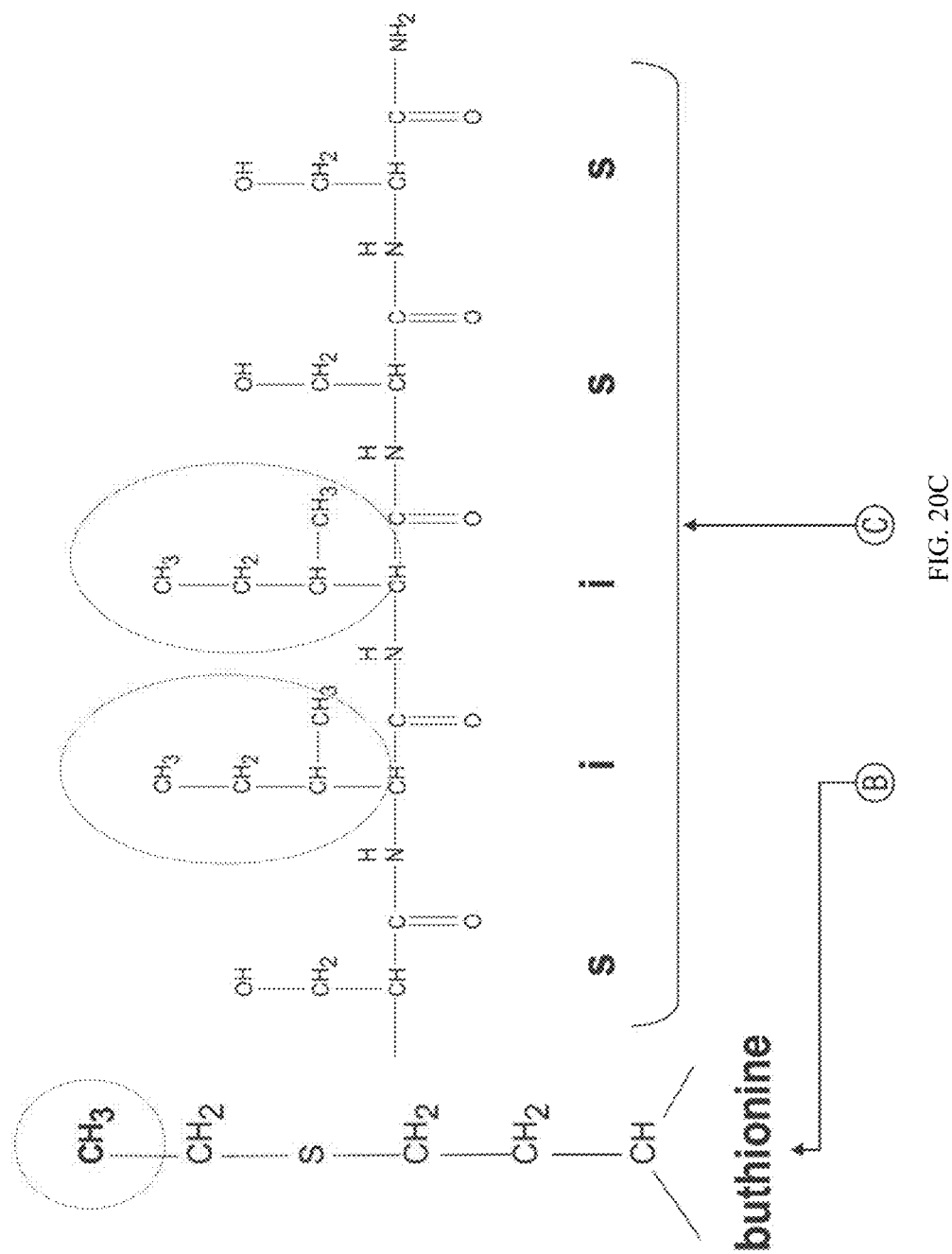

FIGS. 20A-C illustrates substitution of non-natural amino acid residues at varying positions of RI-MSH.

Figure 21:
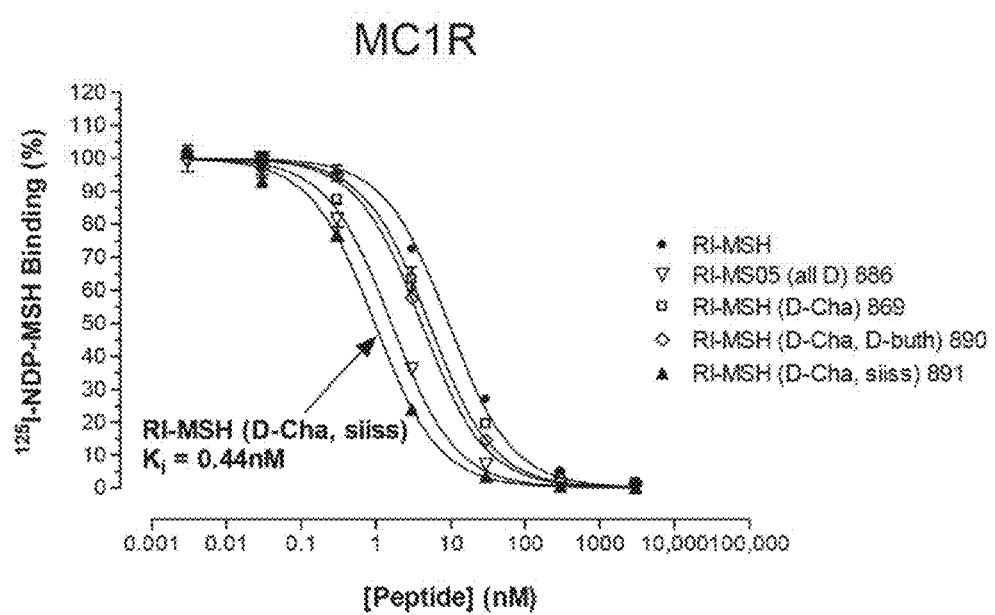

FIG. 21 illustrates a representative competitive binding assay of RI-MSH and variations thereof in MC1R.

Figure 22A:
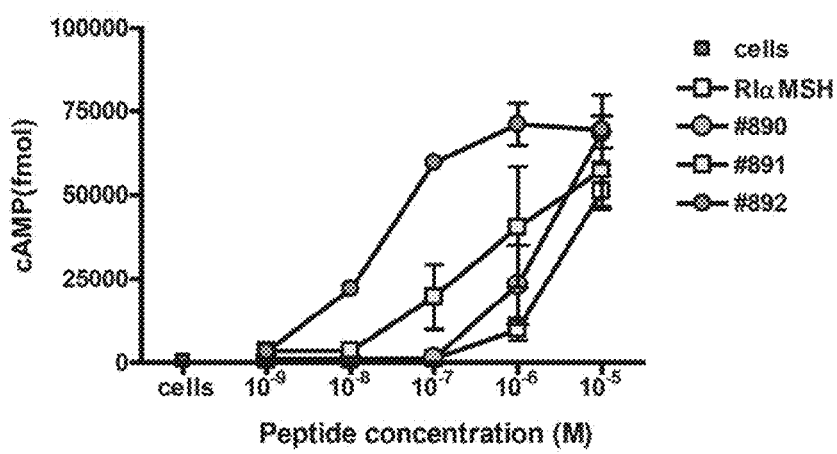
Figure 22B:
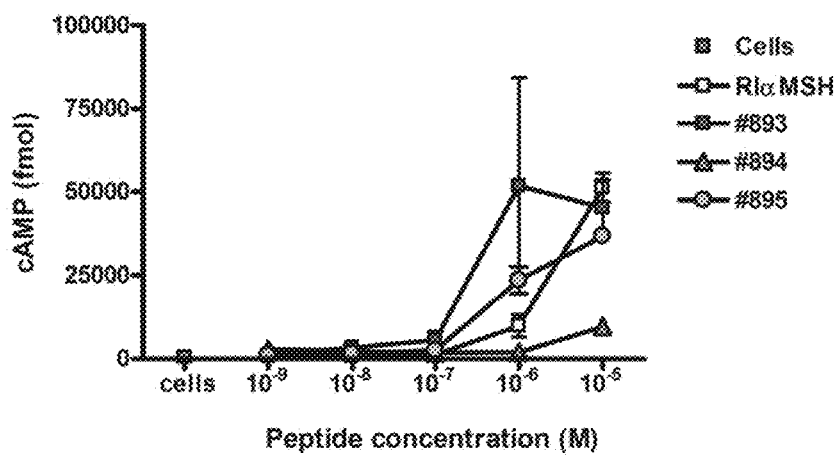
Figure 22C:
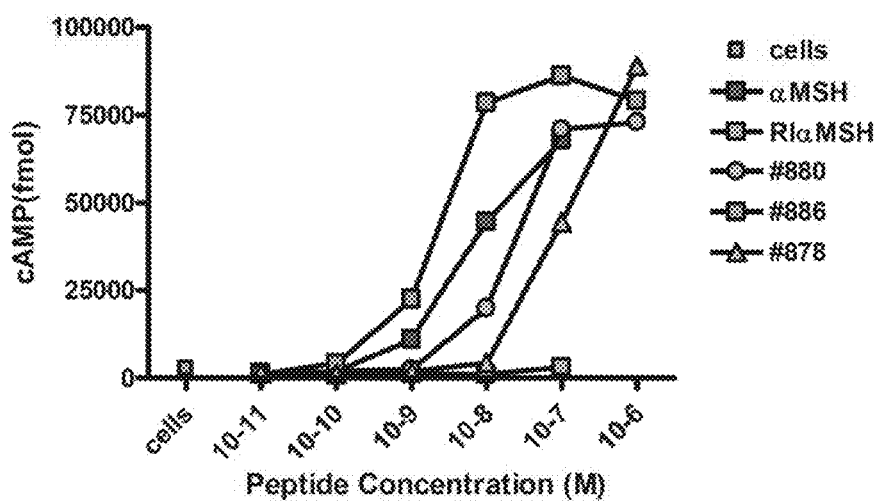
Figure 22D:
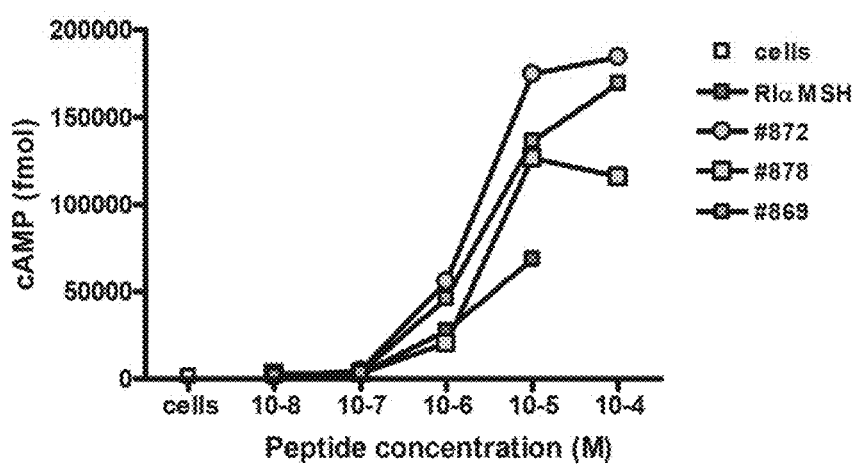

FIGS. 22A-D illustrate the effect of RI α-MSH analogs on cAMP levels in B16 F1 murine melanoma cells. FIG. 22A:

Analogs 890, 891 and 892; FIG. 22B: Analogs 893, 894 and 895; FIG. 22C: Analogs 880, 886 and 878; and FIG. 22D: Analogs 872, 878 and 869.

DETAILED DESCRIPTION OF THE INVENTION

Definitions

The α-MSH and MC1R proteins and nucleic acids of the present methods are not limited to a particular source or species. Thus, the proteins and nucleic acids can be isolated or recombinant.

α-Melanocyte-stimulating hormone (α-MSH) is a polypeptide comprising the sequence Ser Tyr Ser Met Glu His Phe Arg Trp Gly Lys Pro Val (SEQ ID NO:8) (SYSMEHFRWGKPV). α-MSH has been recently examined for anti-inflammatory and immunomodulatory capabilities. α-MSH originates from intracellular proteolytic cleavage of proopiomelanocortin hormone (POMC). α-MSH neuropeptide has been detected in several organs and is produced by neurons, pituitary, gut, skin, and immune cells. α-MSH has been reported to suppress effector T cell function, induce regulatory T cells and have beneficial effects in autoimmune and transplant models.

"Conjugate" or "conjugate" includes two or more members which are attached, joined, coupled, complexed or otherwise associated with each other. The members may be joined to each other through covalent bonds, ionic bonds, electrostatic, hydrogen boding, van der Waals interactions or physical means.

"Biologically active" moieties include a molecule or compound that elicits or modulates a physiological response. In one aspect, a biologically active compound stimulates melanocortin receptors, preferably MC1-receptors.

By "modulate" and "modulation" is meant that the activity of one or more proteins or protein subunits is up regulated or down regulated, such that expression, level, or activity is greater than or less than that observed in the absence of the modulator. For example, the term "modulate" can mean "inhibit" or "stimulate".

"C-terminal sequence" includes reference to the end of the amino acid chain terminated typically, but not necessarily, by a carboxyl group. The convention for writing peptide sequences is to put the C-terminal end on the right and write the sequence from N- to C-terminus. The C-terminal sequence may comprise 1 to 100 amino acids, preferably 2 to 15 amino acids, and even more preferably 3 to 10 amino acids. The C-terminal sequence may terminate with a carboxyl group or the terminus may be modified by well-known methods in the art to comprise a functional member (e.g. targeting group, retention signal, lipid, and anchor).

The present invention provides a "substantially pure compound". The term "substantially pure compound" is used herein to describe a molecule, such as a polypeptide (e.g., a polypeptide that binds MC1R, or a fragment thereof) that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. The purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

In one embodiment, the phrase "selectively binds" means that a compound or polypeptide made or used in the present invention preferentially binds to one type of receptor over another type of receptor when in the presence of a mixture of two or more receptors (e.g., melanocortin receptors, MC1, MC2, MC3, MC4, MC5 receptors).

"Amino acid" or "amino acid sequence" include an oligopeptide, peptide, polypeptide, or protein sequence, or to a fragment, portion, or subunit of any of these, and to naturally occurring or synthetic molecules. The terms "polypeptide" and "protein" include amino acids joined to each other by peptide bonds or modified peptide bonds, i.e., peptide isosteres, and may contain modified amino acids other than the 20 gene-encoded amino acids. The term "polypeptide" also includes peptides and polypeptide fragments, motifs and the like. Capitalized, single-letter abbreviations of the amino acids refer to the natural L-isomer. Lower case, single-letter abbreviations of the amino acids denotes the D-isomer.

The terms "polypeptide," "peptide," and "protein" are used interchangeably to refer to polymers of amino acids of any length. Peptides and polypeptides can be either entirely composed of synthetic, non-natural analogues of amino acids, or, is a chimeric molecule of partly natural peptide amino acids and partly non-natural analogs of amino acids. In one aspect, a polypeptide is used in a composition, cell system or process of the invention (e.g., a host cell having a plasmid expressing at least one enzyme of the invention). In addition, polypeptide can refer to compounds comprised of polymers of amino acids covalently attached to another functional group (e.g., solubilizing group, a targeting group, PEG, non-amino acid group, or other therapeutic agent).

Amino acids may be abbreviated using the following designation in parentheses: Proline (Pro), Valine (Val), Lysine (Lys), Ornithine (Orn), Norleucine (Nle), Glycine (Gly), Tryptophan (Trp), Alanine (Ala), Phenylalanine (Phe), Arginine (Arg), Histidine (His), Glutamic acid (Glu), Aspartic acid (Asp), Serine (Ser), Methionine (Met), Isoleucine (Ile), Tyrosine (Tyr), Cyclohexylalanine (Cha), 4-fluoro-D-phenylglycine (4-fluoro-D-Phg), 2-thienyl-D-alanine (D-Thi).

"Treatment", "treating", "treat" or "therapy" as used herein refers to administering, to a mammal, agents that are capable of eliciting a prophylactic, curative or other beneficial effect in the individual. Treatment may additionally result in attenuating or ameliorating a disease or symptoms of a disease in a subject.

As used herein, the singular form "a", "an", and "the" includes plural references unless indicated otherwise. For example, "a" target cell includes one or more target cells.

Polypeptide compositions of the invention can contain any combination of non-natural structural components. Individual peptide residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole, thiazole, retroamide, thioamide, or ester (see, e.g., Spatola (1983) in *Chemistry and Biochemistry of Amino Acids, Peptides and Proteins*, Vol. 7, pp. 267-357, "Peptide Backbone Modifications," Marcel Dekker, N.Y., incorporated herein by reference).

Polypeptides used to practice the method of the invention can be modified by either natural processes, such as posttranslational processing (e.g., phosphorylation, acylation, etc), or by chemical modification techniques, and the resulting modified polypeptides. Modifications can occur anywhere in the polypeptide, including the peptide backbone, the amino acid side-chains and the amino or carboxyl terminus. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, PEGylation, proteolytic processing, phosphorylation, prenylation, selenoylation, sulfation, and transfer-RNA mediated addition of amino acids to protein such as arginylation. See, e.g., Creighton, T. E., Proteins—Structure and Molecular Properties 2nd Ed., W.H. Freeman and Company, New York (1993); Posttranslational Covalent Modification of Proteins, B. C. Johnson, Ed., Academic Press, New York, pp. 1-12 (1983), incorporated herein by reference.

Additional Embodiments of Compounds

In some embodiments, the invention provided herein is a substantially pure compound that selectively binds melanocortin 1 receptor (MC1R), said compound comprising a polypeptide (SEQ ID NO:10) having the sequence:

$Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$, wherein $Xaa_1$ is D-Val, D-Ala or D-Lys;
$Xaa_2$ is D-Pro, D-Ala or D-Lys;
$Xaa_3$ is D-Lys, D-Orn, D-Nle, D-Ala or D-Lys;
$Xaa_4$ is Gly, or D-Ala;
$Xaa_5$ is D-Trp, Trp, D-3-benzothienyl-Ala, D-5-hydroxy-Trp, D-5-methoxy-Trp, D-Phe, or D-Ala;
$Xaa_6$ is D-Arg, D-His, or D-Ala;
$Xaa_7$ is D-Cha, D-Phe, Phe, D-4-fluoro-Phg, D-3-pyridyl-Ala, D-Thi, D-Trp, D-4-nitro-Phe, or D-Ala;
$Xaa_8$ is D-His, His, D-Arg, Phe, or D-Ala;
$Xaa_9$ is D-Glu, D-Asp, D-citrulline, D-Ser, or D-Ala;
$Xaa_{10}$ is D-Met, D-buthionine, D-Ile, or D-Ala;
$Xaa_{11}$ is D-Ser, D-Ile or D-Ala;
$Xaa_{12}$ is D-Tyr, D-Ser, or D-Ala;
$Xaa_{13}$ is D-Ser or D-Ala;

or a pharmaceutically acceptable salt thereof.

In some embodiments, the peptide analogs provided herein selectively binds MC1R and comprise a polypeptide (SEQ ID NO:11) having the sequence: $Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_1$ $Xaa_{12}$ $Xaa_{13}$, wherein $Xaa_1$ is D-Val; $Xaa_2$ is D-Pro; $Xaa_3$ is D-Lys, D-Orn or D-Nle; $Xaa_4$ is Gly; $Xaa_5$ is D-Trp, Trp, D-3-benzothienyl-Ala, D-5-hydroxy-Trp, D-5-methoxy-Trp, or D-Phe; $Xaa_6$ is D-Arg or D-His; $Xaa_7$ is D-Cha, D-Phe, Phe, D-4-fluoro-Phg, D-3-pyridyl-Ala, D-Thi, D-Trp, or D-4-nitro-Phe; $Xaa_8$ is D-His, His, D-Arg, Phe, or D-Ala; $Xaa_9$ is D-Glu, D-Asp, D-citrulline or D-Ser; $Xaa_{10}$ is D-Met, D-buthionine or D-Ile; $Xaa_{11}$ is D-Ser or D-Ile; $Xaa_{12}$ is D-Tyr or D-Ser; $Xaa_{13}$ is D-Ser; wherein no more than one $Xaa_{1-13}$ is an L-amino acid, or a pharmaceutically acceptable salt thereof.

In other embodiments, the peptide analogs provided herein comprise a polypeptide (SEQ ID NO:12) having the sequence: $Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$, wherein $Xaa_1$ is D-Val; $Xaa_2$ is D-Pro; $Xaa_3$ is D-Lys, D-Orn or D-Nle; $Xaa_4$ is Gly; $Xaa_5$ is D-Trp or Trp; $Xaa_6$ is D-Arg; $Xaa_7$ is D-Cha, D-Phe, Phe or D-Thi; $Xaa_8$ is D-His or His; $Xaa_9$ is D-Glu or D-Ser; $Xaa_{10}$ is D-Met, D-buthionine or D-Ile; $Xaa_{11}$ is D-Ser or D-Ile; $Xaa_{12}$ is D-Tyr or D-Ser; $Xaa_{13}$ is D-Ser; wherein no more than one $Xaa_{1-13}$ is an L-amino acid, or a pharmaceutically acceptable salt thereof.

The compounds provided herein comprise peptide analogs of α-Melanocortin Simulating Hormone (α-MSH).

In one alternative embodiment, the peptide analogs consist of D-amino acids. In other embodiments, the peptides comprise D amino acids, L amino acids or a mixture of D and L amino acids. In other embodiments, the peptides are comprised of at least 40%, 50%, 60%, 70%, 80%, 90% or 100% D amino acids. The compounds of the invention may also incorporate the following non-limiting examples of non-standard amino acids: D-ornithine, D-norleucine, 3-benzothienyl-D-alanine, 5-hydroxy-D-Trp, 5-methoxy-D-Trp, 4-fluoro-D-phenylglycine (4-fluoro-D-Phg), 3-pyridyl-D-alanine, 2-thienyl-D-alanine (D-Thi), D-cyclohexylalanine (D-Cha), 4-nitro-D-Phe, D-citrulline, α-methyl-D-Met, and D-buthionine.

In some embodiments, the core tetrapeptide is comprised of the amino acid sequence His Phe Arg Trp (variant described in SEQ ID NO:1) or Trp Arg Phe His (variant described in SEQ ID NO:2), preferably in the D-amino acid configuration. In another embodiment, the core tetrapeptide is comprised of the amino acid sequence His D-Cha Arg Trp (variant described in SEQ ID NO:1) or Trp Arg D-Cha His (variant described in SEQ ID NO:2), preferably in the D-amino acid configuration. In some embodiments, the core tetrapeptide is comprised of 4 D-amino acids. In other embodiments, the core tetrapeptide has at least one non-standard amino acid.

The compounds provided herein can be synthetic or recombinant. The compounds of the invention may be manufactured by conventional chemical techniques known in the art. Methods of solid phase synthesis are explained in published literature, such as, *Solid Phase Peptide Synthesis: A Practical Approach* (E. Atherton, et al. 1989). The compounds of the invention may also be manufactured by conventional molecular biological techniques known in the art. Within this application, unless otherwise stated, definitions of the terms and illustration of the techniques of this application may be found in any of several well-known references such as: Sambrook, J., et al., *Molecular Cloning: A Laboratory Manual*, Cold Spring Harbor Laboratory Press (1989); Goeddel, D., ed., *Gene Expression Technology, Methods in Enzymology*, 185, Academic Press, San Diego, Calif. (1991); "Guide to Protein Purification" in Deutshcer, M. P., ed., *Methods in Enzymology*, Academic Press, San Diego, Calif. (1989); Innis, et al., *PCR Protocols: A Guide to Methods and Applications*, Academic Press, San Diego, Calif. (1990); Freshney, R. I., *Culture of Animal Cells: A Manual of Basic Technique*, 2nd Ed., Alan Liss, Inc. New York, N.Y. (1987); Murray, E. J., ed., *Gene Transfer and Expression Protocols*, pp. 109-128, The Humana Press Inc., Clifton, N.J. and Lewin, B., *Genes VI*, Oxford University Press, New York (1997). All of the cited references are fully incorporated herein by reference.

In some embodiments, the peptide analogs provided herein selectively bind or activate melanocortin 1 receptor (MC1R). Any suitable assay can be employed to measure the binding or activation of MC1R. For example, cAMP induction in vitro can be used to assess MC1R activation. The in vitro assessment can indicate activation in vivo. Additional embodiments of this invention comprise any polypeptide selective for MC1-receptors. Identification of a selective MC1-receptor compound may be determined by an appropriate screening assay. A non-limiting example of a MC1-receptor binding assay is disclosed in Example 4. In some embodiments, preferable MC1-receptors comprise a melanocortin 1 receptor from homo sapiens (GenBank Accession No: NP_002377).

Further embodiments of the invention are directed to compounds that modulate cAMP, nitric oxide (NO), TNF-α, TNF-α mRNA, IL-10 mRNA, IL-10, IFNγ, IL-6, IL-12 and/or MCP-1 levels. In some embodiments, the compounds increase cAMP levels. In other embodiments, the compounds are directed to the decrease or inhibition of levels of nitric oxide (NO), TNF-α, TNF-α mRNA, IL-10 mRNA, IL-10, IFNγ, IL-6, IL-12 and/or MCP-1. The identity of compounds that modulate abovementioned levels may be determined through screening assays. Acceptable assays known in the art can be used to measure the abovementioned levels. Non-limiting examples of assays for identifying compounds that exhibit desirable modulation of these levels are disclosed in the examples.

In some embodiments, the compounds of this invention may modulate immune response and inflammation by an alternative mechanism of action and is not limited to the mechanisms disclosed herein.

In some embodiments, the peptides provided herein have improved plasma stability and resistance to protease degradation. Plasma stability and resistance to protease degradation can be assessed by any suitable method. A non-limiting example has been disclosed in Example 19. The in vitro assessment can indicate performance, improved resistance and a longer half-life in vivo.

The methods provided herein can be practiced in vivo, ex vivo or in vitro.

PEGylated Peptides

In some embodiments, the peptides are modified to enhance the half-life of the peptide. In some embodiments, the peptide is PEGylated. In some embodiments, PEGylated peptides are directed to peptides covalently attached or conjugated to one or more polyethylene glycol (PEG) polymer chains. PEG polymer chains may include modified, functionalized or otherwise derivatized PEG chains. In another embodiment, the PEG polymer chain may have at least one or more branch points. In some preferred embodiments, PEG polymer chains and the corresponding PEGylated peptide are water soluble, are highly mobile in solution, lack toxicity and immunogenicity, have ready clearance from the body and may have altered distribution in the body. In some preferred embodiments, the pharmacokinetic nature of the PEGylated peptide is modulated by the type of PEG chain. Strategies and methods for the preparation of PEGylated peptides are carried out by methods known in the art (G. Pasuta and F. M. Veronese (2007) "Polymer-drug conjugation, recent achievements and general strategies" *Progress in Polymer Science* 32(8-9): 933-961, incorporated herein by reference). First and second generation PEGylation of protein processes may be found in the art.

A non-limiting example of PEGylation comprises the first step of the suitable functionalization of the PEG polymer at one or both terminals (for linear PEGs). PEGs that are activated at each terminus with the same reactive moiety is known as "homobifunctional", where as if the functional groups present are different, then the PEG derivative is referred as "heterobifunctional" or "heterofunctional." The chemically active or activated derivatives of the PEG polymer are prepared to attach the PEG to the desired molecule. The choice of the suitable functional group for the PEG derivative is based on the type of available reactive group on the molecule that will be coupled to the PEG. Non-limiting examples of reactive amino acids include lysine, cysteine, histidine, arginine, aspartic acid, glutamic acid, serine, threonine and tyrosine. The N-terminal amino group and the C-terminal carboxylic acid can also be used.

Other heterobifunctional PEGs for conjugation: These heterobifunctional PEGs are very much useful in linking two entities, where a hydrophilic, flexible and biocompatible spacer is needed. Preferred end groups for heterobifunctional PEGs are maleimide, vinyl sulphones, pyridyl disulphide, amine, carboxylic acids and N-hydroxysuccinimide (NHS) esters.

In some embodiments of the invention, the PEGylated peptide may have a molecular weight range between 0.2 kDa-100 kDa. In some preferred embodiments of the invention, the PEGylated peptide may have a molecular weight range between 0.2 kDa-40 kDa. In some preferred embodiments of the invention, the PEGylated peptide may have a molecular weight range between 0.2 kDa-15 kDa. In other embodiments, the preferred average molecular weight (in Da; as determined by size exclusion chromatography) for commercially available PEGs, can be selected from <1 k, 2 k, 3.5 k, 5 k, 10 k, 20 k, 30 k, 40 k, and above but can be any MW depending upon the pharmacokinetics desired. For example, lower molecular weight heterobifunctional PEGs which may be used as linkers and lower molecular weight PEGs may be used to improve peptide solubility. The PEG also can be multi-arm, forked, or branched.

In some embodiments, the peptide is conjugated to targeting molecules or function as a targeting molecule, wherein the targeting molecule preferentially associates with a desired receptor. In some preferred embodiments of the invention the peptide is conjugated to a cytotoxic agent. The term "cytotoxic agent" refers to a substance that inhibits or prevents the expression activity of cells, function of cells and/or causes destruction of cells. The term is intended to include radioactive isotopes chemotherapeutic agents, and toxins such as small molecule toxins or enzymatically active toxins of bacterial, fungal, plant or animal origin, including fragments and/or variants thereof. Non-limiting examples of the cytotoxic agent include maytansine, dolastatin and its analogs including tasidotin and auristatin. In other embodiments of the invention, non-limiting examples of cytotoxic agents include, but are not limited to maytansinoids, yttrium, bismuth, ricin, ricin A-chain, saporin, doxorubicin, daunorubicin, taxol, ethidium bromide, mitomycin, etoposide, tenoposide, vincristine, vinblastine, colchicine, dihydroxy anthracin dione, actinomycin, diphtheria toxin subunit A, truncated Pseudomonas exotoxin (PE) A, PE40, abrin, abrin A chain, modeccin A chain, alpha-sarcin, gelonin, mitogellin, restrictocin, phenomycin, enomycin, curicin, crotin, calicheamicin, sapaonaria officinalis inhibitor, and glucocorticoid and other chemotherapeutic agents, as well as radioisotopes such as $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu. Antibodies may also be conjugated to an anti-cancer pro-drug activating enzyme capable of converting the pro-drug to its active form.

The peptide may be linked either directly or indirectly to the cytotoxic or targeting agent by any method presently known in the art. In some preferred embodiments of the invention, the peptide is tethered to the cytotoxic agent or targeting agent by one or more linkers to form a conjugate, so long as the inclusion of the linker does not substantially impede the function, binding, toxicity or inclusion of the peptide or conjugated agent.

Non-limiting examples of linkers include ionic and covalent bonds and any other sufficiently stable association, whereby the targeted agent will be internalized by a cell to which the conjugated is targeted. The linker moiety is selected depending upon the properties desired. Considerations of linker selection may include the relief or decrease of steric hindrance caused by proximity of the conjugated elements, the alteration of other properties of the conjugate, such as the specificity, toxicity, solubility, serum stability and/or intracellular availability of the conjugate and/or to increase the flexibility of the linkage. The linker may be any type of linkage and examples are described in U.S. Pat. Nos. 7,166,702 and 5,194,425, both of which are fully incorporated herein by reference.

Linkers and linkages that are suitable for chemically linked conjugates include, but are not limited to, disulfide bonds, thioether bonds, hindered disulfide bonds, and covalent bonds between free reactive groups, such as amine and thiol groups. These bonds are produced using heterobifunctional reagents to produce reactive thiol groups on one or both of the polypeptides and then reacting the thiol groups on one polypeptide with reactive thiol groups or amine groups to which reactive maleimido groups or thiol groups can be attached on the other. Other linkers include, acid cleavable linkers, such as bismaleimidoethoxy propane, acid labile-transferrin conjugates and adipic acid dihydrazide, that would be cleaved in more acidic intracellular compartments; cross linkers that are cleaved upon exposure to UV or visible light and linkers, such as the various domains, such as CH1, CH2, and CH3, from the constant region of human IgG1 (see Batra et al. (1993) *Mol. Immunol.* 30:379-386, incorporated herein by reference).

Chemical linkers and peptide linkers may be inserted by covalently coupling the linker to the peptide and the targeting or cytotoxic agent. The heterobifunctional agents, described below, may be used to effect such covalent coupling.

Heterobifunctional Cross-Linking Reagents

Numerous heterobifunctional cross-linking reagents that are used to form covalent bonds between amino groups and thiol groups and to introduce thiol groups into proteins, are known to those of skill in this art (see, e.g., the PIERCE CATALOG, Immuno Technology Catalog & Handbook, 1992-1993, which describes the preparation of and use of such reagents and provides a commercial source for such reagents; see also Cumber et al. (1992) *Bioconjugate Chem.* 3':397-401; Thorpe et al. (1987) *Cancer Res.* 47:5924-5931; Gordon et al. (1987) *Proc. Natl. Acad. Sci. USA* 84:308-312; Walden et al. (1986) *J. Mol. Cell Immunol.* 2:191-197; Carlsson et al. (1978) *Biochem. J.* 173: 723-737; Mahan et al. (1987) *Anal. Biochem.* 162:163-170; Wawryznaczak et al. (1992) *Br. J. Cancer* 66:361-366; Fattom et al. (1992) *Infection & Immun.* 60:584-589). All of the cited references are fully incorporated herein by reference. These reagents may be used to form covalent bonds between the targeting agent, the chemokine, and the targeted agent. These reagents include, but are not limited to: N-succinimidyl-3-(2-pyridyidithio)propionate (SPDP; disulfide linker); sulfosuccinimidyl 6-[3-(2-pyridyldithio)propionamido]hexanoate (sulfo-LC-SPDP); succinimidyloxycarbonyl-α-methyl benzyl thiosulfate (SMBT, hindered disulfate linker); succinimidyl 6-[3-(2-pyridyidithio)propionamido]hexanoate (LC-SPDP); sulfosuccinimidyl 4-(N-maleimidomethyl)cyclohexane-1-carboxylate (sulfo-SMCC); succinimidyl 3-(2-pyridyldithio)butyrate (SPDB; hindered disulfide bond linker); sulfosuccinimidyl 2-(7-azido-4-methylcoumarin-3-acetamide) ethyl-1,3-dithiopropionate (SAED); sulfo-succinimidyl 7-azido-4-methylcoumarin-3-acetate (SAMCA); sulfosuccinimidyl 6-[alpha-methyl-alpha-(2-pyridyidithio)toluamido]hexanoate (sulfo-LC-SMPT); 1,4-di-[3'-(2'-pyridyidithio)propionamido]butane (DPDPB); 4-succinimidyloxycarbonyl-α-methyl-α-(2-pyridylthio) toluene (SMPT, hindered disulfate linker); sulfosuccinimidyl6[α-methyl-α-(2-pyridyldithio)toluamido]hexanoate (sulfo-LC-SMPT); m-maleimidobenzoyl-N-hydroxysuccinimide ester (MBS); m-maleimidobenzoyl-N-hydroxysulfosuccinimide ester (sulfo-MBS); N-succinimidyl(4-iodoacetyl)aminobenzoate (SIAB; thioether linker); sulfosuccinimidyl(4-iodoacetyl)amino benzoate (sulfo-SIAB); succinimidyl-4-(p-maleimidophenyl)butyrate (SMPB); sulfosuccinimidyl-4-(p-maleimidophenyl)butyrate (sulfo-SMPB); azidobenzoyl hydrazide (ABH).

Other heterobifunctional cleavable cross-linkers include, N-succinimidyl (4-iodoacetyl)-aminobenzoate; sulfosuccinimidyl (4-iodoacetyl)-aminobenzoate; 4-succinimidyl-oxycarbonyl-a-(2-pyridyldithio)-toluene; sulfosuccinimidyl-6-[a-methyl-a-(pyridyldithiol)-toluamido]hexanoate; N-succinimidyl-3-(-2-pyridyidithio)-proprionate; succinimidyl 6[3(-(-2-pyridyldithio)-proprionamido]hexanoate; sulfosuccinimidyl 6[3(-(-2-pyridyldithio)-propionamido] hexanoate; 3-(2-pyridyidithio)-propionyl hydrazide, Ellman's reagent, dichlorotriazinic acid, 5-(2-thiopyridyl)-L-cysteine. Further exemplary bifunctional linking compounds are disclosed in U.S. Pat. Nos. 5,349,066, 5,618,528, 4,569,789, 4,952,394 and 5,137,877, all of which are fully incorporated herein by reference.

Acid Cleavable, Photocleavable and Heat Sensitive Linkers

Acid cleavable linkers, photocleavable and heat sensitive linkers may also be used, particularly where it may be necessary to cleave the targeted agent to permit it to be more readily accessible to reaction. Acid cleavable linkers include, but are not limited to, bismaleimidoethoxy propane; and adipic acid dihydrazide linkers (see, e.g., Fattom et al. (1992) *Infection & Immun.* 60:584-589, incorporated herein by reference) and acid labile transferrin conjugates that contain a sufficient portion of transferrin to permit entry into the intracellular transferrin cycling pathway (see, e.g., Welhöner et al. (1991) *J. Biol. Chem.* 266:4309-4314, incorporated herein by reference).

Photocleavable linkers are linkers that are cleaved upon exposure to light (see, e.g., Goldmacher et al. (1992) *Bioconj. Chem.* 3:104-107, which linkers are herein incorporated by reference), thereby releasing the targeted agent upon exposure to light. Photocleavable linkers that are cleaved upon exposure to light are known (see, e.g., Hazum et al. (1981) in *Pept., Proc. Eur. Pept. Symp.*, 16th, Brunfeldt, K (Ed), pp. 105-110, which describes the use of a nitrobenzyl group as a photocleavable protective group for cysteine; Yen et al. (1989) *Makromol. Chem.* 190:69-82, which describes water soluble photocleavable copolymers, including hydroxypropylmethacrylamide copolymer, glycine copolymer, fluorescein copolymer and methylrhodamine copolymer; Goldmacher et al. (1992) *Bioconj. Chem.* 3:104-107, which describes a cross-linker and reagent that undergoes photolytic degradation upon exposure to near UV light (350 nm); and Senter et al. (1985) *Photochem. Photobiol.* 42:231-237, which describes nitrobenzyloxycarbonyl chloride cross linking reagents that produce photocleavable linkages), thereby releasing the targeted agent upon exposure to light. All of the cited references are fully incorporated herein by reference. Such linkers would have particular use in treating dermatological or ophthalmic conditions that can be exposed to light using fiber optics. After administration of the conjugate, the eye or skin or other body part can be exposed to light, resulting in release of the targeted moiety from the conjugate. Such photocleavable linkers are useful in connection with diagnostic protocols in which it is desirable to remove the targeting agent to permit rapid clearance from the body of the animal.

Other Linkers for Chemical Conjugation

Other linkers, include trityl linkers, particularly, derivatized trityl groups to generate a genus of conjugates that provide for release of therapeutic agents at various degrees of acidity or alkalinity. The flexibility thus afforded by the ability to pre-select the pH range at which the therapeutic agent will be released allows selection of a linker based on the known physiological differences between tissues in need of delivery of a therapeutic agent (see, e.g., U.S. Pat. No. 5,612,474, incorporated herein by reference). For example, the acidity of tumor tissues appears to be lower than that of normal tissues.

Peptide Linkers

The linker moieties can be peptides. Peptide linkers can be employed in the conjugate. The peptide linker typically a has from about 2 to about 60 amino acid residues, for example from about 5 to about 40, or from about 10 to about 30 amino acid residues. The length selected will depend upon factors, such as the use for which the linker is included.

The linker moiety can be a flexible spacer amino acid sequence, such as those known in single-chain antibody research. Examples of such known linker moieties include, but are not limited to, GGGGS (SEQ ID NO:13), (GGGGS)n (SEQ ID NO:13), GKSSGSGSESKS (SEQ ID NO:14), GSTSGSGKSSEGKG (SEQ ID NO:15), GSTSGS-GKSSEGSGSTKG (SEQ ID NO:16), GSTSGS-GKSSEGKG (SEQ ID NO:17), GSTSGSGKPGSGEG-STKG (SEQ ID NO:18), EGKSSGSGSESKEF (SEQ ID NO:19), SRSSG (SEQ ID NO:20), SGSSC (SEQ ID NO:21). A Diphtheria toxin trypsin sensitive linker having the sequence AMGRSGGGCAGNRVGSSLSCGGLN-LQAM (SEQ ID NO:22) is also useful.

Additional linking moieties are described, for example, in Huston et al., *Proc. Natl. Acad. Sci. U.S.A.* 85:5879-5883, 1988; Whitlow, M., et al., *Protein Engin.* 6:989-995, 1993; Newton et al., *Biochemistry* 35:545-553, 1996; A. J. Cumber et al., *Bioconj. Chem.* 3:397-401, 1992; Ladurner et al., *J. Mol. Biol.* 273:330-337, 1997; and U.S. Pat. No. 4,894,443, all of which publications are incorporated herein by reference.

Other linkers include, but are not limited to: enzyme substrates, such as cathepsin B substrate, cathepsin D substrate, trypsin substrate, thrombin substrate, subtilisin substrate, Factor Xa substrate, and enterokinase substrate; linkers that increase solubility, flexibility, and/or intracellular cleavability include linkers, such as (glymser)n and (sermg-ly)n, (see, e.g., PCT Pub. No. WO 96/06641, incorporated herein by reference, which provides exemplary linkers for use in conjugates). In some embodiments, several linkers may be included in order to take advantage of desired properties of each linker.

Preparation of Conjugates

Conjugates with linked targeted agents can be prepared either by chemical conjugation, recombinant DNA technology, or combinations of recombinant expression and chemical conjugation. The peptide of the invention and the cytotoxic or targeting agent may be linked in any orientation and more than one targeting agent and/or targeted agent may be present in a conjugate.

In some preferred embodiments of the invention, the cytotoxic agent is tethered to the peptide by means of a hydrophilic and biocompatible spacer polymer, including a short alkyl chain, polysialic or hyaluronic acid, a polypeptide or a PEG. In some preferred embodiments of the invention, the cytotoxic agent is conjugated through a cleavable linker, e.g., a disulfide linkage or peptide containing a sequence cleavable by lysosomal proteases such as cathepsins. In some preferred embodiments of the invention, the spacer is attached either to the N- or C-terminus of the peptide.

Formulations

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Pharmaceutical formulations can be prepared according to any method known to the art for the manufacture of pharmaceuticals. Such formulations can contain sweetening agents, flavoring agents, coloring agents and preserving agents. A formulation can be admixed with nontoxic pharmaceutically acceptable excipients which are suitable for manufacture. Such an "excipient" generally refers to a substantially inert material that is nontoxic and does not interact with other components of the composition in a deleterious manner. Pharmaceutically acceptable excipients include, but are not limited to, liquids such as water, buffered saline, polyethylene glycol, hyaluronic, glycerol and ethanol. Pharmaceutically acceptable salts can be included therein, for example, mineral acid salts such as trifluoroacetate, hydrochlorides, hydrobromides, phosphates, sulphates, and the like; and the salts of organic acids such as acetates, propionates, malonates, benzoates, and the like.

The therapeutic agent may be administered in a medicament or pharmaceutical composition suitable for delivery. Formulations may comprise one or more diluents, emulsifiers, preservatives, buffers, excipients, etc., and may be provided in such forms as lyophilized powders, sprays, creams, lotions, gels, on patches, in implants, etc. Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragée cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate.

Aqueous suspensions can contain an active agent (e.g., a chimeric polypeptide or peptidomimetic of the invention) in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil-based pharmaceuticals are useful for administration of hydrophobic active agents of the invention. Oil-based suspensions can be formulated by suspending an active agent (e.g., a chimeric composition of the invention) in a vegetable oil, such as arachis oil, olive oil, sesame oil or coconut oil, or in a mineral oil such as liquid paraffin; or a mixture of these. See e.g., U.S. Pat. No. 5,716,928, incorporated herein by reference, describing using essential oils or essential oil components for increasing bioavailability and reducing inter- and intra-individual variability of orally administered hydrophobic pharmaceutical compounds (see also U.S. Pat. No. 5,858,401, incorporated herein by reference). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) *J. Pharmacol. Exp. Ther.* 281:93-102, incorporated herein by reference. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

It is also contemplated that a composition or medicament comprising the therapeutic agent can contain a pharmaceutically acceptable carrier that serves as a stabilizer, particularly for peptide, protein, polynucleotide or other like agents. Examples of suitable carriers that also act as stabilizers for peptides include, without limitation, pharmaceutical grades of dextrose, sucrose, lactose, trehalose, mannitol, sorbitol, inositol, dextran, and the like. Other suitable carriers include, again without limitation, starch, cellulose, sodium or calcium phosphates, citric acid, tartaric acid, glycine, high molecular weight polyethylene glycols (PEGs), and combination thereof. It may also be useful to employ a charged lipid and/or detergent. Suitable charged lipids include, without limitation, phosphatidylcholines (lecithin), and the like. Detergents will typically be a non-ionic, anionic, cationic or amphoteric surfactant. Examples of suitable surfactants include, for example, TERGITOL® and TRITON® surfactants (Union Carbide Chemicals and Plastics, Danbury, Conn.), polyoxyethylenesorbitans, for example, TWEEN® surfactants (Atlas Chemical Industries, Wilmington, Del.), polyoxyethylene ethers, for example Brij, pharmaceutically acceptable fatty acid esters, for example, lauryl sulfate and salts thereof (SDS), and like materials. A thorough discussion of pharmaceutically acceptable excipients, carriers, stabilizers and other auxiliary substances is available in *Remington's Pharmaceutical Sciences* (Mack Pub. Co., N.J. 1991), incorporated herein by reference.

Pharmaceutical compositions of the present invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient, or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the compounds of the present invention may be ensured by the inclusion of various antibacterial and antifungal agents, for example, paraben, chlorobutanol, phenol, sorbic acid, and the like. It may also be desirable to include isotonic agents, such as sugars, sodium chloride, phosphate buffered saline, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

In the methods of the invention, the pharmaceutical compounds can also be delivered as microspheres for slow release in the body. For example, microspheres can be administered via intradermal injection of drug which slowly release subcutaneously; see Rao (1995) *J. Biomater Sci. Polym. Ed.* 7:623-645; as biodegradable and injectable gel formulations, see, e.g., Gao (1995) *Pharm. Res.* 12:857-863 (1995); or, as microspheres for oral administration, see, e.g., Eyles (1997) *J. Pharm. Pharmacol.* 49:669-674. All of the cited references are fully incorporated herein by reference Injectable depot forms are made by forming microencapsule matrices of the compounds of the present invention in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The polypeptide may be administered on its own or in combination with another therapeutic compound. In particular, the polypeptide may be administered in conjunction with a therapeutic compound used to treat melanoma, inflammation or an autoimmune disease in the mammal. The polypeptide and additional therapeutic compound may be formulated in the same or different compositions. The polypeptide may be administered simultaneously, sequentially or separately from the additional therapeutic compound.

Dosage

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. When the compounds of the present invention are administered as pharmaceuticals, to humans and animals, they can be given per se or as a pharmaceutical composition containing, for example, 0.1 to 99% of active ingredient, more preferably, 10 to 30%, in combination with a pharmaceutically acceptable carrier.

The selected dosage level will depend upon a variety of factors including the activity of the particular compound of the present invention employed, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of the present invention for a patient, when used for the indicated effects, will have a non-limiting range from about 1 mcg to about 5 mg per kilogram of body weight per hour. In other embodiments, the dose will have a non-limiting range from about 5 mcg to about 2.5 mg per kilogram of body weight per hour. In further embodiments, the dose will have a non-limiting range from about 5 mcg to about 1 mg per kilogram of body weight per hour.

If desired, the effective daily dose of the active compound may be administered as two, three, four, five, six or more sub-doses administered separately at appropriate intervals throughout the day, optionally, in unit dosage forms. In one embodiment, the compound is administered as one dose per day. In further embodiments, the compound is administered continuously, as through intravenous or other routes. In other embodiments, the compound is administered less frequently than daily, such as weekly or less.

While it is possible for a compound of the present invention to be administered alone, it is preferable to administer the compound as a pharmaceutical formulation (composition).

The subject receiving this treatment is any animal in need, including primates, in particular humans, and other mammals such as rabbits, equines, cattle such as bovine, swine, goat and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy thus includes sequential, simultaneous and separate administration of the active compound in a way that the therapeutical effects of the first administered one is not entirely disappeared when the subsequent is administered.

Possible Routes of Administration for Disclosed Compounds

These compounds may be administered to humans and other animals for therapy by any suitable route of administration. As used herein, the term "route" of administration is intended to include, but is not limited to subcutaneous injection, intravenous injection, intraocular injection, intradermal injection, intramuscular injection, intraperitoneal injection, intratracheal administration, intraadiposal administration, intraarticular administration, intrathecal administration, epidural administration, inhalation, intranasal administration, oral administration, sublingual administration, buccal administration, rectal administration, vaginal administration, intracisternal administration, transdermal administration and topical administration, or administration via local delivery (for example by catheter or stent). The compounds may also be administered or co-administered in slow release dosage forms.

In the methods of the invention, the pharmaceutical compounds can also be administered by in intranasal, intraocular, periocular and intravaginal routes including suppositories, insufflation, powders and aerosol formulations (for examples of steroid inhalants, see Rohatagi (1995) *J. Clin. Pharmacol.* 35:1187-1193; Tjwa (1995) *Ann. Allergy Asthma Immunol.* 75:107-111, incorporated herein by reference). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In the methods of the invention, the pharmaceutical compounds can be delivered transdermally, by a topical route, formulated as applicator sticks, solutions, suspensions, emulsions, gels, creams, ointments, pastes, jellies, powders, and aerosols.

In the methods of the invention, the pharmaceutical compounds can be parenterally administered, such as by intravenous (IV) administration or administration into a body cavity (e.g., the synovial space) or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides.

As described herein, the methods of the present invention may be used alone or in combination with other approaches for the treatment of an autoimmune disease or the other conditions described herein.

The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease or condition, are known as "appropriate for the disease, or condition, being treated".

A combination treatment of the present invention as defined herein may be achieved by way of the simultaneous, sequential or separate administration of the individual components of said treatment.

Therapeutic Applications

Administration of the polynucleotide or a modulatory compound (hereinafter "therapeutic agent") as discussed herein may be either for preventative or therapeutic purpose. When provided preventatively, the therapeutic agent is provided in advance of any symptoms. The preventative administration of the therapeutic agent serves to prevent or attenuate any symptoms. When provided therapeutically, the therapeutic agent is provided at (or shortly after) the onset of a symptom of the disease or disorder. The therapeutic administration of the therapeutic agent serves to attenuate any actual exacerbation of the symptoms.

The individual treated may be any mammal. In one aspect, the mammal is a human. In another aspect, the human has an autoimmune disease or condition. In other aspects, the autoimmune disease or condition is associated with or selected from the group consisting of multiple sclerosis, diabetes type I, aplastic anemia, Grave's disease, coeliac disease, Crohn's disease, lupus, arthritis, osteoarthritis, autoimmune uveitis, autoimmune encephalomyelitis, and myasthenia gravis.

In other aspects, the human has an inflammation disease or condition. In another aspect, the inflammation disease or condition is associated with or selected from the group consisting of inflammatory bowel disease, rheumatoid arthritis, allergy, atherosclerosis, psoriasis, gastritis and ischemic heart disease. In another aspect, the inflammation is associated with brain death, preferably wherein levels of circulating endogenous α-MSH or α-MSH in brain tissue is reduced. In yet another aspect, the therapeutic agent is used to treat a subject with an α-MSH or MC1-receptor mediated disorder or disease.

In another aspect, the present invention is directed towards treatment of a subject with melanoma. In one aspect, the present invention attenuates or ameliorates melanoma in subjects. In yet another aspect, the compounds of the present invention are used in assays for melanoma detection or imaging.

Kits Comprising the Disclosed Compounds

The invention also provides kits for carrying out the therapeutic regimens of the invention. Such kits comprise therapeutically effective amounts of a peptide having specific activity as MC1R modulators, in pharmaceutically acceptable form, alone or in combination with other agents, in pharmaceutically acceptable form. Preferred pharmaceutical forms include peptides in combination with sterile saline, dextrose solution, buffered solution, or other pharmaceutically acceptable sterile fluid. Alternatively, the composition may be lyophilized or desiccated. In this instance, the kit may further comprise a pharmaceutically acceptable solution, preferably sterile, to form a solution for injection purposes. In another embodiment, the kit may further comprise a needle or syringe, preferably packaged in sterile form, for injecting the composition. In other embodiments, the kit further comprises an instruction means for administering the composition to a subject. The instruction means can be a written insert, an audio recording, an audiovisual recording, or any other means of instructing the administration of the composition to a subject. In one embodiment, the kit comprises (i) a first container containing a peptide having MC1R-specific modulatory activity; and (ii) instruction means for use.

Additional Embodiments of Method of Treatment

In some embodiments, the invention provides a method to reduce or inhibit transplant rejection in a subject in need thereof comprising administering to said subject a pharmaceutical composition comprising a pharmaceutically acceptable excipient and an effective amount of at least one of the peptide compounds provided herein. In some embodiments, the invention provides a method to reduce or inhibit an immune response of the subject elicited by transplanted tissue, cells or organ. Non-limiting examples of a transplanted tissue are an allograft in experimental heart transplantation and pancreatic islet cells.

Immunosuppressive Activity in Experimental Autoimmune Encephalomyelitis (EAE) model Novel D-amino acid peptide analogs of α-MSH were generated and evaluated for immune modulatory effects in the experimental autoimmune uveitis (EAU) and experimental autoimmune encephalomyelitis (EAE) models as well as in a lipopolysaccharide (LPS) surrogate inflammatory disease model. Treatment with RI α-MSH analog reduced clinical disease scores and incidence of disease in the EAU model and in a MOG induced EAE mouse model. In addition, TNF-α and IL-10 mRNA expression levels in spleen and lymph node of MOG primed mice was decreased in treated mice. In a LPS induced systemic inflammation model, α-MSH and analog treatment decreased serum cytokine levels. These data indicate that these novel α-MSH analogs have the potential for therapeutic use in inflammation and autoimmune disease.

Materials and Methods

Peptides. α-MSH (SYSMEHFRWGKPV) (SEQ ID NO:8) was purchased from Bachem (King of Prussia, Pa.). A D-amino acid RI α-MSH analog (vpkgwrfhemsys), alanine substituted peptide of RI α-MSH, (Stearyl) HfRW (820), (Ph($CH_2$)$_3$C0) HfRW (819), and RI α-MSH analog 891 [vpkGwr(D-Cha)hsiiss] (SEQ ID NO:5) were synthesized by Genzyme Corporation with a standard solid phase methodology and was purified by reverse phase HPLC. A scrambled D amino acid control peptide (ksrsmgvfpeyh)

was synthesized by Genzyme Corporation. An irrelevant D amino acid control peptide (plykkiikklles) was synthesized by Genzyme Corporation.

Animals. Five to six week old female B10.RIII-H2r mice were purchased from Jackson Laboratories (Bar Harbor, Me.).

Six to eight week old female or male C57BL/6 mice were purchased from Jackson Laboratories (Bar Harbor, Me.). All protocols for animal studies met with approval from the Institutional Animal Care and use Committee (IACUC) at Genzyme Corporation.

EAU induction. Female B 10.RIII were injected subcutaneously at two sites (between shoulder blades and in pelvic region) with a total of 200 μg interphotoreceptor binding protein peptide (IRBP) 161-180 (New England Peptide; Fitchburg, Me.), respectively in 2 mg/ml complete Freund's adjuvant (CFA; Sigma, St. Louis, Mo.) with mycobacterium tuberculosis H37Ra (Difco, Detroit, Mich.).

Eye Scoring. The eyes of mice are dilated using one or two drops of Mydriacyl 1% (Alcon; Humacao, Puerto Rico) and rested in a darkened room for approximately 5 min. Mice are manually restrained and the retinas of both eyes are visualized using an indirect ophthalmoscope with a 78 diopter lens. The eyes are scored for inflammation using a progressive scoring system between 0-5. Score 0: Normal retina. Score 1: Vascular inflammation proximal to the optic nerve. Score 2: <5 inflammatory lesions confined to one quadrant of the eye. Score 3: >5 inflammatory lesions in more than one quadrant of the eye. Score 4: Inflammatory lesions are contiguous. Score 5: Retinal detachment. Whole eyes from mice were harvested and placed in PBS. The eyes were embedded in OCT media for frozen fixation. 5-μm sections were cut through the papillary-optic nerve plane and stained with hematoxylin and eosin.

Binding Studies to Melanocortin Receptors. Binding profiles for α-MSH, RI α-MSH, and scrambled peptide were measured to melanocortin receptors: 1, 3, 4, and 5. Binding was done using a competitive binding assay with (Nle4,D-Phe7) α-MSH (Bachem). Binding analysis was done by Cerep laboratories (Paris, France) with coded samples.

Binding of the peptides was also followed by a competition with $^{125}$I-NDP-MSH for binding the melanocortin receptors 1, 3, 4, and 5 using membrane preparations from HEK293 cell lines. Peptides were mixed with $^{125}$I-(Nle4,D-Phe7)-α-MSH (PerkinElmer, Boston Mass.) in V-bottom 96 well plates in binding buffer (25 mM HEPES pH7, 1.5 mM $CaCl_2$, 1 mM $MgSO_4$, 100 mM NaCl, 0.2% BSA) and mixed with membrane preparations from HEK293 transfected cell lines (Perkin Elmer, Boston Mass.) containing 1-10 fmol receptor for 1 hr at 25° C. (Nle4,D-Phe7)-NDP-MSH (Bachem) at 3 μM was used as a positive control. The mixtures were filtered through 96-well GFC filters (Millipore, Billerica, Mass.), washed 3 times with binding buffer without BSA, dried and counted.

cAMP Measurement. B16-F1 (melanoma cell line) cells from American Type Culture Collection (Manassas, Va.) were seeded into flat bottom 96 well plates at $5\times10^4$/well and cultured overnight in DMEM (Cambrex, Walkersville, Md.) supplemented with 2 mM glutamine, antibiotics (100 U/ml penicillin and 100 U/ml streptomycin) and 10% heat-inactivated fetal bovine serum (Invitrogen, Grand Island, N.Y.). Cells were then treated with native α-MSH (0.01-1000 ng/ml), retro-inverso α-MSH (0.01-1000 ng/ml), or a scrambled D amino acid control peptide (0.01-1000 ng/ml) for 30 min. Cells were lysed and intracellular cAMP levels were measured by an enzyme immunoassay kit (Amersham Biosciences, Piscataway, N.J.). Forskolin (Sigma, St. Louis, Mo.) at 100 μM served as positive controls.

EAE induction and scoring. Female C57BL/6 mice were immunized with an emulsion of MOG35-55 peptide (200 μg/mouse; New England Peptide; Fitchburg, Mass.) in complete Freund's adjuvant (CFA; Sigma, St. Louis, Mo.) containing 0.6 mg Mycobacterium tuberculosis (Difco; Detroit, Mich.). The emulsion was delivered in a volume of 0.2 ml per mouse by subcutaneous injection to two sites. Bordetella pertussis toxin (PTX; Sigma) in PBS was used at a dose of 400 ng/animal via an i.p. administration route and is administered on day 0 and day 3. Mice were monitored daily for paralytic symptoms of EAE. The mice were scored for clinical symptoms using a progressive scoring system between 0-5. Score 0: no disease; Score 1: flaccid tail; Score 2; hind limb weakness; Score 3: hind limb paralysis; Score 4: Front limb weakness/partial paralysis; Score 5; death. Spinal cord and brain were harvested and embedded in paraffin for hematoxylin and eosin staining.

Proliferation Assay. C57BL/6 mouse splenocytes and lymph node cells were cultured in 96 well plates $5\times105$ cells/well. MOG35-55 or OVA 257-264 peptide was added to wells at a concentration of 25 μg/ml. Supernatant was collected at 48 hrs after MOG peptide stimulation. After 3 days in culture cells were pulsed with [3H] thymidine at 1 μCi/well for 8 hrs. Thymidine incorporation was measured by cpm.

Cytokine RNA analyses-RT-QPCR. Total RNA was extracted from tissues with TRIZOL® (Invitrogen, Carlsbad, Calif.). 1 μg of total RNA was reverse transcribed and used in quantitative PCR by using SYBR® green incorporation with reagents from Applied Biosystems (Foster City, Calif.) on an ABI 7900. A cDNA standard was run in each PCR for cytokine targets and message concentrations were normalized to mouse β-actin. Primers used to obtain these data were as follows: mouse TNFα forward-ggcaggtctactttggagtcattgc (SEQ ID NO:27) and reverse-acattcgaggctccagtgaattcgg (SEQ ID NO:28) (1). The sequences for mouse IL-10 primers were forward: tgctatgctgcctgctctta (SEQ ID NO:29) and reverse: tcatttccgataaggcttgg (SEQ ID NO:30) (2). The sequences for mouse β-actin primers were: forward gtgggccgctctaggcaccaa (SEQ ID NO:31) and reverse ctctttgatgtcacgcacgatttc (SEQ ID NO:32) (3).

CBA analysis. Flow cytometric analysis of inflammatory cytokine profiles of mouse serum or cell supernatant were measured using the Cytometric Bead Array Kit (CBA) made by BD Biosciences (San Jose, Calif.). Samples were processed according to the manufacturer's protocol.

mMC1R RNA analyses-RT-QPCR. Total RNA was extracted from tissues with TRIZOL® (Invitrogen, Carlsbad, Calif.). 1 μg of total RNA was reverse transcribed and used in quantitative PCR by using a TAQMAN® kit with reagents from Applied Biosystems (Foster City, Calif.) on an ABI 7900. A cDNA standard was run in each PCR for mMC1R and message concentrations were normalized to Eukaryotic 18S endogenous control (VIC/MGB probe, Applied Biosystems part #4319413E). Primers for mMC1R were as follows: forward CTCTGCCTCGT-CACTTTCTTTCTA (SEQ ID NO:24) and reverse AACAT-GTGGGCATACAGAATCG (SEQ ID NO:25) and probe CCATGCTGGCACTCA (SEQ ID NO:26). These were designed using PRIMER EXPRESS® 3.0 (Applied Biosystems, Foster City, Calif.).

LPS model. Male C57BL/6 mice were challenged with LPS (1 ug/mouse), i.p. After 30 min mice were treated with dexamethasone (2 mg/kg; Sigma), RI-α-MSH analog 891, or RI-α-MSH. At 2 hrs after LPS challenge, mice were bled for serum. Cytokine analysis was measured by flow cytometry with a cytometric bead array kit (BD Biosciences).

Statistical analysis. The results are expressed as the mean±SD. Each experiment was repeated at least twice. To analyze the results a one-way ANOVA and the Tukey multiple comparison test was used.

The following examples are offered to illustrate but not to limit the invention.

Example 1

Immunosuppressive Activity in Experimental Autoimmune Uveitis (EAU) Model

Autoimmune uveitis is an inflammatory disorder of the eye that can lead to pain and vision loss. Steroids and immunosuppressive drugs are currently the only therapeutics for uveitis and often have serious ocular and systemic toxicities. Therefore, safer alternative therapeutics are desired.

EAU is an animal model of human uveitis which affects 2.3 million individuals in the United States. Immunization with interphotoreceptor retinoid binding protein (IRBP) or its peptide fragments or retinal S-antigen (S-Ag) with adjuvant can induce disease in susceptible strains of rodents. The disease involves infiltration of inflammatory cells in the retina of the eye and photoreceptor damage with natural recovery without spontaneous relapse. The adoptive transfer of uveitogenic T cells in syngeneic rodent recipients suggests that uveitis is an organ specific T cell mediated autoimmune disease like many other similar autoimmune diseases such as multiple sclerosis, type 1 diabetes and rheumatoid arthritis.

The ocular microenvironment is an immune privileged site in which mechanisms to maintain immunosuppression are in place to prevent local inflammation. Several neuropeptides that are expressed by neurons in the ocular tissue help to sustain immune privilege in the eye. One of these neuropeptides is α-MSH which is constitutively expressed in the ocular microenvironment at a physiological concentration of 30 pg/ml.

Systemic administration of native α-MSH during the induction of endotoxin-induced uveitis in rats inhibited the number of infiltrating cells and IL-6, TNF-α, MCP-1, MIP-2, and nitric oxide levels in aqueous humor in a dose dependent manner. In a mouse EAU model administration of α-MSH at the peak time of retinal inflammation suppressed the severity of disease. α-MSH can induce T regulatory cells through the melanocortin 5 receptor (MCR-5) on T cells and suppress EAU.

Figure 1A:
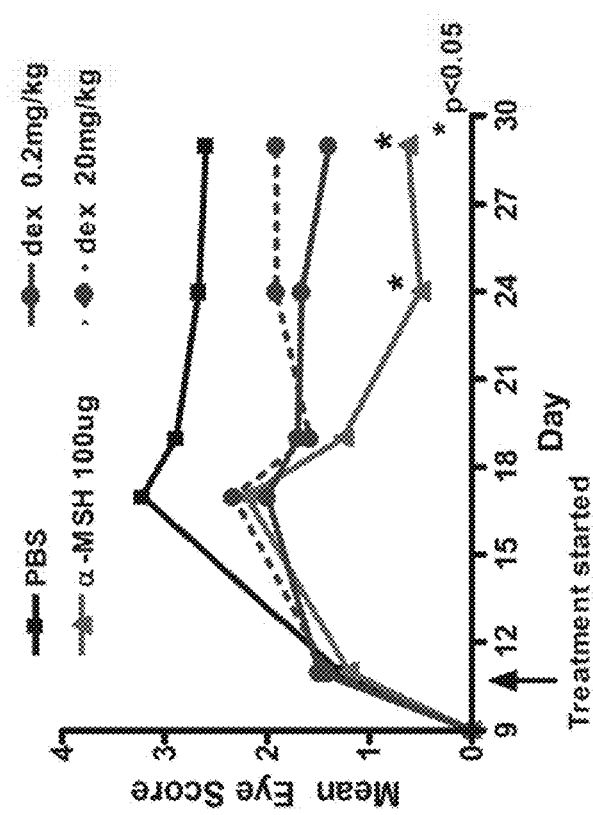
FIGS. 1A-B show reduction of uveitis by native α-MSH.

The efficacy of native α-MSH treatment in the murine posterior uveitis model was evaluated. Uveitis was induced in B10.RIII mice with an injection of IRBP 161-180 and CFA. Onset of disease occurred around day 10 after priming. When eye scores of 2-3 were reached on day 13, mice were administered native α-MSH at 200 µg/mouse, i.v. for 7 consecutive days or left untreated. Since prophylactic treatment may target activities in the priming phase of the disease rather than the effector phase, treatment was initiated when active retinal inflammation was observed. In addition, this treatment strategy better recapitulates clinical application. Mice treated with the α-MSH showed a reduction of mean clinical eye scores throughout the 7 day course of treatment compared with untreated mice (FIG. 1a). α-MSH treated mice showed a maximum mean eye score of 2.83±0.39 on day 13 in comparison to the untreated group of mice which reached a maximum mean eye score of 3.67±0.52 on day 15.

Example 2

Figure 1B:
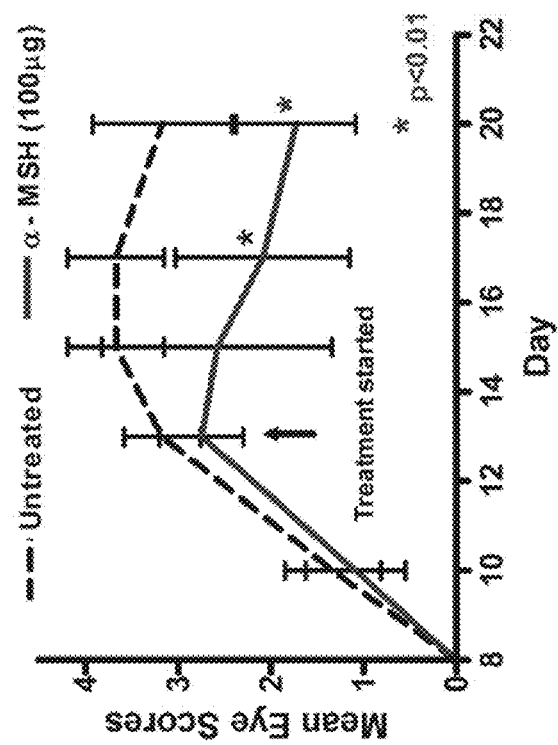

Comparison of Native α-MSH to Dexamethasone in the B10.RIII Experimental Autoimmune Uveitis Model Current forms of therapy for uveitis include corticosteroids and immunosuppressive agents. The efficacy of native α-MSH was compared to a known corticosteroid therapy, dexamethasone. Uveitis was induced in B10.RIII mice with IRBP161-180 and CFA injections. At time of disease onset, when mice reached a clinical eye score of 1, mice were administered daily intraperitoneal injections of native α-MSH (100 µg/mouse), 0.2 mg/kg of dexamethasone, or 2.0 mg/kg of dexamethasone. Mice were treated daily for 21 days. Mice treated with native α-MSH showed a significant reduction of mean clinical eye scores throughout the course of treatment compared with PBS control mice (FIG. 1B). Data showed that daily i.p. administration of native α-MSH suppressed uveitis to a greater degree than the dexamethasone treatment at either the 0.2 mg/kg or 2.0 mg/kg dose.

Example 3

A Novel Retro-Inverso α-MSH Analog Specifically Binds to MCR-1

A novel, stable D-amino acid peptide analog of native α-MSH was synthesized (RI α-MSH) and evaluated for immune modulatory capabilities in vitro and in the experimental autoimmune uveitis (EAU) model. Binding studies indicated that unlike native α-MSH, RI α-MSH binds specifically to the anti-inflammatory α-MSH receptor (MCR-1) but none of the other α-MSH receptors (MCR-3, 4, or 5).

The binding of the RI α-MSH analog to melanocortin receptors (MCR) was analyzed. A competitive binding assay using a MCR panel including MCR 1, 3, 4, and 5 was performed. Binding of the peptides was followed by a competition with $^{125}$I-NDP-MSH as described previously. Native α-MSH bound to MCR 1, 3, 4, and 5. However, unlike native α-MSH, RI α-MSH was found to bind only to MCR-1 which regulates inflammatory responses (Table 1). A scrambled D amino acid control peptide did not bind to any of the melanocortin receptors. The development of an α-MSH analog with specific binding to MCR-1, and the exclusion of MCR-3 and MCR-4 binding, can decrease potential side-effects that native α-MSH produces through binding these receptors.

TABLE 1

| No. | N-terminus | Sequence | C-terminus | Ki (nM, except as noted) MC 1R | MC3R | MC4R | MC5R |
|---|---|---|---|---|---|---|---|
| MSH | Ac | SYSMEHFRWGKPV (SEQ ID NO: 8) | Amide | 0.41 ± 0.14 | 23 | 41 | ~1500 |
| RI-MSH (720e) | Ac | vpkGwrfhemsys (SEQ ID NO: 7) | Amide | 4.6 ± 1.3 | >30 µM | >30 µM | ~25 µM |

TABLE 1-continued

| No. | N-terminus | Sequence | C-terminus | MC1R Ki (nM, except as noted) | MC3R | MC4R | MC5R |
|---|---|---|---|---|---|---|---|
| 804 | Ac | vpkGwrfhemsya (SEQ ID NO: 34) | Amide | nd | | | |
| 805 | Ac | vpkGwrfhemsas (SEQ ID NO: 35) | Amide | | | | |
| 806 | Ac | vpkGwrfhemays (SEQ ID NO: 36) | Amide | | | | |
| 807 | Ac | vpkGwrfheasys (SEQ ID NO: 37) | Amide | 1400 ± 190 | | | |
| 808 | Ac | vpkGwrfhamsys (SEQ ID NO: 38) | Amide | 2.5 | | | |
| 809 | Ac | vpkGwrfaemsys (SEQ ID NO: 39) | Amide | 1200 ± 270 | | | |
| 810 | Ac | vpkGwrahemsys (SEQ ID NO: 40) | Amide | >30 μM | | | |
| 811 | Ac | vpkGwafhemsys (SEQ ID NO: 41) | Amide | 13 ± 7 μM | | | |
| 812 | Ac | vpkGarfhemsys (SEQ ID NO: 42) | Amide | 3 μM | | | |
| 813 | Ac | vpkawrfhemsys (SEQ ID NO: 43) | Amide | | | | |
| 814 | Ac | vpaGwrfhemsys (SEQ ID NO: 44) | Amide | | | | |
| 815 | Ac | vakGwrfhemsys (SEQ ID NO: 45) | Amide | | | | |
| 816 | Ac | apkGwrfhemsys (SEQ ID NO: 46) | Amide | | | | |
| 817 | Ac | aaaGwrfhemsys (SEQ ID NO: 47) | Amide | | | | |
| 818 | Ac | kkkGwrfhemsys (SEQ ID NO: 48) | Amide | | | | |
| 819 | (Ph(CH$_2$)$_3$CO) | HfRW (SEQ ID NO: 49) | Amide | 0.07 | 277 | 27 | ~3000 |
| 820 | Stearyl | Hf RW (SEQ ID NO: 49) | Amide | 1.3 | 1371 | 390 | 860 |
| 847 | H2N | vpkGwrfh (SEQ ID NO: 50) | (CH$_2$)$_3$Phenyl) | 104 ± 72 | | | |
| 847int | H2N | vpkGwrfh (SEQ ID NO: 50) | OH | 150 | | | |
| 857 | Ac | vp(D-Ornithine)Gwrfhemsys (SEQ ID NO: 51) | Amide | 3.0 | | | |
| 858 | Ac | vp(D-Norleucine)Gwrfhemsys (SEQ ID NO: 52) | Amide | 18 | | | |
| 859 | Ac | vpkG(3-benzothienyl-D-Alanine)rfhemsys (SEQ ID NO: 53) | Amide | 206 | | | |
| 860 | Ac | vpkG(5-hydroxy-D-Trp)rfhemsys (SEQ ID NO: 54) | Amide | 96 | | | |
| 861 | Ac | vpkG(5-methoxy-D-Trp)rfhemsys (SEQ ID NO: 55) | Amide | 75 | | | |

TABLE 1-continued

| No. | N-terminus | Sequence | C-terminus | MC 1R | MC3R | MC4R | MC5R |
|---|---|---|---|---|---|---|---|
| 862-b | Ac | vpkGfrfhemsys (SEQ ID NO: 56) | Amide | 128 | | | |
| 863 | Ac | vpkGwqfhemsys (SEQ ID NO: 57) | Amide | >100 µM | | | |
| 864 | Ac | vpkGwnfhemsys (SEQ ID NO: 58) | Amide | >30 µM | | | |
| 865 | Ac | vpkGwhfhemsys (SEQ ID NO: 59) | Amide | 2300 | | | |
| 866 | Ac | vpkGwr(4-fluoro-D-phenylglycine)hemsys (SEQ ID NO: 60) | Amide | >30 µM | | | |
| 867 | Ac | vpkGwr(3-pyridyl-D-Alanine)hemsys (SEQ ID NO: 61) | Amide | 480 | | | |
| 868 | Ac | vpkGwr(2-thienyl-D-Alanine)hemsys (SEQ ID NO: 62) | Amide | 5.4 | | | |
| 869 | Ac | vpkGwr(D-Cha)hemsys (SEQ ID NO: 63) | Amide | 2.2 ± 0.44 | >30 µM | >10 µM | ~25 µM |
| 870 | Ac | vpkGwrwhemsys (SEQ ID NO: 64) | Amide | ~2.5 µM | | | |
| 871 | Ac | vpkGwr(4-Nitro-D-Phe)hemsys (SEQ ID NO: 65) | Amide | 324 | | | |
| 872 | Ac | vpkGwrfremsys (SEQ ID NO: 66) | Amide | 13.5 | | | |
| 873 | Ac | vpkGwrfwemsys (SEQ ID NO: 67) | Amide | 1900 | | | |
| 874 | Ac | vpkGwrffemsys (SEQ ID NO: 68) | Amide | >100 µM | | | |
| 875 | Ac | vpkGwrfhdmsys (SEQ ID NO: 69) | Amide | 400 | | | |
| 876 | Ac | vpkGwrfh(D-Citrulline)msys (SEQ ID NO: 70) | Amide | nd | | | |
| 877 | Ac | vpkGwrfhe(α-methyl-D-Met)sys (SEQ ID NO: 71) | Amide | 282 | | | |
| 878 | Ac | vpkGwrfhe(D-buthionine)sys (SEQ ID NO: 72) | Amide | 2.3 ± 0.8 | ~40 µM | >30 µM | ~30 µM |
| 879 | Ac | vpkGwrfheksys (SEQ ID NO: 73) | Amide | 832 | | | |
| 880 | Ac | vpkGwrFhsiiss (SEQ ID NO: 4) | Amide | 1.8 ± 0.5 | ~18 µM | ~10 µM | >30 µM |
| 881 | Ac | wrFh (SEQ ID NO: 74) | C$_3$-Phenyl | >10 µM | | | |
| 882 | Ac | wrFh (SEQ ID NO: 74) | (1,6-diamino-hexane)stearyl | 120 | | | |
| 883 | Ac | wrFh (SEQ ID NO: 74) | Amide | >100 µM | | | |
| 884 | Ac | vpkGwrFhemsys (SEQ ID NO: 75) | Amide | 72 | >30 µM | ~30 µM | >30 µM |
| 886 | Ac | vpkgwrfhsiiss (SEQ ID NO: 76) | Amide | 1.0 ± 0.43 | ~19 µM | ~10 µM | ~20 µM |

TABLE 1-continued

| No. | N-terminus | Sequence | C-terminus | MC 1R | MC3R | MC4R | MC5R |
|-----|------------|----------|------------|-------|------|------|------|
| 890 | Ac | vpkGwr(D-Cha)he(d-Buthionine)sys (SEQ ID NO: 77) | Amide | 1.9 ± 0.01 | ~15 µM | ~14 µM | ~4.5 µM |
| 891 | Ac | vpkGwr(D-Cha)hsiiss (SEQ ID NO: 5) | Amide | 0.43 ± 0.01 | ~8 µM | ~3.2 µM | -2.5 µM |
| 892 | Ac | SYSMEH(L-Cha)RWGKPV (SEQ ID NO: 6) | Amide | 0.51 | | | |
| 893 | Ac | vpkGWrfhemsys (SEQ ID NO: 78) | Amide | 6.5 | ~28 µM | >30 µM | ~27 µM |
| 894 | Ac | vpkGwRfhemsys (SEQ ID NO: 79) | Amide | 380 | >30 µM | >30 µM | >30 µM |
| 895 | Ac | vpkGwrfHemsys (SEQ ID NO: 80) | Amide | 19 | ~37 µM | ~11 µM | ~37 µM |

Lower case letters represent D-isomer amino acids; bold characters represent changes from RI α-MSH.

Binding of the peptides was followed by a competition with $^{125}$I-NDP-MSH for binding the melanocortin receptors 1, 3, 4, and 5 using membrane preparations from HEK293 cell lines. As shown in FIG. 18, RI α-MSH showed a very strong selectivity for MC1R, with Ki values in excess of 30 µM at both MC 3, 4 and 5R, whereas α-MSH showed significant binding to all four receptors, with less than 100-fold selectivity for MC1R relative to MC3R.

Example 4

Treatment with Retro-Inverso α-MSH Analog Ameliorates Disease in EAU

Immunomodulatory effects of the novel retro-inverso α-MSH peptide analog was observed in the experimental autoimmune uveitis mouse (EAU) model and compared results with the native α-MSH peptide. Systemic delivery of RI α-MSH at onset of disease or during late stage disease dramatically and reproducibly ameliorated uveitis. In addition, treatment with the novel RI α-MSH peptide analog suppressed uveitis with a similar magnitude to the native α-MSH peptide. These data indicate that the novel RI α-MSH analog shows anti-inflammatory activities and has therapeutic use in uveitis and other autoimmune diseases and inflammation.

Figure 2A:
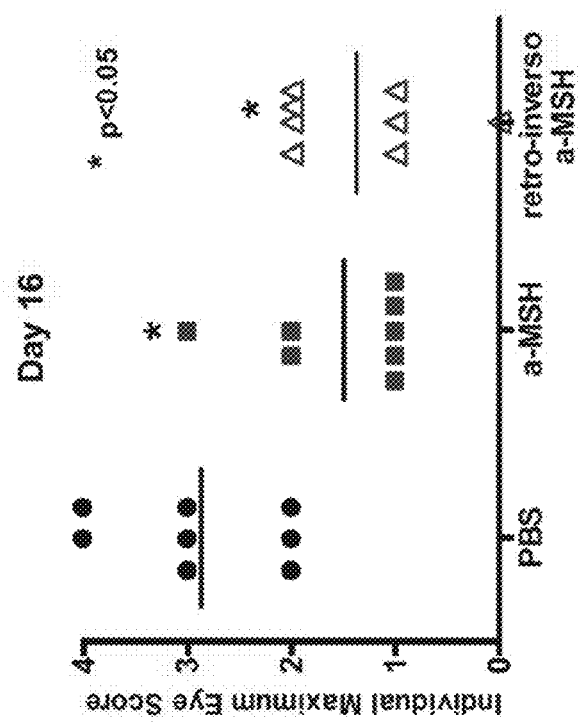
FIGS. 2A-B illustrate amelioration of uveitis in late-stage disease by RI α-MSH and native α-MSH. EAU was induced in B10.RIII mice and 100 µg/mouse native α-MSH, RI α-MSH or PBS was administered daily, i.v., on day 12 when mice reached late-stage disease (scores of 3).
Figure 2B:
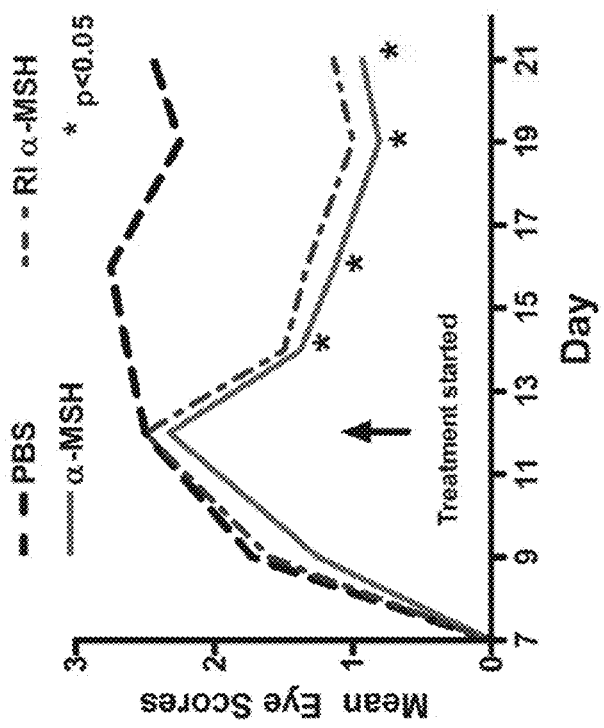

EAU was induced in female B10.RIII mice with IRBP 161-180. The efficacy of the RI α-MSH and native α-MSH as a therapeutic rather than a prophylactic treatment was examined. Mice were treated daily by intravenous injection with 100 µg/mouse RI α-MSH, 100 µg/mouse native α-MSH, or PBS beginning when mice reached a moderate disease stage of uveitis (eye scores of 2). As seen in FIG. 2A, control PBS-treated mice reached maximum eye scores on day 16 with a mean eye score of 2.75±0.68. However, mice treated daily with the RI α-MSH analog or native α-MSH showed a significant reduction of mean clinical eye scores throughout the course of treatment compared with PBS control mice. On day 16, four days after the start of treatment, 5 of the 8 mice in the PBS treated group had a maximum eye score of 3 or greater whereas only 1 of the 8 native α-MSH treated mice and 0 of the 8 RI α-MSH treated mice had a maximum eye score of 3 or greater (FIG. 2B).

Example 5

Figure 3A:
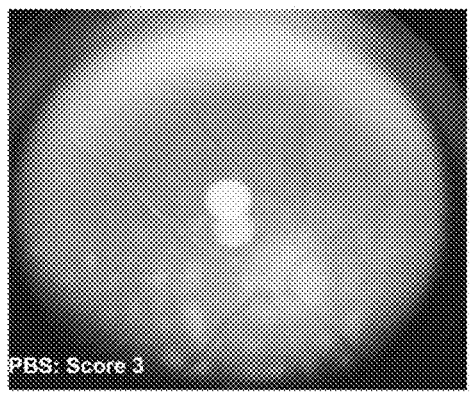
FIGS. 3A-D show retina images and individual eye scores from animals treated with α-MSH or RI α-MSH. EAU was induced in B10.RIII mice, and daily i.v. treatment with 100 µg/mouse of native α-MSH, RI α-MSH or PBS began on day 13 when mice reached late-stage disease. Fundoscopic images of retinas representing median eye scores from each group after 13 days of treatment are shown (n=11). The PBS treated mouse with an eye score of 3 shows inflammatory lesions in several quadrants of the eye and vasculitis proximal to the optic nerve (FIG. 3A). The α-MSH and RI α-MSH treated mice with eye scores of 1 show resolution of uveitis with inflammation only around the optic nerve (FIGS. 3B and 3C, respectively). Retinas represent median eye score from each group. Individual eye scores of mice in each group on day 13 post-treatment are shown in the graph (FIG. 3D). Asterisk denotes significant differences between groups (p<0.01).
Figure 3B:
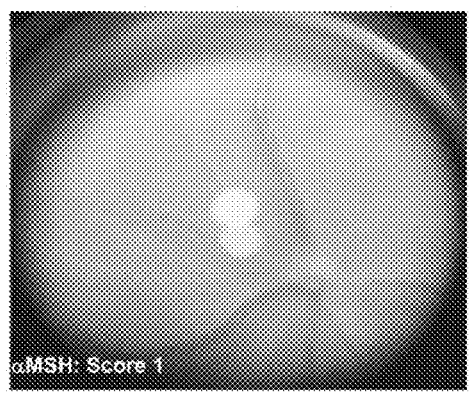
Figure 3C:
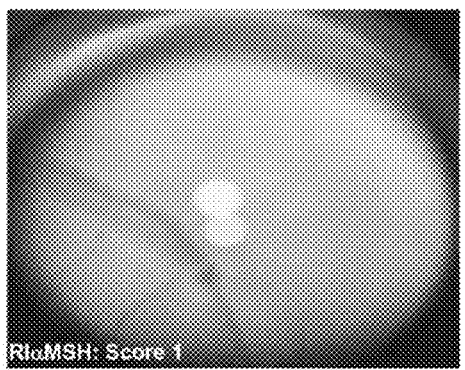
Figure 3D:
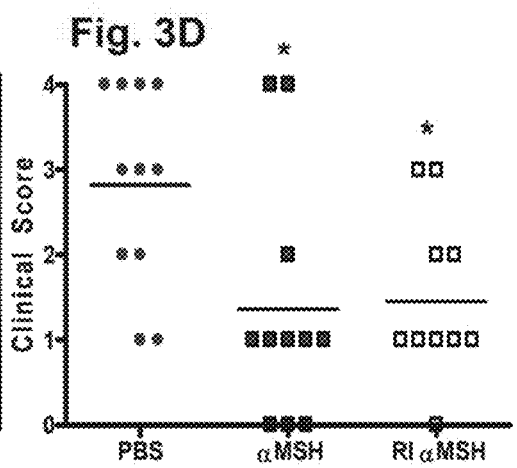

Retinal Images and Histological Examination of Subjects Treated with RI α-MSH Show Suppression of Disease in EAU Models Retinal images from mice treated daily with RI α-MSH or native α-MSH beginning at late stage uveitis show suppression of disease compared with PBS control mice. Fundoscopic images were acquired on day 13 after start of treatment (FIG. 3). Disease in the PBS treated group stabilized or advanced and had a median eye score of 3 with severe vasculitis and inflammatory lesions throughout the eye (FIG. 3A). However, disease rapidly resolved in both the RI α-MSH and native α-MSH peptide treated mice. Retina images showed eye scores of 1 with inflammation only at the optic nerve (FIGS. 3B and 3C). Maximum eye scores for individual mice in each group are shown in FIG. 3D. In the PBS treated group 7 of the 11 mice had eye scores 3 or greater. However, only 2 of the 11 mice in the native α-MSH and RI α-MSH had eye scores of 3 or greater.

Figure 4A:
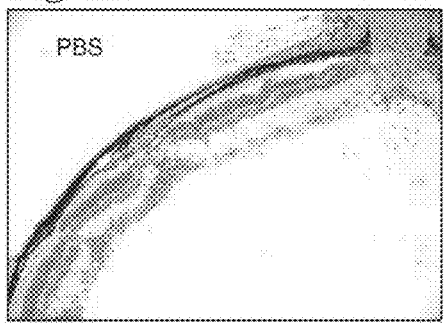
FIGS. 4A-C illustrate histopathology of RI α-MSH and native α-MSH treated mice in EAU. Female B10.RIII mice were injected with IRBP+CFA to induce EAU. Mice were treated daily, i.v., with 100 µg/mouse of retro-inverso α-MSH, native α-MSH, or PBS when mice reached eye scores of 3. The RI α-MSH or α-MSH treated group of mice ameliorated the ocular inflammatory response (p<0.05). Photographs show a hematoxylin and eosin staining of eyes 10 days after the start of treatment representing median eye scores from PBS (FIG. 4A), α-MSH (FIG. 4B) and RI α-MSH (FIG. 4C) treated groups of mice. Magnification is 100×.
Figure 4B:
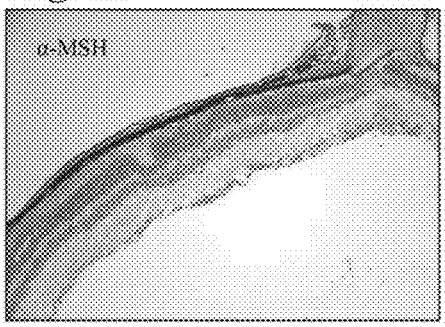
Figure 4C:
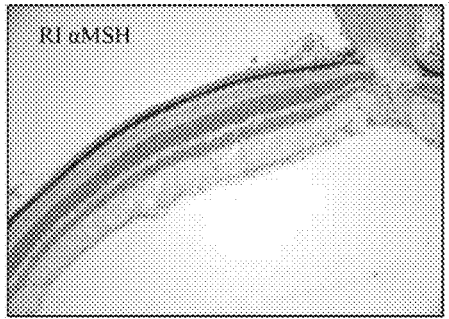

Histological examination of the eyes 10 days after the start of daily treatment showed that both RI α-MSH and native α-MSH reduced pathology in the eye (FIG. 4). The native α-MSH and RI α-MSH treated mice show normal retinal architecture with slight inflammation in the optic nerve region (FIGS. 4B and 4C). In contrast, PBS treated mice show ocular inflammation and tissue damage. Inflammation is seen in the retina and optic nerve regions with photoreceptor damage (FIG. 4A).

Example 6

Figure 5:
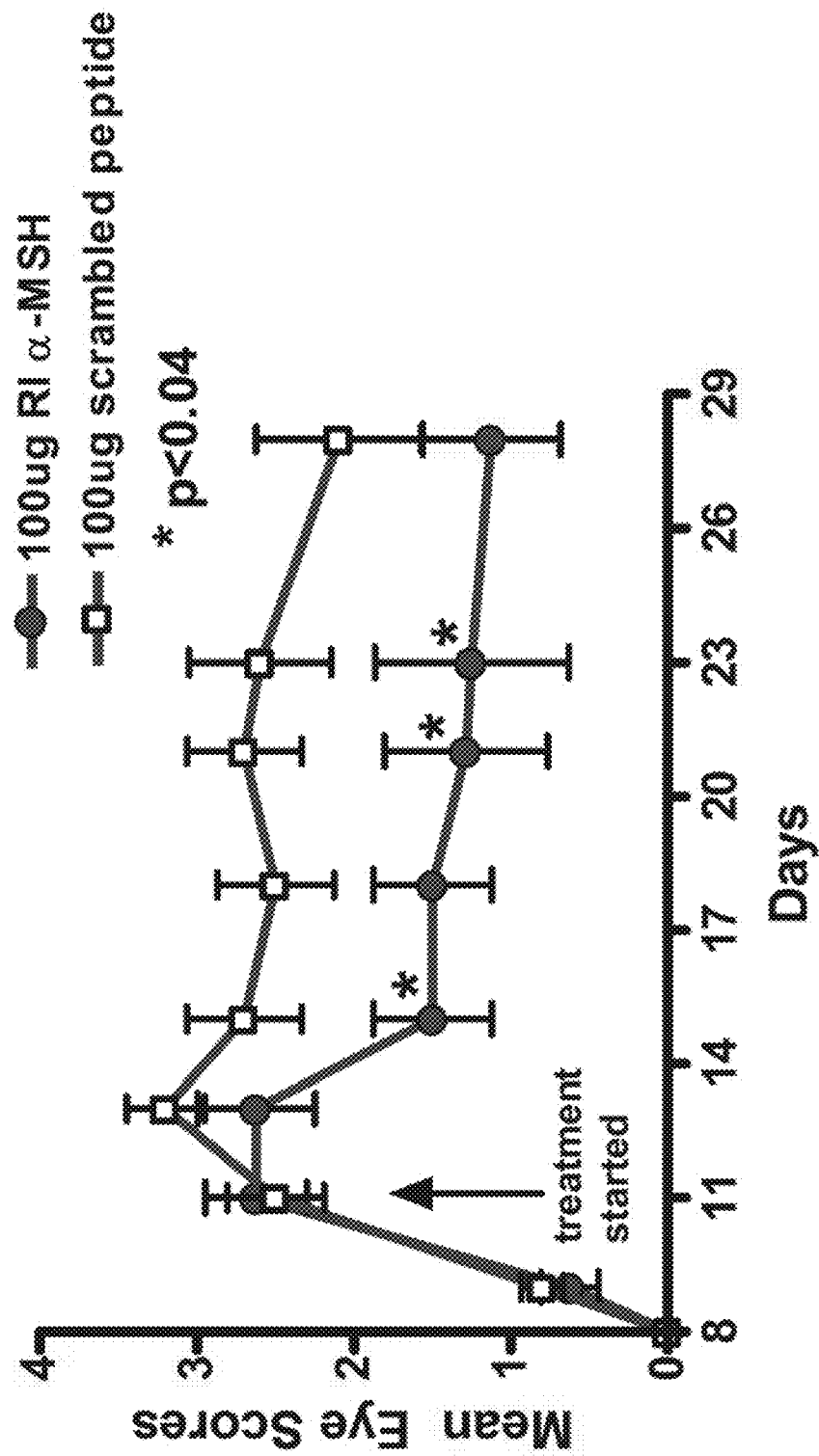
FIG. 5 shows the effect of intraperitoneal daily dosing of retro-inverso α-MSH on uveitis compared with a scrambled peptide control. B10.RIII mice were treated daily by intraperitoneal injections with 100 µg of RI α-MSH or a scrambled D amino acid peptide control on day 11 after disease induction. Data show the clinical mean eye scores of RI α-MSH (n=4) and scrambled control peptide (n=5) treated groups of mice. Mice were treated a total of 13 days.

Comparison of Intraperitoneal Administrations of Retro-Inverso α-MSH to a Scrambled Control Peptide in EAU Uveitis was induced in B10.RIII mice with IRBP161-180 and CFA injections. We evaluated initiating treatment during late-stage disease (eye scores of 2-3) with RI α-MSH by daily intraperitoneal injections and compared efficacy with a control scrambled D amino acid peptide. Mice were treated daily, i.p., for 13 days with RI α-MSH or scrambled peptide at 100 µg/mouse. Mice treated with RI α-MSH showed a significant reduction (p<0.04) in the mean clinical eye scores on days 15, 21 and 23 of the disease course compared with scrambled peptide control mice (FIG. 5). Individual maximum eye scores on day 23 after disease induction showed 75% of mice with scores ≤1 in the RI α-MSH compared with none of the mice in the control scrambled peptide group with scores ≤1. Individual weights of the mice were recorded at 4 timepoints throughout the course of disease. All mice in both the RI α-MSH treated and scrambled peptide treated groups maintained their weight or showed normal weight gain (data not shown). Daily intraperitoneal dosing with the peptides did not result in weight loss. In addition the intraperitoneal route of administration of native α-MSH or RI α-MSH at 100 μg/mouse had efficacy in uveitis when treatment was administered at onset of disease, when mice reach a clinical eye score of 1 (data not shown). Therefore, intraperitoneal route of administration of RI α-MSH showed significant reduction in disease scores compared with a scrambled control peptide.

Example 7

Administration of RI α-MSH at Various Dosages to EAU Model

We also examined the efficacy and optimal dosing of retro-inverso α-MSH treatment during late-stage severe uveitis. B10.RIII mice were injected with IRBP161-180 and CFA to induce uveitis. Mice were treated daily, i.p., with PBS, control scrambled peptide (100 μg/mouse), or RI α-MSH at 100 μg, 10 μg or 3 μg/mouse. Treatment was initiated at peak time of disease when mice reached eye scores of 4 which included inflammatory lesions throughout the posterior segment of the eye and possible hemorrhaging. Disease in PBS and scrambled peptide control groups remained severe (FIG. 6). In contrast, treatment with RI α-MSH at 100 μg or 10 μg/mouse rapidly ameliorated uveitis (p≤0.05). In addition, doses of 10 and 100 μg/mouse were equally effective. The 3 μg/mouse dose of RI α-MSH did not reduce or inhibit disease.

Example 8

Effect of Retro-Inverso α-MSH on cAMP Levels cAMP levels in B16-F1 melanoma cells after treatment with native α-MSH, RI α-MSH, or a scrambled control peptide were examined. The B16-F10 melanoma cell line expresses a high number of MCR1 receptors (3000-4000 receptors/cell) compared with macrophages cell lines which express only 100-200 receptors/cell. Therefore we selected to examine the effect of the RI α-MSH treatment on the melanoma cell line. Murine melanoma B16-F1 cells were treated with native α-MSH, RI α-MSH, or control scrambled peptide at concentrations 1 pg/ml-1 μg/ml. After 30 min, cells were lysed and intracellular cAMP was measured by an enzyme immunoassay. Forskolin, commonly used to raise cAMP levels, control (100 μM) treatment of cells showed an increase in cAMP (3455.39±406.6 SD). cAMP levels were significantly elevated in a dose dependent manner in cells treated with native α-MSH compared with untreated cells (FIG. 7A). The RI α-MSH analog also significantly increased cAMP levels in a dose dependent manner compared with untreated or scrambled peptide control. However, a higher concentration of RI α-MSH (100 ng/ml) was necessary to increase cAMP compared with native α-MSH which increased cAMP at a 10 pg/ml concentration. This difference in concentration of peptide necessary to increase cAMP levels may be the result of the binding affinity to the MCR1 receptor.

Example 9

Sequence Variation and Effects on cAMP Levels and Binding MC1R

MSH binds to MC1R, MC3R, MC4R, and MC5R, with MC1R being one of the desired targets for immune mediated diseases. Retro-inverso MSH (RI-MSH) has been engineered to have enhanced plasma stability (FIG. 17) and MC1R selectivity, but its affinity for MC1R is 11-fold lower than that of the native MSH peptide (Table 1). To restore MC1R affinity, we grafted into RI-MSH modifications known to improve MC1R affinity of MSH. Of the three replacements of the N-terminal SYSME sequence—fatty acyl, phenyl butyric acid, and SSIIS sequence—that enhance MC1R affinity of MSH, only the last one led to significant improvements for RI-MSH. D-alanine scanning analoging of RI-MSH exhibited a similar structure activity relationship as alanine scanning analoging of MSH, but stereochemistry inversion scanning of the core 4-residue MC1R binding region suggests significant differences between MSH and RI-MSH. Furthermore, cyclohexylalanine substitution at the key phenylalanine residue improved RI-MSH, but not MSH binding to MC1R. Combining cyclohexylalanine and SSIIS substitutions led to full restoration of MSH affinity for MC1R, while retaining the retro-inversion configuration critical for the improved stability and the high MC1R selectivity of RI-MSH.

A set of alanine scanning analogs (peptides 804-816) of retro-inverso MSH (RI-MSH) were prepared and tested for cAMP induction in B 16/F1 murine and M624 human melanoma cells. A subset based on the cAMP results were then tested for binding MC1R. The observed Ki values for binding MC1R are shown in Table 1.

Murine melanoma B16-F1 cells were treated with native α-MSH, RI α-MSH, scrambled peptide control, KPV, or alanine substituted peptides of RI α-MSH at 1 μg/ml (FIG. 7B). Forskolin control (100 μM) treatment of cells showed increase in cAMP (3294.82±54.53). cAMP levels were significantly elevated in cells treated with native α-MSH and RI α-MSH compared with untreated, scrambled peptide, or KPV treated cells. Alanine substituted peptides designated 810, 811, and 812 showed no increase in cAMP activity and exhibited levels of cAMP equivalent to untreated, scrambled peptide or KPV treated cells. Peptides designated 810, 811, and 812 have alanine substitutions in the central core tetrapeptide sequence (D-Trp D-Arg D-Phe D-His region; AA 5-8) (variant disclosed in SEQ ID NO:2) proposed to be involved in native α-MSH binding to the melanocortin receptor and its biological activity. Alanine substitutions at the N terminal or C terminal regions of the RI α-MSH peptide did not affect cAMP accumulation in the melanoma cells. Alanine substitutions in the methionine and histidine amino acids (807 and 809) also showed a reduction in cAMP accumulation although not as great as that seen in the core tetrapeptide sequence (810, 811 or 812). The residues in the core tetrapeptide (wrfh) (variant disclosed in SEQ ID NO:2) and to a lesser extent, the methionine 4 of RI-MSH are critical for binding to MC1R.

Another means shown to increase the affinity of MSH for MC1R has been demonstrated using selections based on phage display of MSH variant sequences. A highly MC1R-selective sequence (MS05) was subsequently found by recombination of the phage display-selected peptide and a portion of the parent MSH sequence, which yielded a subnanomolar affinity for MC1R. Unexpectedly, the retro-inverso version of this sequence showed a higher affinity for MC1R (1 nM, Table 1 peptide 886) than RI-MSH (4 nM), even though MS05 was reported to have a slightly lower affinity for MC1R than MSH (Ki 0.865 nM vs. 0.557 nM for MSH).

Substitution of a number of non-natural amino acid residues incorporating slight differences in charge and structure at each of the positions of RI-MSH showed that MC1R tolerates only highly conservative changes. All but 3 showed lesser or equivalent binding. Two changes provided a significant increase in affinity for MC1R: substitution of the D-phenylalanine by D-cyclohexylalanine (D-Cha, peptide 869; 2.2 nM Ki) and substitution of the D-methionine by D-buthionine (peptide 878, 2.3 nM Ki). Substitution with L-cyclohexylalanine was performed and was found to slightly inhibit binding to MC1R (peptide 892, Ki of 0.51 nM vs. 0.41 nM for MSH). Unexpectedly, combination of the buthionine and cyclohexylalanine substitutions failed to produce a further significant increase in affinity for MC1R (peptide 890, 1.9 nM Ki). However, combination of the change comprising substitution of the retro-inverso N-terminal sequence of MS05 (siiss) (SEQ ID NO:3) for the C-terminal sequence (emsys) (SEQ ID NO:34) and D-cyclohexylalanine for D-Phe in RI-MSH produced a greater enhancement of binding than each of the changes alone, indicating the effects are synergistic. The resulting peptide (891) showed a Ki for MC1R indistinguishable from MSH. Although this and the other changes also produced increases in the affinity for the other MCR's, the Ki values were still in the micromolar range, indicating the selectivity of RI-MSH was largely preserved. The changes are illustrated in FIGS. 20A-C. A representative competitive binding assay is shown in FIG. 21. See Table 1 for the observed Ki values.

Example 10

Treatment with RI α-MSH Reduces Clinical Disease Scores in EAE

The effect of administration of native α-MSH and RI α-MSH analog in a chronic progressive EAE mouse model was evaluated. Female C57BL/6 mice were immunized with 200 μg MOG 35-55 peptide emulsified with CFA. Pertussis toxin was administered on day 0 and 2. Mice were monitored daily for signs of clinical symptoms and weight loss. Mice were evaluated for symptoms of paralysis starting on day 8 and were scored on a grading system from 0-5. The appearance of clinical symptoms of paralysis manifested around day 9-11 in most mice (FIG. 8A). Daily intraperitoneal (i.p.) treatment with α-MSH or RI α-MSH peptide at 100 μg/mouse or PBS control began on day 10. Mice treated with 100 μg of RI α-MSH showed a significant reduction in the mean clinical disease score compared with PBS control (FIG. 8A). Significance of p≤0.05 was reached on days 14-22 in the RI α-MSH compared with PBS vehicle control. However the native α-MSH peptide treatment did not have an effect on disease induction or progression. The maximum percent incidence of disease in the RI α-MSH treated group of mice (20%) was also reduced compared with the PBS (80%) or native α-MSH treated (75%) groups of mice.

Example 11

Dosage Variation of RI α-MSH in EAE

The therapeutic effect of RI α-MSH was apparent at the 100 μg/mouse dose. Treatment with α-MSH or RI α-MSH peptide at 100 μg/mouse and 30 μg/mouse was tested in the MOG EAE mouse model. Daily i.p. treatment began on Day 10 after MOG immunization. Daily dexamethasone (2 mg/kg) treatment was added as a control therapeutic. Mice that were treated with 100 μg of RI α-MSH repeatedly showed a reduction in the mean clinical disease score compared with PBS control (FIG. 9). However the 30 μg/mouse dose of RI α-MSH did not have a significant effect on reducing mean clinical scores. Dexamethasone treatment also showed a reduction in disease scores throughout the course of disease. Although mice treated with native α-MSH had a lower mean clinical score than PBS, the α-MSH treated mice did not show similar efficacy as the RI α-MSH or dexamethasone treated mice. The percent incidence of disease in the RI α-MSH treated group reached a maximum of 35% and the dexamethasone 40% compared with PBS treated mice which showed a 75% maximum incidence of disease (FIG. 9). These data indicate that treatment with the RI α-MSH peptide analog in EAE significantly decreases mean clinical disease scores and incidence of disease.

Example 12

CNS Histology

Spinal cords were harvested on day 24 after disease induction in PBS and RI α-MSH treated mice. Hematoxylin and eosin staining of spinal cord sections were used to assess the degree of inflammation and number of lesions. The pathology of EAE shows focal areas of infiltration of inflammatory cells and demyelination. Histopathological evaluation of the spinal cord demonstrated efficacy of RI α-MSH treatment in the MOG EAE model. Slices from representative mice of the mean clinical score for each treatment group are shown in FIGS. 10A-10D. Data show extensive inflammatory infiltrates in the PBS treated group of mice compared with RI α-MSH treated mice which lack focal area of inflammation.

Example 13

Measurement of TNF-α and IL-10 in the Spleen During Disease Progression

The mechanism of action of the effects of RI α-MSH treatment in EAE was examined. Native α-MSH has been reported to have an effect on monocytes/macrophages by decreasing TNF-α levels and increasing IL-10. TNF-α and IL-10 mRNA levels in the spleen of MOG primed mice treated with RI α-MSH or native α-MSH were evaluated by quantitative PCR. Mice were immunized with MOG p35-55 and daily treatment with RI α-MSH or native α-MSH started on Day 10. Spleen samples were harvested from mice on Days 1, 4 and 7 after start of daily treatment. Data show treatment with RI α-MSH and α-MSH significantly decreased (p≤0.001) TNF-α compared with PBS control after 7 days of daily treatment (FIG. 11E). However there was no significant change in the TNF-α level at previous time points (Day 1 and Day 4; FIGS. 11A and 11C). IL-10 mRNA levels were also reduced at the Day 7 timepoint in both the RI α-MSH and αMSH treatment groups compared with PBS control (FIG. 11F). However, no difference in IL-10 mRNA levels was detected at the earlier timepoints (FIGS. 11B and 11D). Although native α-MSH treatment did not reduce mean clinical disease scores or percent incidence of disease, in this study α-MSH treatment reduced both TNF-α and IL-10 mRNA levels in the spleen compared with PBS control by Day 17 of disease progression. RI α-MSH analog is able to reduce TNF-α mRNA levels in the spleen after daily treatment.

Example 14

Effect of RI α-MSH on Recall Response to MOG Peptide

The effects of treating mice with α-MSH or RI α-MSH in vivo on recall responses to the MOG 35-55 peptide were evaluated. Mice were primed with MOG35-55 peptide and on Days 2-8 mice were either treated with PBS, 100 μg α-MSH or 100 μg RI α-MSH. On Day 9, spleen and draining lymph nodes were harvested and analyzed for recall responses to MOG35-55 peptide in vitro by [3H] thymidine incorporation. Data show a significant decrease in proliferative responses of spleen cell to MOG35-55 peptide in the α-MSH group of mice compared with the PBS treated group (FIG. 12A). The RI α-MSH treated group showed a slight reduction in recall responses to MOG35-55 peptide. However, recall responses to MOG peptide in the lymph node cell population did not show a significant difference in responsiveness between the PBS, α-MSH, and RI α-MSH treated groups (FIG. 12B).

Cell supernatant was collected from the spleen cells that were stimulated with MOG35-55 peptide in vitro from each of the in vivo treatment groups (naïve, PBS, α-MSH, RI α-MSH). Cytokine levels were evaluated through a cytometric bead array by flow cytometry. Data show a decrease in TNF-α, IFNγ, IL-6 and MCP-1 levels in both the α-MSH and RI α-MSH treated groups compared with the PBS treated group (FIGS. 12C and 12D). The cytokine levels of spleen cells supernatant in both the α-MSH and RI α-MSH treated groups were similar to cytokine levels from spleen cells of unprimed mice.

Therefore, RI α-MSH peptide treatment had an effect on cytokine recall responses to MOG peptide but did not affect T cell proliferation responses.

Example 15

Effects of Treating Mice with α-MSH or RI α-MSH During the Priming Phase of EAE

Mice were immunized with MOG 35-55 peptide and on days 2-8 treated daily with PBS vehicle control, α-MSH, or RI α-MSH. Spleens from individual mice were harvested on Day 9 and mRNA cytokine expression was quantitated using real time PCR. FIG. 13A-13D shows TNF-α and IL-10 mRNA expression levels in the spleen of PBS, α-MSH or RI α-MSH treated mice in the priming phase of disease. Naïve mice that were not immunized with MOG peptide were used to quantitate baseline mRNA levels of TNF-α and IL-10. Treatment with either α-MSH or RI α-MSH decreased levels of IL-10 and TNF-α mRNA compared with PBS vehicle control.

Blood serum samples were also collected on day 9 of the study and evaluated for cytokine levels: TNF-α, MCP-1, IL-12, IL-10, and IL-6 (FIGS. 13C and 13D). Data show a decrease in MCP-1 and IL-6 in both the α-MSH and RI α-MSH treated groups compared with the PBS control group. MCP-1 was significantly decreased (p<0.01) in the RI α-MSH treated group compared with PBS control. Additionally, the RI α-MSH treated group showed a decrease in TNF-α and IL-12 compared with the PBS group. There was no difference in serum IL-10 levels between the three treated groups.

Example 16

RI α-MSH Does Not have an Effect on Macrophage Markers

Splenic CD11b$^+$ and F4/80$^+$ macrophages were examined for surface expression levels of CD86, CD40, and CD14 by flow cytometry after 7 days of daily dosing with α-MSH or RI α-MSH in MOG 35-55 immunized mice. Data show no difference in the expression levels of CD86, CD40 or CD14 in the splenic CD 11b$^+$ or F4/80$^+$ macrophage cell population in mice treated with α-MSH or RI α-MSH (FIGS. 14A and 14B). Results showed a similar finding when blood monocytes were examined for CD86, CD40, and CD14 expression levels (data not shown).

Example 17

Effects in the LPS Inflammation Mouse Model

Native α-MSH has been reported to inhibit inflammation by downregulating TNF-α production through stimulation of melanocortin receptors (MCR), in particular the melanocortin 1 receptor. LPS stimulates inflammatory mediators such as TNF-α, MCP-1, IL-6 and IFNγ and has been used as an acute inflammation model. Whether an α-MSH analog can suppress inflammatory cytokines in a LPS mouse inflammation model was examined. The levels of MC1R expression in the spleen and peritoneal macrophages after LPS administration were determined. C57BL/6 mice were injected with LPS, i.p. and at several timepoints post-LPS injection spleen and peritoneal macrophages were harvested for analysis. Data show no discernable difference in the levels of MC1R mRNA expression among any of the timepoints in peritoneal macrophages (FIG. 15A). However, LPS administration did increase mRNA levels of MC1R above naïve mice that did not receive a LPS challenge. In the spleen the levels of MC1R mRNA were elevated 30 minutes post-LPS injection and then decreased by one hour post-injection (FIG. 15B). LPS similarly increased mRNA levels of MC1R in the spleen above baseline levels in naïve mice.

Figure 16A:
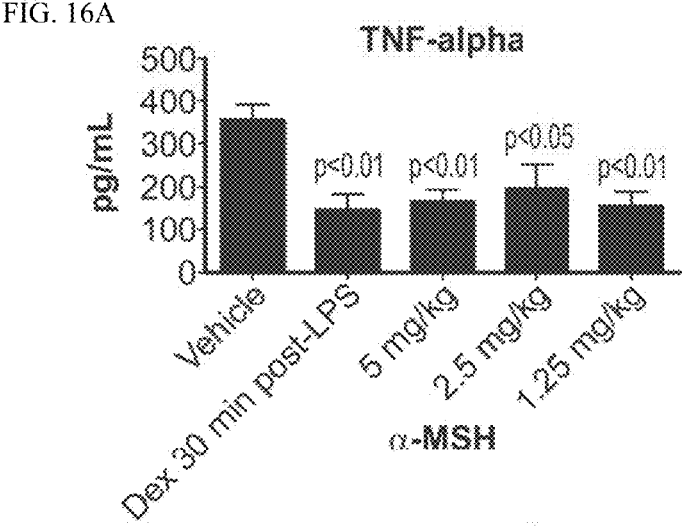
Figure 16B:
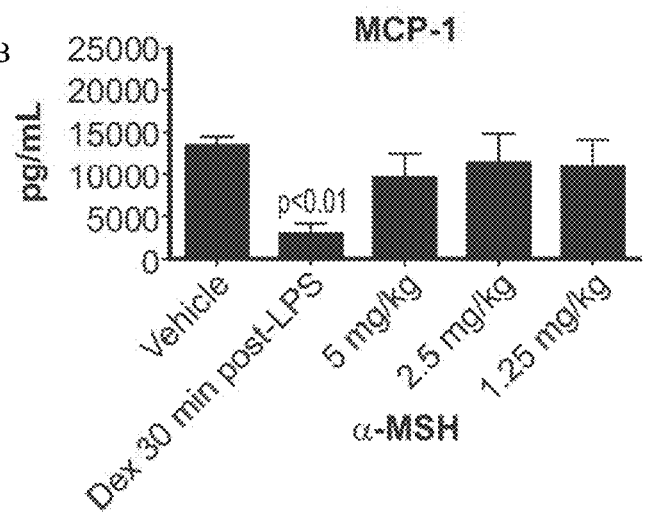
Figure 16C:
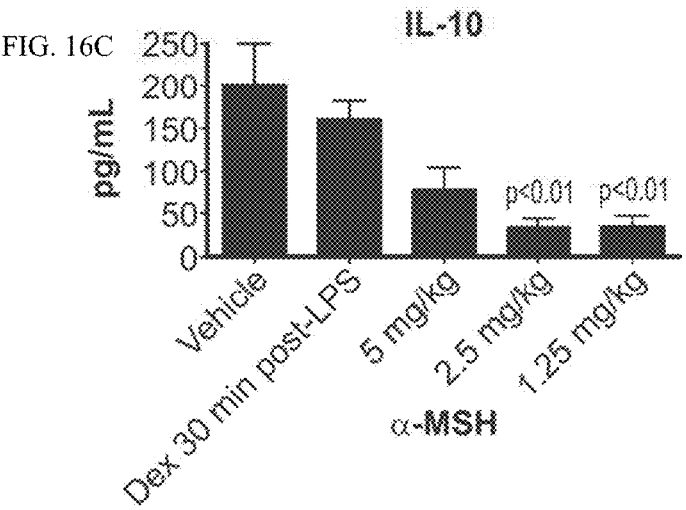
Figure 16D:
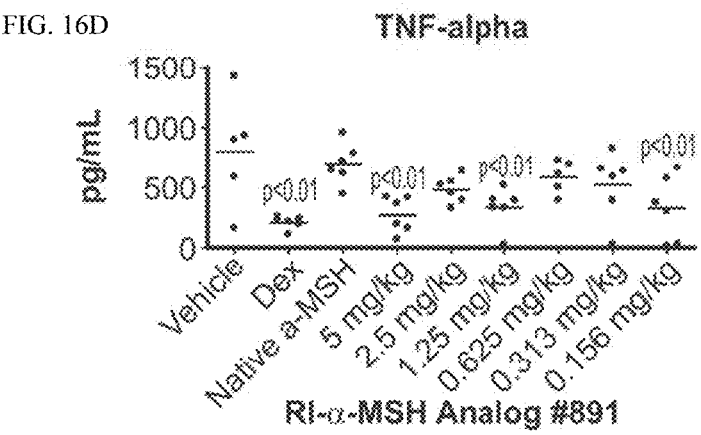
Figure 16E:
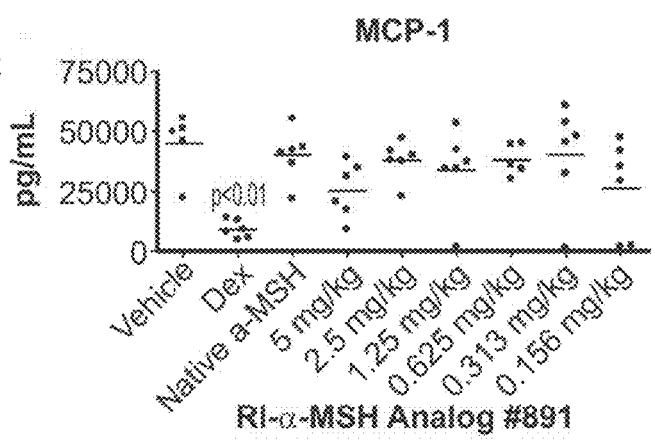
Figure 16F:
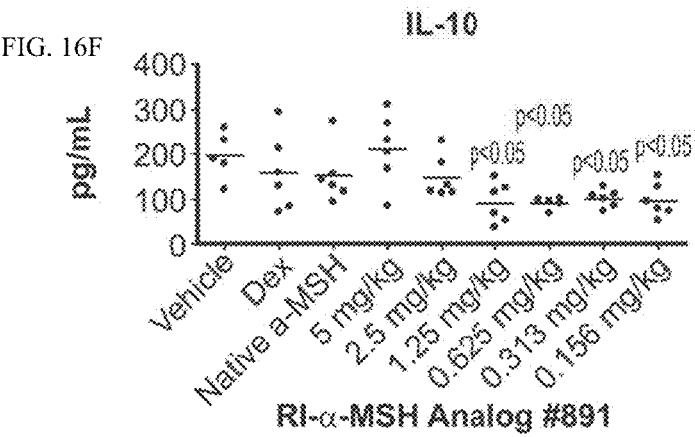

Data demonstrating MC1R mRNA expression in spleen and peritoneal macrophages indicated that 30 minutes post-LPS challenge might be the optimal timepoint for α-MSH or RI α-MSH analog treatment. C57BL/6 mice were injected with LPS, i.p. and 30 minutes later native α-MSH or RI α-MSH analog 891 was administered i.p. at doses ranging from 5 mg/kg to 0.156 mg/kg. RI α-MSH analog 891 is an analog of RI α-MSH in which d-Cha and hsiiss D-amino acids were added to the core peptide sequence. The RI α-MSH analog 891 has shown to have increased binding affinity to mouse MC1R and increased potency to stimulate cAMP (data not shown). Results showed significant reduction in TNF-α and IL-10 levels in the native α-MSH treated groups compared with PBS vehicle control (FIGS. 16A and 16C). MCP-1 was not affected by native α-MSH treatment (FIG. 16B). Treatment of LPS challenged mice with RI α-MSH analog 891 showed similar results with a significant decrease in TNF-α and IL-10 with no affect on MCP-1 levels compared with vehicle control (FIGS. 16D and 16F). Lower doses of both native α-MSH and RI α-MSH analog 891 showed the greatest suppression of inflammatory cytokines. Dexamethasone positive control consistently showed suppression of TNF-α and MCP-1 levels.

Example 18

Stability of Peptides in Plasma

The serum half-life of native α-MSH has been estimated to be approximately 10 minutes. Despite this limited half-life, the peptide is still capable of eliciting potent anti-inflammatory activities. However, more stable α-MSH analogs are necessary to increase the potency of anti-inflammatory activities and be further developed as a therapeutic. A D-amino acid analog of native α-MSH (referred to as retro-inverso α-MSH or RI α-MSH) was synthesized and is more stable than native α-MSH. The D-amino acid form of peptides is more resistant to proteolysis and is metabolized at a slower rate than the L-amino acid form of peptides.

The stability of RI-α-MSH was determined by incubation in plasma or PBS in vitro at 37° C. for 24 hours. Aliquots were taken and proteins precipitated with 2 volumes of acetonitrile. α-MSH was used as a control and bradykinin as an internal standard. After centrifugation, samples were frozen at −80° C. until LC/MS/MS (MRM) analysis using a C18 column separation and positive electrospray ionization mode. As shown in FIG. 17a, MSH showed a half-life of about 3 hours in plasma, but was stable in PBS. However, RI-α-MSH was stable both in PBS and plasma, showing no detectable degradation over 24 hours.

The pharmacokinetic (PK) profiles for α-MSH and RI-α-MSH suggest that RI-α-MSH has a longer serum half-life than native α-MSH (FIG. 17b). Mice treated with a single dose of 100 µg RI-α-MSH or α-MSH had measurable serum levels of RI-α-MSH after 24 hrs but there were no detectable levels of α-MSH 120 minutes post-treatment (n=5).

Example 19

Binding Effects of Retro-Inverso Peptides

A core MSH tetrapeptide containing a D-Phe (HfRW) (variant disclosed in SEQ ID NO:1) is sufficient to produce significant binding to MC1R (20-50 nM Ki). However, very little binding is observed with the retro-inverso version of the same tetrapeptide (wrFh, (variant disclosed in SEQ ID NO:2) 883, Ki>30 uM, Table 1), showing that retro-inverso peptide fails to fully contact the receptor in the same fashion as HfRW (variant disclosed in SEQ ID NO:1). Addition of fatty acyl groups to the N-terminus of HfRW (variant disclosed in SEQ ID NO:1) selectively improves its binding to MC1R, yielding an affinity comparable to MSH. This is observed for the stearyl-HfRW (variant disclosed in SEQ ID NO:1) peptide at MC1R (1.3 nM, peptide 820). Addition of a diaminohexane stearyl group to the retro-inverso wrFh (variant disclosed in SEQ ID NO:2) (peptide 882) improves binding to MC1R (120 nM, >250-fold) and to a comparable extent as stearic acid addition to the N-terminus of HfRW (variant disclosed in SEQ ID NO:1) (80-fold), but does not achieve the affinity seen for RI-MSH (4.1 nM), again indicating other residues in RI-MSH play a larger role in binding of RI-MSH to MC1R than with MSH.

Example 20

Stereochemistry Effects on Binding of Retro-Inverso Peptides

The stereochemistry of the residues in the core retro-inverso tetrapeptide has a significantly different effect on the binding to MC1R than in the L-form MSH. As shown in FIG. 19, inversion of the core tetrapeptide residues in RI-MSH to the L-form (peptides 884, 893-895) all reduced the affinity of the peptide for MC1R. Strikingly and unexpectedly, inversion of the D-Phe to L-Phe in the RI sequence caused a 20-fold reduction in binding, whereas the corresponding change in HFRW (SEQ ID NO:33) (L-Phe to D-Phe) has been reported to improve binding as much as 400-fold. For the other residues, stereochemical inversion was found to have a lesser effect on RI-MSH than on the core HfRW peptide (variant disclosed in SEQ ID NO:1) again indicating the relative importance of each residue in the core tetrapeptide is lower in RI-MSH than in the HfRW tetrapeptide (variant disclosed in SEQ ID NO:1).

Example 21

Effects of End-Capping Retro-Inverso MSH

Another possible route to achieving higher affinity for MC1R is based on the observation that end-capping the HfRW peptide with phenyl butyric acid selectively and strongly increases the affinity of HfRW for MC1R (Ki=6 pM). However, no increase in the affinity of a truncated RI-MSH bearing a C-terminal phenylpropylamide (peptide 847) was observed, with a Ki of 150 nM observed for both the peptide truncated at the histidine residue (peptide 847int) and its aminopropyl-phenyl adduct (peptide 847, Table 1), demonstrating that with RI-MSH, binding is altered in a manner disallowing simultaneous interaction of the tetrapeptide sequence and the postulated aromatic interaction site near the histidine-binding element in MC1R.

Example 22

Synthesis of a Toxin Conjugate of Retroinverso MSH

A modified version of peptide 891 (Table 1) in which a cysteine is appended to the N-terminus is generated by Fmoc chemistry. A conjugate of monomethyl auristatin E (MMAE) containing a protease-sensitive valine-citrulline linker with a maleimido-caproyl moiety for coupling to thiols is synthesized according to Doronina et al. (2003) *Nature Biotechnol.* 21:778-784, incorporated herein by reference. The peptide and MMAE conjugate are incubated in a solution of 25 mM Na phosphate, 2 mM EDTA pH7 for 14 h at 25° C. and the product purified by C18 reverse-phase HPLC (RP-HPLC).

Example 23

Effect of RI α-MSH Analogs on cAMP in Murine Melanoma Cell Lines

Both native α-MSH and RI α-MSH increase cAMP levels in murine melanoma cells. RI α-MSH peptide analogs were generated to determine whether modifications to the core sequence of RI α-MSH peptide would elevate cAMP levels compared with the RI α-MSH peptide. A dose response experiment was carried out for the generated RI α-MSH analogs in the cAMP assay using murine B16-F1 melanoma cells.

In vitro cell cultures: B 16-F1 murine melanoma cells were cultured into 96 well plates 5×10$^4$ cells/well overnight in media with L-glutamine and pen/strep and FBS. Media was removed and new media with IBMX was added to the cells for 1 hr. Cells were then treated with RI α-MSH, or RI α-MSH peptide analogs (890, 891, 892, 893, 894 or 895). Cells were lysed after 30 min using a cAMP assay kit and supernatant were used in the assay. Forskolin at 10 μM served as positive controls.

cAMP levels: Intracellular cAMP was measured using a cAMP competition Assay Kit (Amersham Biosciences). All cell lysate samples were diluted 1:100 for analysis.

```
Peptides:
869     vpkGwr(d-Cha)hemsys (SEQ ID NO: 63)

872     vpkGwrfremsys (SEQ ID NO: 66)

880     vpkGwrFhsiiss (SEQ ID NO: 4)

878     vpkGwrfhe(d-buthionine)sys (SEQ ID NO: 72)

886     RI-MS05 vpkgwrfhsiiss (SEQ ID NO: 76)

890     vpkGwr(d-Cha)he(d-Buthionine)sys
        (SEQ ID NO: 77)

891     vpkGwr(d-Cha)hsiiss (SEQ ID NO: 5)

892     SYSMEH(Cha)RWGKPV (SEQ ID NO: 6)

893     vpkGWrfhemsys (SEQ ID NO: 78)

894     vpkGwRfhemsys (SEQ ID NO: 79)

895     vpkGwrfHemsys (SEQ ID NO: 80)
```

Results: Murine melanoma B16-F1 cells were treated with RI α-MSH, or RI α-MSH analogs (869, 872, 880, 878, 886 and 890-895) at a concentration range of $10^{-4}$-$10^{-11}$ M. cAMP levels from cells treated with RI α-MSH, or RI α-MSH analogs. The majority of the RI α-MSH analogs showed improved $EC_{50}$ values compared with RI α-MSH with the exception of analog 894. Analogs 891, 892 and 886 showed the greatest improvement in $EC_{50}$ values in the cAMP assay compared with the RI α-MSH peptide. In summary, RI α-MSH analogs showed an improved dose response and $EC_{50}$ value compared with the RI α-MSH peptide. See FIG. 22 for graphical data and Table 2 for $EC_{50}$ data.

TABLE 2

| | $EC_{50}$, μM | | $EC_{50}$, μM | | $EC_{50}$, μM |
|---|---|---|---|---|---|
| α-MSH | 0.0004 | α-MSH | 0.0004 | α-MSH | 0.0004 |
| RI α-MSH | 9.7 | RI α-MSH | 9.7 | RI α-MSH | 9.7 |
| Analog ID: | | Analog ID: | | Analog ID: | |
| 890 | 3.6 | 878 | 0.13 | 869 | 0.014 |
| 891 | 0.081 | 880 | 0.023 | 872 | 2.0 |
| 892 | 0.021 | 886 | 0.002 | 878 | 0.13 |
| 893 | 0.27 | | | | |
| 894 | 212 | | | | |
| 895 | 0.3 | | | | |

The invention claimed is:

1. A polypeptide comprising the sequence set forth in:

$Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$, wherein $Xaa_1$ is D-Val, D-Ala, or D-Lys;
$Xaa_2$ is D-Pro, D-Ala, or D-Lys;
$Xaa_3$ is D-Lys, D-Orn, D-Nle, or D-Ala;
$Xaa_4$ is Gly, or D-Ala;
$Xaa_5$ is D-Trp, Trp, D-3-benzothienyl-Ala, D-5-hydroxy-Trp, D-5-methoxy-Trp, D-Phe, or D-Ala;
$Xaa_6$ is D-Arg, D-His, or D-Ala;
$Xaa_7$ is D-Cha, D-Phe, Phe, D-4-fluoro-Phg, D-3-pyridyl-Ala, D-Thi, D-Trp, D-4-nitro-Phe, or D-Ala;
$Xaa_8$ is D-His, His, D-Arg, Phe, or D-Ala;
$Xaa_9$ is D-Glu, D-Asp, D-citrulline, D-Ser, or D-Ala;
$Xaa_{10}$ is D-Met, D-buthionine, D-Ile, or D-Ala;
$Xaa_{11}$ is D-Ser, D-Ile, or D-Ala;
$Xaa_{12}$ is D-Tyr, D-Ser, or D-Ala; and
$Xaa_{13}$ is D-Ser or D-Ala;

wherein:
no more than one of $Xaa_{1-13}$ is D-Ala except when $Xaa_{1-3}$ are all D-Ala, and,
no more than one of $Xaa_{1-13}$ is an L-amino acid;
or a pharmaceutically acceptable salt thereof.

2. The polypeptide or pharmaceutically acceptable salt thereof according to claim 1, wherein at least one of $Xaa_{1-13}$ is D-Ala except when $Xaa_{1-3}$ are all D-Lys.

3. The polypeptide or pharmaceutically acceptable salt thereof according to claim 1, said polypeptide comprising a core tetrapeptide having the sequence:

D-Trp D-Arg Xaa D-His (SEQ ID NO: 2), wherein Xaa is D-Cha, D-Phe, or Phe.

4. The polypeptide or pharmaceutically acceptable salt thereof according to claim 1, said polypeptide comprising a C-terminal polypeptide having the sequence: D-Ser D-Ile D-Ile D-Ser D-Ser (SEQ ID NO: 3).

5. The polypeptide or pharmaceutically acceptable salt thereof according to claim 1, said polypeptide comprising the sequence set forth in:

(SEQ ID NO: 34)
D-Val D-Pro D-Lys Gly D-Trp D-Arg D-Phe D-His D-Glu D-Met D-Ser D-Tyr D-Ala;

(SEQ ID NO: 35)
D-Val D-Pro D-Lys Gly D-Trp D-Arg D-Phe D-His D-Glu D-Met D-Ser D-Ala D-Ser;

(SEQ ID NO: 36)
D-Val D-Pro D-Lys Gly D-Trp D-Arg D-Phe D-His D-Glu D-Met D-Ala D-Tyr D-Ser;

(SEQ ID NO: 37)
D-Val D-Pro D-Lys Gly D-Trp D-Arg D-Phe D-His D-Glu D-Ala D-Ser D-Tyr D-Ser;

(SEQ ID NO: 38)
D-Val D-Pro D-Lys Gly D-Trp D-Arg D-Phe D-His D-Ala D-Met D-Ser D-Tyr D-Ser;

(SEQ ID NO: 43)
D-Val D-Pro D-Lys D-Ala D-Trp D-Arg D-Phe D-His D-Glu D-Met D-Ser D-Tyr D-Ser;

(SEQ ID NO: 44)
D-Val D-Pro D-Ala Gly D-Trp D-Arg D-Phe D-His D-Glu D-Met D-Ser D-Tyr D-Ser;

(SEQ ID NO: 45)
D-Val D-Ala D-Lys Gly D-Trp D-Arg D-Phe D-His D-Glu D-Met D-Ser D-Tyr D-Ser;

(SEQ ID NO: 46)
D-Ala D-Pro D-Lys Gly D-Trp D-Arg D-Phe D-His D-Glu D-Met D-Ser D-Tyr D-Ser;

(SEQ ID NO: 47)
D-Ala D-Ala D-Ala Gly D-Trp D-Arg D-Phe D-His D-Glu D-Met D-Ser D-Tyr D-Ser;
or (SEQ ID NO: 48)
D-Lys D-Lys D-Lys Gly D-Trp D-Arg D-Phe D-His D-Glu D-Met D-Ser D-Tyr D-Ser.

6. The polypeptide or pharmaceutically acceptable salt thereof according to claim 1, wherein said polypeptide is PEGylated.

7. The polypeptide or pharmaceutically acceptable salt thereof according to claim 1, wherein said polypeptide exhibits at least one of the following properties:
  ability to selectively activate melanocortin 1 receptor (MC1R);
  stability in plasma in vitro; or
  resistance to protease degradation.

8. The polypeptide or pharmaceutically acceptable salt thereof according to claim 1, wherein said polypeptide is conjugated to a biologically active moiety.

9. A pharmaceutical composition comprising the polypeptide or pharmaceutically acceptable salt thereof according to claim 1, and a pharmaceutically acceptable excipient.

10. A composition for treating an autoimmune disease or condition in a subject in need thereof, comprising a therapeutically effective amount of the polypeptide or pharmaceutically acceptable salt thereof according to claim 1, and a pharmaceutically acceptable excipient,
  wherein said autoimmune disease or condition is selected from the group consisting of multiple sclerosis, diabetes type I, aplastic anemia, Grave's disease, coeliac disease, Crohn's disease, lupus, arthritis, osteoarthritis, autoimmune uveitis, and myasthenia gravis.

11. A composition for treating inflammation in a subject in need thereof, comprising a therapeutically effective amount of the polypeptide or pharmaceutically acceptable salt thereof according to claim 1, and a pharmaceutically acceptable excipient,
  wherein said inflammation is associated with a disease selected from the group consisting of inflammatory bowel disease, rheumatoid arthritis, allergy, atherosclerosis, psoriasis, gastritis, and ischemic heart disease.

12. A composition for reducing or inhibiting transplant rejection in a subject in need thereof, comprising a therapeutically effective amount of the polypeptide or pharmaceutically acceptable salt thereof according to claim 1, and a pharmaceutically acceptable excipient.

13. A composition for treating melanoma in a subject in need thereof, comprising a therapeutically effective amount of the polypeptide or pharmaceutically acceptable salt thereof according to claim 1, and a pharmaceutically acceptable excipient.

14. A composition for treating melanoma in a subject in need thereof comprising a therapeutically effective amount of a conjugate comprising the polypeptide or pharmaceutically acceptable salt thereof according to claim 1 conjugated to a cytotoxic agent, and a pharmaceutically acceptable excipient.

* * * * *